(12) United States Patent
Biron et al.

(10) Patent No.: US 8,222,382 B2
(45) Date of Patent: Jul. 17, 2012

(54) HIV TYPE AND SUBTYPE DETECTION

(75) Inventors: Marie-Philippe Biron, Asnières-sur-Seine (FR); Alain Horvais, Herblay (FR)

(73) Assignee: Bio-Rad Innovations, Marnes la Coquette (FR)

( * ) Notice: Subject to any disclaimer, the term of this patent is extended or adjusted under 35 U.S.C. 154(b) by 942 days.

(21) Appl. No.: 11/628,326

(22) PCT Filed: Jun. 3, 2005

(86) PCT No.: PCT/EP2005/006513
§ 371 (c)(1),
(2), (4) Date: Apr. 30, 2007

(87) PCT Pub. No.: WO2005/118883
PCT Pub. Date: Dec. 15, 2005

(65) Prior Publication Data
US 2008/0318205 A1     Dec. 25, 2008

(30) Foreign Application Priority Data

Jun. 4, 2004   (EP) ..................................... 04291402

(51) Int. Cl.
*C07H 21/02*   (2006.01)
*C07H 21/04*   (2006.01)

(52) U.S. Cl. ................... 536/23.1; 536/24.3; 536/24.33; 435/975

(58) Field of Classification Search .......................... None
See application file for complete search history.

(56) References Cited

U.S. PATENT DOCUMENTS

| | | | |
|---|---|---|---|
| 5,474,796 A * | 12/1995 | Brennan | 427/2.13 |
| 5,712,385 A | 1/1998 | McDonough et al. | |
| 5,962,665 A | 10/1999 | Gorzowski et al. | |
| 2001/0053519 A1 * | 12/2001 | Fodor et al. | 435/6 |

FOREIGN PATENT DOCUMENTS

| | | |
|---|---|---|
| EP | 0 887 427 A | 12/1998 |
| EP | 1 043 407 A | 10/2000 |
| EP | 1 344 837 A | 9/2003 |
| WO | WO-03/020878 A1 | 3/2003 |

OTHER PUBLICATIONS

New England Biolabs 1998/99 Catalog (NEB Catalog).*
Schutten et al. (Virol Methods. Jul. 2000;88(1):81-7).*
Buck et al ("Design Strategies and Performance of Custom DNA Sequencing Primers" Biotechniques. 1999. 27(3): pp. 528-536).*
Swanson et al. (J Virol Methods. Sep. 2000;89(1-2):97-108).*
Lowe et al. (Nucleic Acids Research, vol. 18, No. 7, p. 1757-1761, 1990).*
Stratagene ("Gene Characterization Kits" 1988).*
Genbank Accession No. M30502 (Feb. 5, 1992).*
Genbank Accession No. K03455 (Jan. 14, 1992).*
Genbank Accession No. L20857 (Mar. 22, 1994).*
Swanson et al., Journal of Virological Methods, vol. 89, No. 1-2, Sep. 2000, pp. 97-108.
Schutten et al., Journal of Virological Methods, vol. 88, No. 1, Jul. 2000, pp. 81-87.
Database Medline 'Online! US National Library of Medicine (NLM), Bethesda, MD, US; Mar. 2004, Wei Min et al., "Development of a subtype screening assay for human immunodeficiency virus type 1 by nested multiplex PCR!" XP002306787, Database accession No. NLM15340536, abstract.
Tyagi, Sanjay et al., Nature Biotechnology, vol. 16, pp. 49-53 (Jan. 1998).
Tyagi, Sanjay et al., Nature Biotechnology, vol. 14, pp. 303-308 (Mar. 1996).

* cited by examiner

*Primary Examiner* — Christopher M. Babic
(74) *Attorney, Agent, or Firm* — Birch, Stewart, Kolasch & Birch, LLP

(57) ABSTRACT

The present invention relates to the detection of HIV by amplification and PCR-based methods.

26 Claims, 25 Drawing Sheets

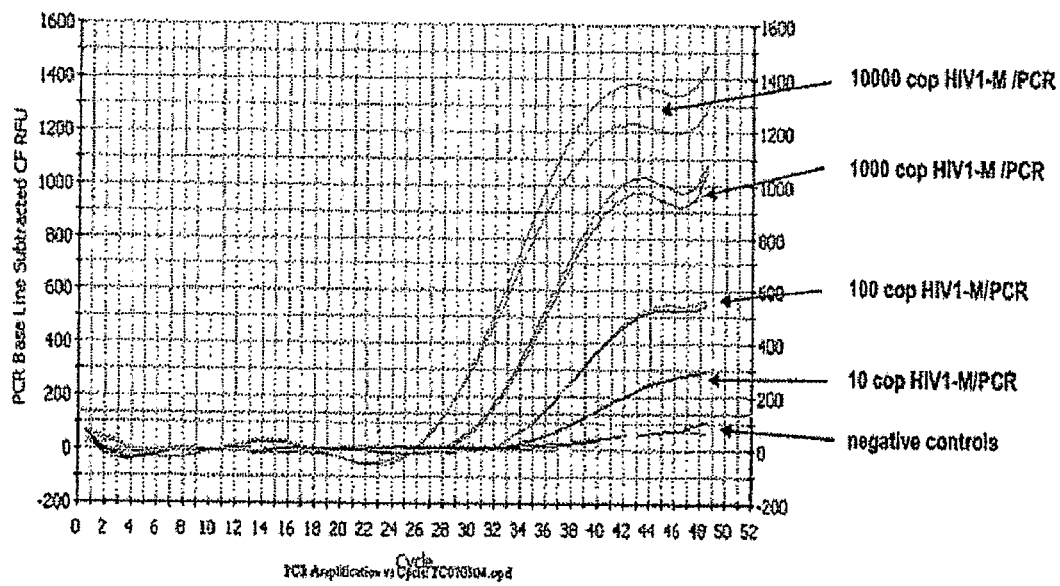
FIGURE 5A : HIV1-M target with 10000 cop, 1000, 100 and 10 cop/PCR and negative controls
FAM DETECTION
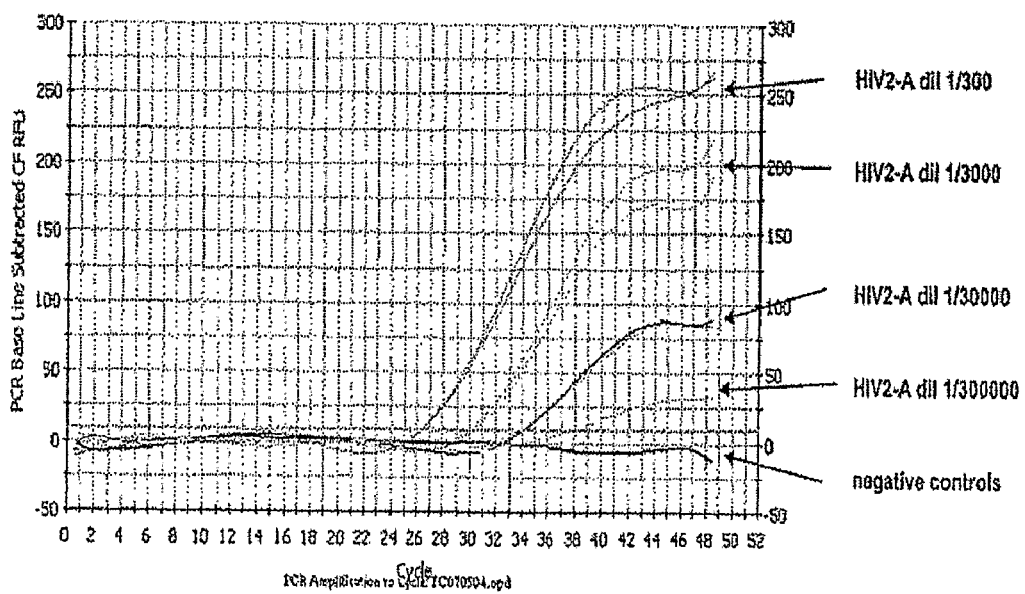
FIGURE 5B : HIV2-A target dil 1/300, 1/3000, 1/30000 and 1/300000 and negative controls
ROX DETECTION FIGURE 6A : Experiment a) with HIV2 target dil 1/300, 1/3000, 1/30000
ROX DETECTION
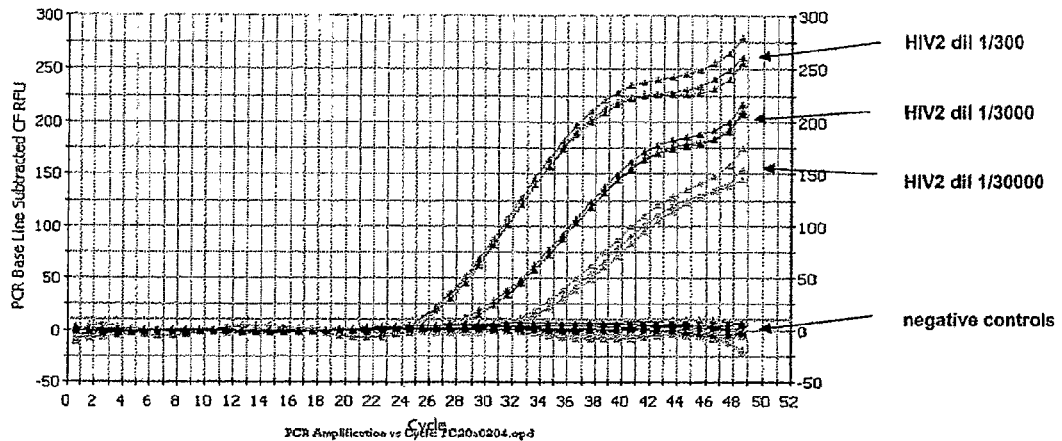
FIGURE 6B : Experiment b) with HIV2 target dil 1/300, 1/3000, 1/30000 + IC $10^6$ cop/PCR
ROX DETECTION
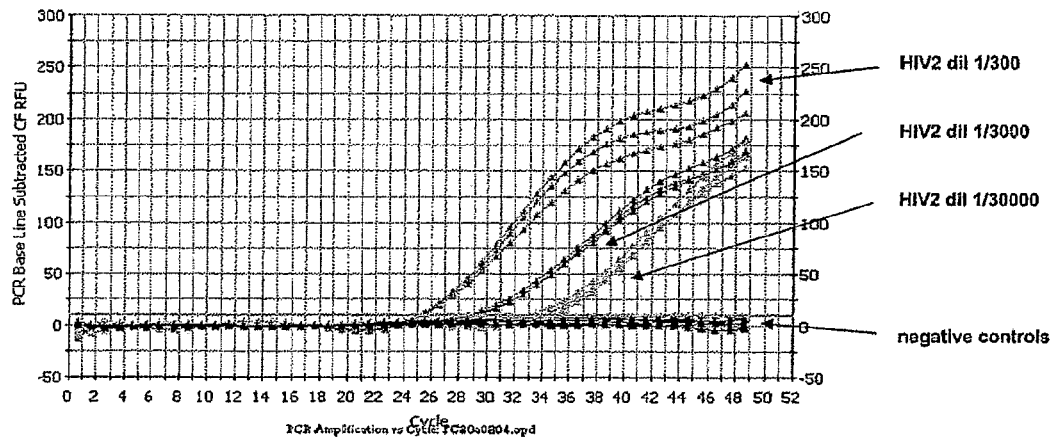
FIGURE 6C : Experiment b) with IC $10^6$ cop/PCR + HIV2 target dil 1/300, 1/3000, 1/30000
TAMRA DETECTION
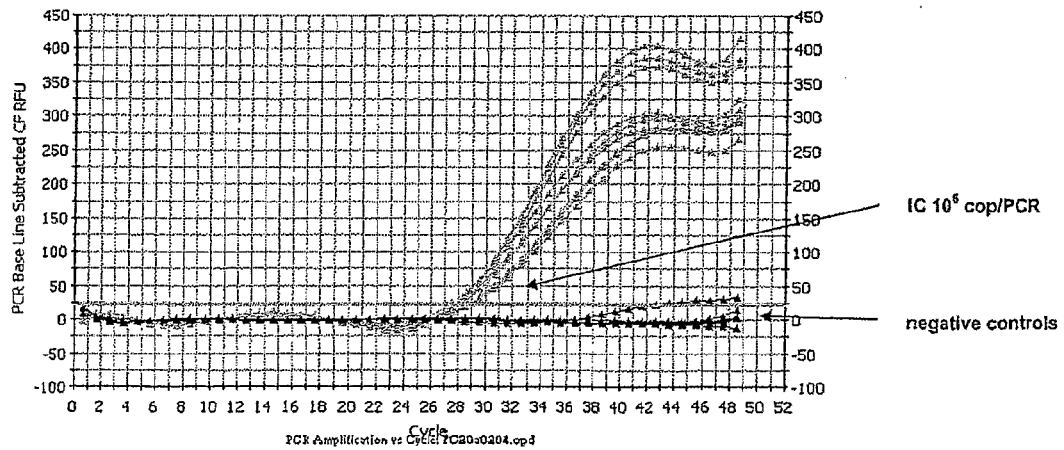

| SEQ ID No. | Name | 5' to 3' sequence | Preferred function | comment | positions |
|---|---|---|---|---|---|
| 1 | | ggagg aaatgaacaa gtagataaat tagtcagtgc tggaatcagg aaagtactat ttttagatgg aatagataag gcccaagatg aacatgagaa atatcacagt aattggagag caatggctag tgattttaac ctgccacctg tagtagcaaa agaaatagta gccagctgtg ataaatgtca gctaaaagga gaagccatgc atggacaagt agactgtagt ccaggaatat ggcaactaga ttgtacacat ttagaa | HIV1-M amplicon | | 4176 - 4436 |
| 2 | | aattggagag caatggctag tgattttaac ctgccacctg tagtagcaaa agaaatagta gccagctgtg ataaatgtca gctaaaagga gaagccatgc atggacaagt agactgtagt ccaggaatat ggcaactaga ttgtacacat ttagaa | HIV1-M amplicon | | 4281 - 4436 |
| 3 | | ggaggaaatg aaaaaataga taaattagta agcaaggata ttagaagagt cctgttccta gaaggaatag accaggcaca agaagatcat gaaaaatatc atagtaattg gaaagcacta gctagtgaat ttgactacc accagtggtg gccaaggaagc aattcatggt caggtagact tgtcatataa aagggaagc aattcatggt caggtagact atagattgca cacatgga a | HIV1-O amplicon | | 4231 - 4491 |
| 4 | | aattg gaaagcacta gctagtgaat ttgactacc accagtggtg gccaaggaaa tcattgctag ctgtcctaaa tgtcatataa aagggaagc aattcatggt caggtagact gcagtccaga agtatgcaa atagattgca cacatgga a | HIV1-O amplicon | | 4336 - 4491 |
| 5 | | a ggaaggcaga cagcactctt cctattaaaa ctggccagta ggtggccaat aacgcactig cacacagaca atggccccaa cttcacttca caggaagtga agatggtggc atggtgggta ggtatagaac aatcctttgg agtacc | HIV2 amplicon | | 4889 - 5036 |
| 305 | | ggagg aaatgaacaa gtagataaat tagtcagtgc tggaatcagg aaagtactat ttttagatgg aatagataag gcccaagatg aacatgagaa atatcacagt aattggagag caatggctag tgattttaac ctgccacctg tagtagcaaa agaaatagta gccagctgtg ataaatgtca gctaaaagga gaagccatgc atggacaagt agactgtagt ccaggaatat ggcaactaga ttgtacaca | HIV1-M amplicon | | 4176-4429 |

FIGURE 7

| | | | |
|---|---|---|---|
| 306 | aattggagag caatggctag tgatttaac ctgccacctg tagtagcaaa agaaatagta gccagctgtg ataaatgtca gctaaaagga gaagccatgc atggacaagt agactgtagt ccaggaatat ggcaactaga ttgtacaca | HIV1-M amplicon | 4281-4429 |
| 307 | ttggagag caatggctag tgatttaac ctgccacctg tagtagcaaa agaaatagta gccagctgtg ataaatgtca gctaaaagga gaagccatgc atggacaagt agactgtagt ccaggaatat ggcaactaga ttgtacaca | HIV1-M amplicon | 4283-4429 |
| 308 | ttggagag caatggctag tgatttaac ctgccacctg tagtagcaaa agaaatagta gccagctgtg ataaatgtca gctaaaagga gaagccatgc atggacaagt agactgtagt ccaggaatat ggcaactaga ttgtacacat t | HIV1-M amplicon | 4283-4431 |
| 309 | ggaggaaatg aaaaaataga taaattagta agcaaggata ttagaagagt cctgttccta gaaggaatag accaggcaca agaagatcat gaaaaatatc atagtaattg gaaagcacta gctagtgaat ttggactacc accagtggtg gccaaggaagc aattcatggt caggtagact gcagtccaga agtaggcaa atagattgca caca | HIV1-O amplicon | 4231-4484 |
| 310 | aattg gaaagcacta gctagtgaat ttggactacc accagtggtg gccaaggaagc aattcatggt caggtagact gcagtccaga agtatggcaa atagattgca caca | HIV1-O amplicon | 4336-4484 |
| 311 | ttg gaaagcacta gctagtgaat ttggactacc accagtggtg gccaaggaagc aattcatggt caggtagact gcagtccaga agtatggcaa atagattgca caca | HIV1-O amplicon | 4338-4484 |

FIGURE 7 (end)

| SEQ ID No. | Name | 5' to 3' sequence | Preferred function | comment | positions |
|---|---|---|---|---|---|
| 6 | H1B1f | GGAGGAAATGAACAAGTAGATAAA | HIV1-M forward primer | | 4176 - 4199 |
| 7 | H1B4f | TTGGAGAGCAATGGCTAGTGA | HIV1-M forward primer | | 4283 - 4303 |
| 8 | H1B25f | TTGGAGAGCAATGGCTAATGA | HIV1-M forward primer | | 4283 - 4303 |
| 9 | | TTGGAGAGCAATGGCTARTGA | HIV1-M forward primer | d | 4283 - 4303 |
| 10 | H1B11f | AATTGGAGAGCAATGGCTAGTGA | HIV1-M forward primer | e | 4281 - 4303 |
| 11 | H1B13f | AATTGGAGAGCAATGGCTAATGA | HIV1-M forward primer | e | 4281 - 4303 |
| 12 | | AATTGGAGAGCAATGGCTARTGA | HIV1-M forward primer | d | 4281 - 4303 |
| 13 | H1B14f | AATTGGAGAGCAATGGCTAITGA | HIV1-M forward primer | e, i | 4281 - 4303 |
| 14 | H1B12f | TCACTAATTGGAGAGCAATGGCTAAGTGA | HIV1-M forward primer | e, l | 4281 - 4303 |
| 15 | | TCATTAATTGGAGAGCAATGGCTAAATGA | HIV1-M forward primer | e, l | 4281 - 4303 |

FIGURE 8

| SEQ ID No. | Name | 5' to 3' sequence | Preferred function | comment | positions |
|---|---|---|---|---|---|
| 16 | H1B10r | TGTGTGCAATCTAGTTGCCATA | HIV1-M reverse primer | | 4429 - 4408 |
| 17 | H1B32r | TGTGTACAATCTAATTGCCATA | HIV1-M reverse primer | | 4429 - 4408 |
| 18 | H1B33r | TGTGTACAATCTAGTTGCCATA | HIV1-M reverse primer | | 4429 - 4408 |
| 19 | | TGTGTGCAATCTAATTGCCATA | HIV1-M reverse primer | | 4429 - 4408 |
| 20 | | TGTGTRCAATCTAGTTGCCATA | HIV1-M reverse primer | d | 4429 - 4408 |
| 21 | | TGTGTGCAATCTARTTGCCATA | HIV1-M reverse primer | d | 4429 - 4408 |
| 22 | | TGTGTRCAATCTAATTGCCATA | HIV1-M reverse primer | d | 4429 - 4408 |
| 23 | | TGTGTACAATCTARTTGCCATA | HIV1-M reverse primer | d | 4429 - 4408 |
| 24 | | TGTGTRCAATCTARTTGCCATA | HIV1-M reverse primer | d | 4429 - 4408 |
| 25 | H1B16r | AATGTGTGCAATCTAGTTGCCATA | HIV1-M reverse primer | e | 4431 - 4408 |
| 26 | H1B19r | TTCTAAATGTGTACAATCTAGTTGCCATA | HIV1-M reverse primer | e | 4436 - 4408 |
| 27 | H1B20r | TTCTAAATGTGTACAATCTAATTGCCATA | HIV1-M reverse primer | e | 4436 - 4408 |
| 28 | | TTCTAAATGTGTGCAATCTAATTGCCATA | HIV1-M reverse primer | e | 4436 - 4408 |
| 29 | | TTCTAAATGTGTGCAATCTAGTTGCCATA | HIV1-M reverse primer | e | 4436 - 4408 |
| 30 | | TTCTAAATGTGTRCAATCTAGTTGCCATA | HIV1-M reverse primer | d, e | 4436 - 4408 |
| 31 | | TTCTAAATGTGTGCAATCTARTTGCCATA | HIV1-M reverse primer | d, e | 4436 - 4408 |
| 32 | | TTCTAAATGTGTRCAATCTAATTGCCATA | HIV1-M reverse primer | d, e | 4436 - 4408 |
| 33 | | TTCTAAATGTGTACAATCTARTTGCCATA | HIV1-M reverse primer | d, e | 4436 - 4408 |
| 34 | | TTCTAAATGTGTRCAATCTARTTGCCATA | HIV1-M reverse primer | d, e | 4436 - 4408 |
| 35 | | TTCTAGATGTGTACAATCTAGTTGCCATA | HIV1-M reverse primer | e | 4436 - 4408 |
| 36 | | TTCTAGATGTGTACAATCTAATTGCCATA | HIV1-M reverse primer | e | 4436 - 4408 |
| 37 | | TTCTAGATGTGTGCAATCTAATTGCCATA | HIV1-M reverse primer | e | 4436 - 4408 |
| 38 | H1B22r | TTCTAGATGTGTGCAATCTAGTTGCCATA | HIV1-M reverse primer | e | 4436 - 4408 |
| 39 | | TTCTAGATGTGTRCAATCTAGTTGCCATA | HIV1-M reverse primer | d, e | 4436 - 4408 |
| 40 | | TTCTAGATGTGTGCAATCTARTTGCCATA | HIV1-M reverse primer | e | 4436 - 4408 |
| 41 | | TTCTAGATGTGTRCAATCTAATTGCCATA | HIV1-M reverse primer | d, e | 4436 - 4408 |
| 42 | | TTCTAGATGTGTACAATCTARTTGCCATA | HIV1-M reverse primer | d, e | 4436 - 4408 |
| 43 | | TTCTAGATGTGTRCAATCTARTTGCCATA | HIV1-M reverse primer | d, e | 4436 - 4408 |

FIGURE 9

| # | ID | Sequence | Description | Notes | Position |
|---|---|---|---|---|---|
| 44 | | TTCTARATGTGTACAATCTAGTTGCCATA | HIV1-M reverse primer | d, e | 4436 - 4408 |
| 45 | | TTCTARATGTGTACAATCTAATTGCCATA | HIV1-M reverse primer | d, e | 4436 - 4408 |
| 46 | | TTCTARATGTGTGCAATCTAATTGCCATA | HIV1-M reverse primer | d, e | 4436 - 4408 |
| 47 | | TTCTARATGTGTGCAATCTAGTTGCCATA | HIV1-M reverse primer | d, e | 4436 - 4408 |
| 48 | | TTGTARATGTGTGTRCAATCTAGTTGCCATA | HIV1-M reverse primer | d, e | 4436 - 4408 |
| 49 | | TTCTARATGTGTGCAATCTARTCTAATTGCCATA | HIV1-M reverse primer | d, e | 4436 - 4408 |
| 50 | | TTCTARATGTGTRCAATCTAATTGCCATA | HIV1-M reverse primer | d, e | 4436 - 4408 |
| 51 | | TTCTARATGTGTRCAATCTARTCTAATTGCCATA | HIV1-M reverse primer | d, e | 4436 - 4408 |
| 52 | | TTCTARATGTACAATCTARTTGCCATA | HIV1-M reverse primer | d, e | 4436 - 4408 |
| 53 | | TTCTARATGTGTRCAATCTARTTGCCATA | HIV1-M reverse primer | d, e | 4436 - 4408 |
| 54 | 534 | TGTGTTCAATCTATTGCCATA | HIV1-M reverse primer | i | 4429 - 4408 |
| 55 | 535 | AATGTGTTCAATCTATTGCCATA | HIV1-M reverse primer | e, i | 4431 - 4408 |
| 56 | H1B23r | TTCTAIATGTGTTCAATCTATTGCCATA | HIV1-M reverse primer | e, i | 4436 - 4408 |
| 57 | H1B21r | TATGGCTTCTAAATGTGTACAATCTAGTTGCCATA | HIV1-M reverse primer | e, i | 4436 - 4408 |
| 58 | | TATGGCTTCTAAATGTGTACAATCTAATTGCCATA | HIV1-M reverse primer | e, i | 4436 - 4408 |
| 59 | | TATGGCTTCTAAATGTGTRCAATCTARTTGCCATA | HIV1-M reverse primer | d, e, i | 4436 - 4408 |
| 60 | | TATGGCTTCTAAATGTGTGCAATCTAATTGCCATA | HIV1-M reverse primer | e, i | 4436 - 4408 |
| 61 | | TATGGCTTCTAAATGTGTGCAATCTAGTTGCCATA | HIV1-M reverse primer | e, i | 4436 - 4408 |
| 62 | | TATGGCTTCTAAATGTGTRCAATCTAGTTGCCATA | HIV1-M reverse primer | d, e, i | 4436 - 4408 |
| 63 | | TATGGCTTCTAAATGTGTRCAATCTARTCTAATTGCCATA | HIV1-M reverse primer | d, e, i | 4436 - 4408 |
| 64 | | TATGGCTTCTAAATGTGTACAATCTAGTTGCCATA | HIV1-M reverse primer | d, e, i | 4436 - 4408 |
| 65 | | TATGGCTTCTAGATGTGTACAATCTAGTTGCCATA | HIV1-M reverse primer | e, i | 4436 - 4408 |
| 66 | | TATGGCTTCTAGATGTGTACAATCTAATTGCCATA | HIV1-M reverse primer | e, i | 4436 - 4408 |
| 67 | | TATGGCTTCTAGATGTGTACAATCTARTTGCCATA | HIV1-M reverse primer | d, e, i | 4436 - 4408 |
| 68 | | TATGGCTTCTAGATGTGTGCAATCTAATTGCCATA | HIV1-M reverse primer | e, i | 4436 - 4408 |
| 69 | | TATGGCTTCTAGATGTGTGCAATCTAGTTGCCATA | HIV1-M reverse primer | e, i | 4436 - 4408 |
| 70 | | TATGGCTTCTAGATGTGTRCAATCTARTTGCCATA | HIV1-M reverse primer | d, e, i | 4436 - 4408 |
| 71 | | TATGGCTTCTAGATGTGTGCAATCTARTTGCCATA | HIV1-M reverse primer | d, e, i | 4436 - 4408 |
| 72 | | TATGGCTTCTAGATGTGTRCAATCTAATTGCCATA | HIV1-M reverse primer | d, e, i | 4436 - 4408 |
| 73 | | TATGGCTTCTAGATGTGTRCAATCTAGTTGCCATA | HIV1-M reverse primer | d, e, i | 4436 - 4408 |
| 74 | | TATGGCTTCTARATGTGTACAATCTAGTTGCCATA | HIV1-M reverse primer | d, e, i | 4436 - 4408 |

FIGURE 10

| | | | | |
|---|---|---|---|---|
| 75 | TATGGCTTCTARATGTGTACAATCTAATTGCCATA | HIV1-M reverse primer | d, e, l | 4436 - 4408 |
| 76 | TATGGCTTCTARATGTGTACAATCTARTTGCCATA | HIV1-M reverse primer | d, e, l | 4436 - 4408 |
| 77 | TATGGCTTCTARATGTGCAATCTAATTGCCATA | HIV1-M reverse primer | d, e, l | 4436 - 4408 |
| 78 | TATGGCTTCTARATGTGCAATCTAGTTGCCATA | HIV1-M reverse primer | d, e, l | 4436 - 4408 |
| 79 | TATGGCTTCTARATGTGCAATCTARTTGCCATA | HIV1-M reverse primer | d, e, l | 4436 - 4408 |
| 80 | TATGGCTTCTARATGTGTRCAATCTAGTTGCCATA | HIV1-M reverse primer | d, e, l | 4436 - 4408 |
| 81 | TATGGCTTCTARATGTGTRCAATCTAATTGCCATA | HIV1-M reverse primer | d, e, l | 4436 - 4408 |
| 82 | TATGGCTTCTARATGTGTRCAATCTARTTGCCATA | HIV1-M reverse primer | d, e, l | 4436 - 4408 |

FIGURE 11

| SEQ ID No. | Name | 5' to 3' sequence | Preferred function | comment | positions |
|---|---|---|---|---|---|
| 83 | | AAAGAAATAGTAGCCAGCTGTGATAAATGTC | HIV1-M probe | e | 4329 - 4359 |
| 84 | | AAAGAAATAGTGGCCAGCTGTGATAAATGTC | HIV1-M probe | e | 4329 - 4359 |
| 85 | | AAAGAAATAGTGGCTAGCTGTGATAAATGTC | HIV1-M probe | e | 4329 - 4359 |
| 86 | | AAAGAAATAGTAGCTAGCTGTGATAAATGTC | HIV1-M probe | e | 4329 - 4359 |
| 87 | | AAAGAAATAGTAGCYAGCTGTGATAAATGTC | HIV1-M probe | e | 4329 - 4359 |
| 88 | | AAAGAAATAGTRGCCAGCTGTGATAAATGTC | HIV1-M probe | d, e | 4329 - 4359 |
| 89 | | AAAGAAATAGTRGCTAGCTGTGATAAATGTC | HIV1-M probe | d, e | 4329 - 4359 |
| 90 | | AAAGAAATAGTGGCYAGCTGTGATAAATGTC | HIV1-M probe | d, e | 4329 - 4359 |
| 91 | | AAAGAAATAGTRGCYAGCTGTGATAAATGTC | HIV1-M probe | d, e | 4329 - 4359 |
| 92 | SH1BM4 | TGCGCAAAGAAATAGTAGCCAGCTGTGATAAATGTCGCGCA | HIV1-M probe | e, b | 4329 - 4359 |
| 93 | | TGCGCAAAGAAATAGTGGCCAGCTGTGATAAATGTCGCGCA | HIV1-M probe | e, b | 4329 - 4359 |
| 94 | | TGCGCAAAGAAATAGTGGCTAGCTGTGATAAATGTCGCGCA | HIV1-M probe | e, b | 4329 - 4359 |
| 95 | | TGCGCAAAGAAATAGTAGCTAGCTGTGATAAATGTCGCGCA | HIV1-M probe | e, b | 4329 - 4359 |
| 96 | | TGCGCAAAGAAATAGTAGCYAGCTGTGATAAATGTCGCGCA | HIV1-M probe | d, e, b | 4329 - 4359 |
| 97 | | TGCGCAAAGAAATAGTRGCCAGCTGTGATAAATGTCGCGCA | HIV1-M probe | d, e, b | 4329 - 4359 |
| 98 | | TGCGCAAAGAAATAGTRGCTAGCTGTGATAAATGTCGCGCA | HIV1-M probe | d, e, b | 4329 - 4359 |
| 99 | | TGCGCAAAGAAATAGTGGCYAGCTGTGATAAATGTCGCGCA | HIV1-M probe | d, e, b | 4329 - 4359 |
| 100 | | TGCGCAAAGAAATAGTRGCYAGCTGTGATAAATGTCGCGCA | HIV1-M probe | e, b | 4329 - 4359 |
| 101 | SH1BM12 | CGCGCAAAGAAATAGTAGCCAGCTGTGATAAATGTCGCGCG | HIV1-M probe | e, b | 4329 - 4359 |
| 102 | | CGCGCAAAGAAATAGTGGCCAGCTGTGATAAATGTCGCGCG | HIV1-M probe | e, b | 4329 - 4359 |
| 103 | | CGCGCAAAGAAATAGTGGCTAGCTGTGATAAATGTCGCGCG | HIV1-M probe | e, b | 4329 - 4359 |
| 104 | | CGCGCAAAGAAATAGTAGCTAGCTGTGATAAATGTCGCGCG | HIV1-M probe | e, b | 4329 - 4359 |
| 105 | | CGCGCAAAGAAATAGTRGCCAGCTGTGATAAATGTCGCGCG | HIV1-M probe | d, e, b | 4329 - 4359 |
| 106 | | CGCGCAAAGAAATAGTRGCTAGCTGTGATAAATGTCGCGCG | HIV1-M probe | d, e, b | 4329 - 4359 |
| 107 | | CGCGCAAAGAAATAGTGGCYAGCTGTGATAAATGTCGCGCG | HIV1-M probe | d, e, b | 4329 - 4359 |
| 108 | | CGCGCAAAGAAATAGTRGCYAGCTGTGATAAATGTCGCGCG | HIV1-M probe | d, e, b | 4329 - 4359 |
| 109 | | CGCGCAAAGAAATAGTRGCYAGCTGTGATAAATGTCGCGCG | HIV1-M probe | d, e, b | 4329 - 4359 |

FIGURE 12

| # | Name | Sequence | Type | Notes | Range |
|---|---|---|---|---|---|
| 110 | | ATAGTAGCCAGCTGTGATAAATGTC | HIV1-M probe | | 4335-4359 |
| 111 | | ATAGTAGCTAGCTGTGATAAATGTC | HIV1-M probe | | 4336-4359 |
| 112 | | ATAGTGGCCAGCTGTGATAAATGTC | HIV1-M probe | | 4335-4359 |
| 113 | | ATAGTGGCTAGCTGTGATAAATGTC | HIV1-M probe | | 4335-4359 |
| 114 | | ATAGTAGCYAGCTGTGATAAATGTC | HIV1-M probe | d | 4335-4359 |
| 115 | | ATAGTRGCCAGCTGTGATAAATGTC | HIV1-M probe | d | 4336-4359 |
| 116 | | ATAGTRGCTAGCTGTGATAAATGTC | HIV1-M probe | d | 4335-4359 |
| 117 | | ATAGTGGCYAGCTGTGATAAATGTC | HIV1-M probe | d | 4335-4359 |
| 118 | | ATAGTRGCYAGCTGTGATAAATGTC | HIV1-M probe | d | 4335-4359 |
| 119 | SH1BM5 | TGCGCATAGTAGCCAGCTGTGATAAATGTCGCGCA | HIV1-M probe | b | 4335-4359 |
| 120 | | TGCGCATAGTAGCTAGCTGTGATAAATGTCGCGCA | HIV1-M probe | b | 4335-4359 |
| 121 | | TGCGCATAGTGGCCAGCTGTGATAAATGTCGCGCA | HIV1-M probe | b | 4335-4359 |
| 122 | | TGCGCATAGTGGCTAGCTGTGATAAATGTCGCGCA | HIV1-M probe | b | 4335-4359 |
| 123 | | TGCGCATAGTAGCYAGCTGTGATAAATGTCGCGCA | HIV1-M probe | d, b | 4335-4359 |
| 124 | | TGCGCATAGTRGCCAGCTGTGATAAATGTCGCGCA | HIV1-M probe | d, b | 4335-4359 |
| 125 | | TGCGCATAGTRGCTAGCTGTGATAAATGTCGCGCA | HIV1-M probe | d, b | 4335-4359 |
| 126 | | TGCGCATAGTGGCYAGCTGTGATAAATGTCGCGCA | HIV1-M probe | d, b | 4335-4359 |
| 127 | | TGCGCATAGTRGCYAGCTGTGATAAATGTCGCGCA | HIV1-M probe | d, b | 4335-4359 |
| 128 | SH1BM10 | CGCGCATAGTAGCCAGCTGTGATAAATGTCGCGCG | HIV1-M probe | b | 4335-4359 |
| 129 | SH1BM13 | CGCGCATAGTAGCTAGCTGTGATAAATGTCGCGCG | HIV1-M probe | b | 4335-4359 |
| 130 | SH1BM14 | CGCGCATAGTGGCCAGCTGTGATAAATGTCGCGCG | HIV1-M probe | b | 4335-4359 |
| 131 | | CGCGCATAGTGGCTAGCTGTGATAAATGTCGCGCG | HIV1-M probe | b | 4335-4359 |
| 132 | | CGCGCATAGTAGCYAGCTGTGATAAATGTCGCGCG | HIV1-M probe | d, b | 4335-4359 |
| 133 | | CGCGCATAGTRGCCAGCTGTGATAAATGTCGCGCG | HIV1-M probe | d, b | 4335-4359 |
| 134 | | CGCGCATAGTRGCTAGCTGTGATAAATGTCGCGCG | HIV1-M probe | d, b | 4335-4359 |
| 135 | | CGCGCATAGTGGCYAGCTGTGATAAATGTCGCGCG | HIV1-M probe | d, b | 4335-4359 |
| 136 | | CGCGCATAGTRGCYAGCTGTGATAAATGTCGCGCG | HIV1-M probe | d, b | 4335-4359 |
| 137 | | ATAGTiGCiAGCTGTGATAAATGTC | HIV1-M probe | i | 4335-4359 |
| 138 | SH1BM15 | CGCGCATAGTiGCiAGCTGTGATAAATGTCGCGCG | HIV1-M probe | i, b | 4335-4359 |

FIGURE 13

| SEQ ID No. | Name | 5' to 3' sequence | Preferred function | comment | positions |
|---|---|---|---|---|---|
| 139 | H1B3f | GGAGGAAATGAAAAAATAGATAAA | HIV1-O forward primer | | 4231 - 4254 |
| 140 | H1B5f | TTGGAGAGCACTAGCTAGTGA | HIV1-O forward primer | | 4338 - 4358 |
| 141 | | TTGGAGAGCATTAGCTAGTGA | HIV1-O forward primer | | 4338 - 4358 |
| 142 | | TTGGAAAGCACTAGCTAGTGA | HIV1-O forward primer | | 4338 - 4358 |
| 143 | | TTGGAAAGCATTAGCTAGTGA | HIV1-O forward primer | | 4338 - 4358 |
| 144 | | TTGGAGAGCAYTAGCTAGTGA | HIV1-O forward primer | d | 4338 - 4358 |
| 145 | | TTGGAGARAGCACTAGCTAGTGA | HIV1-O forward primer | d | 4338 - 4358 |
| 146 | | TTGGAAAGCAYTAGCTAGTGA | HIV1-O forward primer | d | 4338 - 4358 |
| 147 | | TTGGARAGCATTAGCTAGTGA | HIV1-O forward primer | d | 4338 - 4358 |
| 148 | | TTGGARAGCAYTAGCTAGTGA | HIV1-O forward primer | d | 4338 - 4358 |
| 149 | H1B15f | AATTGGAGAGCATTAGCTAGTGA | HIV1-O forward primer | e | 4336 - 4358 |
| 150 | H1B16f | AATTGGAAAGCACTAGCTAGTGA | HIV1-O forward primer | e | 4336 - 4358 |
| 151 | H1B17f | AATTGGAAAGCATTAGCTAGTGA | HIV1-O forward primer | e | 4336 - 4358 |
| 152 | | AATTGGAGAGCACTAGCTAGTGA | HIV1-O forward primer | e | 4336 - 4358 |
| 153 | | AATTGGAGARAGCACTAGCTAGTGA | HIV1-O forward primer | d, e | 4336 - 4358 |
| 154 | | AATTGGAAAGCAYTAGCTAGTGA | HIV1-O forward primer | d, e | 4336 - 4358 |
| 155 | | AATTGGARAGCATTAGCTAGTGA | HIV1-O forward primer | d, e | 4336 - 4358 |
| 156 | | AATTGGARAGCAYTAGCTAGTGA | HIV1-O forward primer | d, e | 4336 - 4358 |
| 157 | | AATTGGARAGCAYTAGCTAGTGA | HIV1-O forward primer | d, e | 4336 - 4358 |
| 158 | H1B18f | AATTGGAiAGCAiTAGCTAGTGA | HIV1-O forward primer | e, i | 4336 - 4358 |
| 159 | | TCACTAATTGGAGAGCATTAGCTAGTGA | HIV1-O forward primer | e, l | 4336 - 4358 |
| 160 | | TCACTAATTGGAAAGCACTAGCTAGTGA | HIV1-O forward primer | e, l | 4336 - 4358 |
| 161 | | TCACTAATTGGAAAGCATTAGCTAGTGA | HIV1-O forward primer | e, l | 4336 - 4358 |
| 162 | | TCACTAATTGGAGAGCACTAGCTAGTGA | HIV1-O forward primer | e, l | 4336 - 4358 |
| 163 | | TCACTAATTGGAGARAGCACTAGCTAGTGA | HIV1-O forward primer | d, e, l | 4336 - 4358 |
| 164 | | TCACTAATTGGAAAGCAYTAGCTAGTGA | HIV1-O forward primer | d, e, l | 4336 - 4358 |
| 165 | | TCACTAATTGGARAGCATTAGCTAGTGA | HIV1-O forward primer | d, e, l | 4336 - 4358 |
| 166 | | TCACTAATTGGARAGCAYTAGCTAGTGA | HIV1-O forward primer | d, e, l | 4336 - 4358 |
| 167 | | TCACTAATTGGARAGCAYTAGCTAGTGA | HIV1-O forward primer | d, e, l | 4336 - 4358 |

FIGURE 14

| SEQ ID No. | Name | 5' to 3' sequence | Preferred function | comment | positions |
|---|---|---|---|---|---|
| 168 | H1B13r | TGTGTGCAATCTATATTGCCATA | HIV1-O reverse primer | | 4484 - 4463 |
| 169 | | TGTGTACAATCTATTTGCCATA | HIV1-O reverse primer | | 4484 - 4463 |
| 170 | | TGTGTRCAATCTATTTGCCATA | HIV1-O reverse primer | | 4484 - 4463 |
| 171 | H1B24r | TTCTAAAATGTGTACAATCTATTTGCCATA | HIV1-O reverse primer | e | 4491 - 4463 |
| 172 | H1B25r | TTCTAGATGTGTGCAATCTATTTGCCATA | HIV1-O reverse primer | e | 4491 - 4463 |
| 173 | | TTCTAAATGTGTGCAATCTATTTGCCATA | HIV1-O reverse primer | e | 4491 - 4463 |
| 174 | | TTCTAGATGTGTACAATCTATTTGCCATA | HIV1-O reverse primer | e | 4491 - 4463 |
| 175 | | TTCTARATGTGTGCAATCTATTTGCCATA | HIV1-O reverse primer | d, e | 4491 - 4463 |
| 176 | | TTCTARATGTGTRCAATCTATTTGCCATA | HIV1-O reverse primer | d, e | 4491 - 4463 |
| 177 | | TTCTAAATGTGTRCAATCTATTTGCCATA | HIV1-O reverse primer | d, e | 4491 - 4463 |
| 178 | | TTCTAGATGTGTRCAATCTATTTGCCATA | HIV1-O reverse primer | d, e | 4491 - 4463 |
| 179 | | TTCTARATGTGTRCAATCTATTTGCCATA | HIV1-O reverse primer | e | 4491 - 4463 |
| 180 | H1B26r | TTCTAIATGTGTICAATCTATTTGCCATA | HIV1-O reverse primer | e, i | 4491 - 4463 |
| 181 | | TATGGCTTCTAAAATGTGTACAATCTATTTGCCATA | HIV1-O reverse primer | e, l | 4491 - 4463 |
| 182 | | TATGGCTTCTAGATGTGTGCAATCTATTTGCCATA | HIV1-O reverse primer | e, l | 4491 - 4463 |
| 183 | | TATGGCTTCTAAATGTGTGCAATCTATTTGCCATA | HIV1-O reverse primer | e, l | 4491 - 4463 |
| 184 | | TATGGCTTCTAGATGTGTACAATCTATTTGCCATA | HIV1-O reverse primer | e, l | 4491 - 4463 |
| 185 | | TATGGCTTCTARATGTGTGCAATCTATTTGCCATA | HIV1-O reverse primer | d, e, l | 4491 - 4463 |
| 186 | | TATGGCTTCTARATGTGTRCAATCTATTTGCCATA | HIV1-O reverse primer | d, e, l | 4491 - 4463 |
| 187 | | TATGGCTTCTAAATGTGTRCAATCTATTTGCCATA | HIV1-O reverse primer | d, e, l | 4491 - 4463 |
| 188 | | TATGGCTTCTAGATGTGTRCAATCTATTTGCCATA | HIV1-O reverse primer | d, e, l | 4491 - 4463 |
| 189 | | TATGGCTTCTARATGTGTRCAATCTATTTGCCATA | HIV1-O reverse primer | d, e, l | 4491 - 4463 |

FIGURE 15

| SEQ ID No. | Name | 5' to 3' sequence | Preferred function | comment | positions |
|---|---|---|---|---|---|
| 190 | | GAAATCATTGCTAGTTGTCCTAAATGTCATAT | HIV1-O probe | | 4387 - 4417 |
| 191 | SH1B02 | TGCGCGAAATCATTGCTAGTTGTCCTAAATGTCATATGCGCA | HIV1-O probe | b | 4387 - 4417 |
| 192 | SH1B07 | CGGCGAAATCATTGCTAGTTGTCCTAAATGTCATATGCGCG | HIV1-O probe | b | 4387 - 4417 |
| 193 | | AGTCTACCTGACCATGAATTGCTTCCCTTTTA | HIV1-O probe | | 4449 - 4417 |
| 194 | SH1B010 | CGGCGAAGTCTACCTGACCATGAATTGCTTCCCCTTTTATGCGCG | HIV1-O probe | b | 4449 - 4417 |

FIGURE 16

| SEQ ID No. | Name | 5' to 3' sequence | Preferred function | comment | positions |
|---|---|---|---|---|---|
| 195 | H2A3f | AGGAAGRCARACAGCACTCTTC | HIV2 forward primer | d | 4889 - 4913 |
| 196 | H2A9f | AGGAAGGCAAACAGCACTCTTC | HIV2 forward primer | c | 4889 - 4913 |
| 197 | | AGGAAGACARACAGCACTCTTC | HIV2 forward primer | d | 4889 - 4913 |
| 198 | | AGGAAGGCARACAGCACTCTTC | HIV2 forward primer | d | 4889 - 4913 |
| 199 | | AGGAAGACAAACAGCACTCTTC | HIV2 forward primer | | 4889 - 4913 |
| 200 | | AGGAAGGCAGACAGCACTCTTC | HIV2 forward primer | | 4889 - 4913 |
| 201 | | AGGAAGACAGACAGCACTCTTC | HIV2 forward primer | | 4889 - 4913 |
| 202 | | AGGAAGRCAAACAGCACTCTTC | HIV2 forward primer | d | 4889 - 4913 |
| 203 | | AGGAAGRCAGACAGCACTCTTC | HIV2 forward primer | d | 4889 - 4913 |
| 204 | H2A10f | AGGAAGACAGACAGCTCTCTTC | HIV2 forward primer | c | 4889 - 4913 |
| 205 | | AGGAAGRCARACAGCTCTCTTC | HIV2 forward primer | d | 4889 - 4913 |
| 206 | | AGGAAGACAAACAGCTCTCTTC | HIV2 forward primer | | 4889 - 4913 |
| 207 | | AGGAAGGCAGACAGCTCTCTTC | HIV2 forward primer | | 4889 - 4913 |
| 208 | | AGGAAGGCAAACAGCTCTCTTC | HIV2 forward primer | | 4889 - 4913 |
| 209 | | AGGAAGRCAGACAGCTCTCTTC | HIV2 forward primer | d | 4889 - 4913 |
| 210 | | AGGAAGRCAAACAGCTCTCTTC | HIV2 forward primer | d | 4889 - 4913 |
| 211 | | AGGAAGACARACAGCTCTCTTC | HIV2 forward primer | d | 4889 - 4913 |
| 212 | | AGGAAGGCARACAGCTCTCTTC | HIV2 forward primer | d | 4889 - 4913 |
| 213 | | AGGAAGGCACAAACAGCWCTCTTC | HIV2 forward primer | | 4889 - 4913 |
| 214 | | AGGAAGACAGACAGCWCTCTTC | HIV2 forward primer | | 4889 - 4913 |
| 215 | | AGGAAGACAAACAGCWCTCTTC | HIV2 forward primer | | 4889 - 4913 |
| 216 | | AGGAAGGCAAACAGCWCTCTTC | HIV2 forward primer | | 4889 - 4913 |
| 217 | | AGGAAGRCAGACAGCWCTCTTC | HIV2 forward primer | d | 4889 - 4913 |
| 218 | | AGGAAGRCAAACAGCWCTCTTC | HIV2 forward primer | d | 4889 - 4913 |
| 219 | | AGGAAGACARACAGCWCTCTTC | HIV2 forward primer | d | 4889 - 4913 |
| 220 | | AGGAAGGCARACAGCWCTCTTC | HIV2 forward primer | d | 4889 - 4913 |
| 221 | | AGGAAGRCARACAGCWCTCTTC | HIV2 forward primer | d | 4889 - 4913 |
| 222 | 539 | CAGGAAGRCAIACAGCICTCTTCCT | HIV2 forward primer | e, i | 4888 - 4915 |

FIGURE 17

| | | | | |
|---|---|---|---|---|
| 223 | H2A7f | GAAGAGAGAGGAAGRCARACAGCACTCTTC | HIV2 forward primer | d, l | 4889 - 4913 |
| 224 | | GAAGAGAGGAAGAGGAAGACAAACAGCACTCTTC | HIV2 forward primer | l | 4889 - 4913 |
| 225 | | GAAGAGAGGAAGAGGAAGGCAGACAGCACTCTTC | HIV2 forward primer | l | 4889 - 4913 |
| 226 | | GAAGAGAGGAAGAGGAAGGCAAACAGCACTCTTC | HIV2 forward primer | l | 4889 - 4913 |
| 227 | | GAAGAGAGGAAGAGGAAGACACAGCACTCTTC | HIV2 forward primer | l | 4889 - 4913 |
| 228 | | GAAGAGAGGAAGAGGAAGACARACAGCACTCTTC | HIV2 forward primer | d, l | 4889 - 4913 |
| 229 | | GAAGAGAGGAAGAGGAAGGCARACAGCACTCTTC | HIV2 forward primer | d, l | 4889 - 4913 |
| 230 | | GAAGAGAGGAAGAGGAAGRCAAACAGCACTCTTC | HIV2 forward primer | d, l | 4889 - 4913 |
| 231 | | GAAGAGAGGAAGAGGAAGRCAGACAGCACTCTTC | HIV2 forward primer | d, l | 4889 - 4913 |
| 232 | | GAAGAGAGGAAGAGGAAGRCARACAGCTCTCTTC | HIV2 forward primer | l | 4889 - 4913 |
| 233 | | GAAGAGAGGAAGAGGAAGACAAACAGCTCTCTTC | HIV2 forward primer | l | 4889 - 4913 |
| 234 | | GAAGAGAGGAAGAGGAAGGCAGACAGCTCTCTTC | HIV2 forward primer | l | 4889 - 4913 |
| 235 | | GAAGAGAGGAAGAGGAAGGCAAACAGCTCTCTTC | HIV2 forward primer | l | 4889 - 4913 |
| 236 | | GAAGAGAGGAAGAGGAAGACACAGCTCTCTTC | HIV2 forward primer | l | 4889 - 4913 |
| 237 | | GAAGAGAGGAAGAGGAAGACARACAGCTCTCTTC | HIV2 forward primer | d, l | 4889 - 4913 |
| 238 | | GAAGAGAGGAAGAGGAAGGCARACAGCTCTCTTC | HIV2 forward primer | d, l | 4889 - 4913 |
| 239 | | GAAGAGAGGAAGAGGAAGRCAAACAGCTCTCTTC | HIV2 forward primer | d, l | 4889 - 4913 |
| 240 | | GAAGAGAGGAAGAGGAAGRCAGACAGCTCTCTTC | HIV2 forward primer | d, l | 4889 - 4913 |
| 241 | | GAAGAGAGGAAGAGGAAGACAAACAGCWCTCTTC | HIV2 forward primer | d, l | 4889 - 4913 |
| 242 | | GAAGAGAGGAAGAGGAAGGCAGACAGCWCTCTTC | HIV2 forward primer | d, l | 4889 - 4913 |
| 243 | | GAAGAGAGGAAGAGGAAGGCAAACAGCWCTCTTC | HIV2 forward primer | d, l | 4889 - 4913 |
| 244 | | GAAGAGAGGAAGAGGAAGACAGACAGCWCTCTTC | HIV2 forward primer | d, l | 4889 - 4913 |
| 245 | | GAAGAGAGGAAGAGGAAGACARACAGCWCTCTTC | HIV2 forward primer | d, l | 4889 - 4913 |
| 246 | | GAAGAGAGGAAGAGGAAGGCARACAGCWCTCTTC | HIV2 forward primer | d, l | 4889 - 4913 |
| 247 | | GAAGAGAGGAAGAGGAAGRCAAACAGCWCTCTTC | HIV2 forward primer | d, l | 4889 - 4913 |
| 248 | | GAAGAGAGGAAGAGGAAGRCAGACAGCWCTCTTC | HIV2 forward primer | d, l | 4889 - 4913 |
| 249 | | GAAGAGAGGAAGAGGAAGRCARACAGCWCTCTTC | HIV2 forward primer | d, l | 4889 - 4913 |

FIGURE 18

| SEQ ID No. | Name | 5' to 3' sequence | Preferred function | comment | positions |
|---|---|---|---|---|---|
| 250 | H2A3r | GGTACTCCRAAGGTTTGTTCTAT | HIV2 reverse primer | d | 5036 - 5014 |
| 251 | | GGTACTCCRAAGGATTGTTCTAT | HIV2 reverse primer | d | 5036 - 5014 |
| 252 | | GGTACTCCRAAGGTTTGCTCTAT | HIV2 reverse primer | d | 5036 - 5014 |
| 253 | | GGTACTCCRAAGGATTGCTCTAT | HIV2 reverse primer | d | 5036 - 5014 |
| 254 | | GGTACTCCRAAGGWTTGCTCTAT | HIV2 reverse primer | d | 5036 - 5014 |
| 255 | | GGTACTCCRAAGGWTTGTTCTAT | HIV2 reverse primer | d | 5036 - 5014 |
| 256 | | GGTACTCCRAAGGATTGYTCTAT | HIV2 reverse primer | d | 5036 - 5014 |
| 257 | | GGTACTCCRAAGGTTTGYTCTAT | HIV2 reverse primer | d | 5036 - 5014 |
| 258 | H2A8r | GGTACTCCCAAAGGATTGCTCTAT | HIV2 reverse primer | d | 5036 - 5014 |
| 259 | | GGTACTCCAAAGGWTGCTCTAT | HIV2 reverse primer | c | 5036 - 5014 |
| 260 | | GGTACTCCAAAGGWTGTTCTAT | HIV2 reverse primer | d | 5036 - 5014 |
| 261 | | GGTACTCCAAAGGWTTGYTCTAT | HIV2 reverse primer | d | 5036 - 5014 |
| 262 | | GGTACTCCAAAGGATTGYTCTAT | HIV2 reverse primer | d | 5036 - 5014 |
| 263 | | GGTACTCCAAAGGTTTGYTCTAT | HIV2 reverse primer | d | 5036 - 5014 |
| 264 | | GGTACTCCAAAGGTTTGTTCTAT | HIV2 reverse primer | | 5036 - 5014 |
| 265 | | GGTACTCCAAAGGATTGTTCTAT | HIV2 reverse primer | | 5036 - 5014 |
| 266 | | GGTACTCCAAAGGTTTGCTCTAT | HIV2 reverse primer | | 5036 - 5014 |
| 267 | H2A9r | GGTACTCCGAAGGTTTGTTCTAT | HIV2 reverse primer | c | 5036 - 5014 |
| 268 | | GGTACTCCGAAGGATTGTTCTAT | HIV2 reverse primer | | 5036 - 5014 |
| 269 | | GGTACTCCGAAGGTTTGCTCTAT | HIV2 reverse primer | | 5036 - 5014 |
| 270 | | GGTACTCCGAAGGATTGCTCTAT | HIV2 reverse primer | | 5036 - 5014 |
| 271 | | GGTACTCCGAAGGWTTGCTCTAT | HIV2 reverse primer | d | 5036 - 5014 |
| 272 | | GGTACTCCGAAGGWTTGTTCTAT | HIV2 reverse primer | d | 5036 - 5014 |
| 273 | | GGTACTCCGAAGGWTTGYTCTAT | HIV2 reverse primer | d | 5036 - 5014 |
| 274 | | GGTACTCCGAAGGATTGYTCTAT | HIV2 reverse primer | d | 5036 - 5014 |
| 275 | | GGTACTCCGAAGGTTTGYTCTAT | HIV2 reverse primer | d | 5036 - 5014 |
| 276 | | GGTACTCCRAAGGWTTGYTCTAT | HIV2 reverse primer | d | 5036 - 5014 |
| 277 | H2A10r | GGTACTCCIAAGGITTGITCTAT | HIV2 reverse primer | i | 5036 - 5014 |

FIGURE 19

| | | | | | |
|---|---|---|---|---|---|
| 278 | n° 538 | GGTACTCCIAAGGITTGTTCTAT | HIV2 reverse primer | i | 5036 - 5014 |
| 279 | H2A7r | ATAGAACGGTACTCCRAAGGTTTGTTCTAT | HIV2 reverse primer | d, l | 5036 - 5014 |
| 280 | | ATAGAACGGTACTCCGAAGGTTTGTTCTAT | HIV2 reverse primer | l | 5036 - 5014 |
| 281 | | ATAGAACGGTACTCCRAAGGATTGTTCTAT | HIV2 reverse primer | d, l | 5036 - 5014 |
| 282 | | ATAGAACGGTACTCCAAAGGWTTGTTCTAT | HIV2 reverse primer | d, l | 5036 - 5014 |
| 283 | | ATAGAACGGTACTCCAAAGGTTTGTTCTAT | HIV2 reverse primer | l | 5036 - 5014 |
| 284 | | ATAGAACGGTACTCCAAAGGATTGTTCTAT | HIV2 reverse primer | l | 5036 - 5014 |
| 285 | | ATAGAACGGTACTCCGAAGGATTGTTCTAT | HIV2 reverse primer | l | 5036 - 5014 |
| 286 | | ATAGAACGGTACTCCGAAGGWTTGTTCTAT | HIV2 reverse primer | d, l | 5036 - 5014 |
| 287 | | ATAGAACGGTACTCCRAAGGWTTGTTCTAT | HIV2 reverse primer | d, l | 5036 - 5014 |
| 288 | | ATAGAGCGGTACTCCRAAGGTTTGCTCTAT | HIV2 reverse primer | d, l | 5036 - 5014 |
| 289 | | ATAGAGCGGTACTCCRAAGGATTGCTCTAT | HIV2 reverse primer | d, l | 5036 - 5014 |
| 290 | | ATAGAGCGGTACTCCAAAGGATTGCTCTAT | HIV2 reverse primer | l | 5036 - 5014 |
| 291 | | ATAGAGCGGTACTCCAAAGGWTTGCTCTAT | HIV2 reverse primer | d, l | 5036 - 5014 |
| 292 | | ATAGAGCGGTACTCCAAAGGTTTGCTCTAT | HIV2 reverse primer | l | 5036 - 5014 |
| 293 | | ATAGAGCGGTACTCCGAAGGTTTGCTCTAT | HIV2 reverse primer | l | 5036 - 5014 |
| 294 | | ATAGAGCGGTACTCCGAAGGATTGCTCTAT | HIV2 reverse primer | l | 5036 - 5014 |
| 295 | | ATAGAGCGGTACTCCGAAGGWTTGCTCTAT | HIV2 reverse primer | d, l | 5036 - 5014 |
| 296 | | ATAGAGCGGTACTCCRAAGGWTTGCTCTAT | HIV2 reverse primer | d, l | 5036 - 5014 |

FIGURE 20

| SEQ ID No. | Name | 5' to 3' sequence | Preferred function | comment | positions |
|---|---|---|---|---|---|
| 297 | | GGCCAATAACACACTTGCACACA | HIV2-A probe | | 4932 - 4956 |
| 298 | SH2A9a | AGCGCGGCCAATAACACACTTGCACACAGCGCT | HIV2-A probe | b | 4932 - 4956 |
| 299 | SH2A14a | CGCGCGGCCAATAACACACTTGCACACAGCGCG | HIV2-A probe | b | 4932 - 4956 |
| 300 | | GCCTATCACACACCTGCACACA | HIV2-B probe | | 4933 - 4956 |
| 301 | SH2A1b | AGCGCGCCTATCACACACCTGCACACAGCGCT | HIV2-B probe | b | 4933 - 4956 |
| 302 | SH2A2b | CGCGCGCCTATCACACACCTGCACACAGCGCG | HIV2-B probe | b | 4933 - 4956 |
| 303 | SH2A3b | CCGCGGCCTATCACACACCTGCACACAGCGGG | HIV2-B probe | b | 4933 - 4956 |
| 304 | SH2AB | CGCGCGGCCiATiACACACiTGCACACAGCGCG | HIV2 probe | i | 4932 - 4956 |

FIGURE 21

```
                         SEQUENCE LISTING

<160> NUMBER OF SEQ ID NOS: 311

<210> SEQ ID NO 1
<211> LENGTH: 261
<212> TYPE: DNA
<213> ORGANISM: Human immunodeficiency virus

<400> SEQUENCE: 1
ggaggaaatg aacaagtaga taaattagtc agtgctggaa tcaggaaagt actattttta      60 gatgaatag ataaggccca agatgaacat gagaaatatc acagtaattg gagagcaatg      120
gctagtgatt ttaacctgcc acctgtagta gcaaaagaaa tagtagccag ctgtgataaa    180
tgtcagctaa aaggagaagc catgcatgga caagtagact gtagtccagg aatatggcaa    240
ctagattgta cacatttaga a                                              261

<210> SEQ ID NO 2
<211> LENGTH: 156
<212> TYPE: DNA
<213> ORGANISM: Human immunodeficiency virus

<400> SEQUENCE: 2
aattggagag caatggctag tgattttaac ctgccacctg tagtagcaaa agaaatagta      60
gccagctgtg ataaatgtca gctaaaagga gaagccatgc atggacaagt agactgtagt    120
ccaggaatat ggcaactaga ttgtacacat ttagaa                              156

<210> SEQ ID NO 3
<211> LENGTH: 261
<212> TYPE: DNA
<213> ORGANISM: Human immunodeficiency virus

<400> SEQUENCE: 3
ggaggaaatg aaaaaataga taaattagta agcaaggata ttagaagagt cctgttccta      60
gaaggaatag accaggcaca agaagatcat gaaaaatatc atagtaattg gaaagcacta    120
gctagtgaat ttggactacc accagtggtg gccaaggaaa tcattgctag ctgtcctaaa    180
tgtcatataa aaggggaagc aattcatggt caggtagact gcagtccaga agtatggcaa    240
atagattgca cacatatgga a                                              261

<210> SEQ ID NO 4
<211> LENGTH: 156
<212> TYPE: DNA
<213> ORGANISM: Human immunodeficiency virus

<400> SEQUENCE: 4
aattggaaag cactagctag tgaatttgga ctaccaccag tggtggccaa ggaaatcatt      60
gctagctgtc ctaaatgtca tataaaaggg gaagcaattc atggtcaggt agactgcagt    120
ccagaagtat ggcaaataga ttgcacacat atggaa                              156
```

```
<210> SEQ ID NO 5
<211> LENGTH: 147
<212> TYPE: DNA
<213> ORGANISM: Human immunodeficiency virus

<400> SEQUENCE: 5
aggaaggcag acagcactct tcctattaaa actggccagt aggtggccaa taacgcactt      60
gcacacagac aatggcccca acttcacttc acaggaagtg aagatggtgg catggtgggt     120
aggtatagaa caatcctttg gagtacc                                         147

<210> SEQ ID NO 6
<211> LENGTH: 24
<212> TYPE: DNA
<213> ORGANISM: Artificial Sequence
<220> FEATURE:
<223> OTHER INFORMATION: synthetic oligonucleotide for detection

<400> SEQUENCE: 6
ggaggaaatg aacaagtaga taaa                                            24

<210> SEQ ID NO 7
<211> LENGTH: 21
<212> TYPE: DNA
<213> ORGANISM: Artificial Sequence
<220> FEATURE:
<223> OTHER INFORMATION: synthetic oligonucleotide for detection

<400> SEQUENCE: 7
ttggagagca atggctagtg a                                               21

<210> SEQ ID NO 8
<211> LENGTH: 21
<212> TYPE: DNA
<213> ORGANISM: Artificial Sequence
<220> FEATURE:
<223> OTHER INFORMATION: synthetic oligonucleotide for detection

<400> SEQUENCE: 8
ttggagagca atggctaatg a                                               21

<210> SEQ ID NO 9
<211> LENGTH: 21
<212> TYPE: DNA
<213> ORGANISM: Artificial Sequence
<220> FEATURE:
<223> OTHER INFORMATION: synthetic oligonucleotide for detection

<400> SEQUENCE: 9
ttggagagca atggctartg a                                               21

<210> SEQ ID NO 10
<211> LENGTH: 23
<212> TYPE: DNA
<213> ORGANISM: Artificial sequence
<220> FEATURE:
<223> OTHER INFORMATION: synthetic oligonucleotide for detection

<400> SEQUENCE: 10
aattggagag caatggctag tga                                             23

<210> SEQ ID NO 11
<211> LENGTH: 23
<212> TYPE: DNA
<213> ORGANISM: Artificial Sequence
<220> FEATURE:
<223> OTHER INFORMATION: synthetic oligonucleotide for detection
```

```
<400> SEQUENCE: 11
aattggagag caatggctaa tga                                     23

<210> SEQ ID NO 12
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 12
aattggagag caatggctar tga                                     23

<210> SEQ ID NO 13
<211> LENGTH: 23
<212> TYPE: DNA
<213> ORGANISM: Artificial Sequence
<220> FEATURE:
<223> OTHER INFORMATION: synthetic oligonucleotide for detection
<220> FEATURE:
<221> NAME/KEY: misc_feature
<222> LOCATION: (20)..(20)
<223> OTHER INFORMATION: n is inosine (i)

<400> SEQUENCE: 13
aattggagag caatggctan tga                                     23

<210> SEQ ID NO 14
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 14
tcactaattg gagagcaatg gctagtga                                28

<210> SEQ ID NO 15
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 15
tcattaattg gagagcaatg gctaatga                                28

<210> SEQ ID NO 16
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 16
tgtgtgcaat ctagttgcca ta                                      22

<210> SEQ ID NO 17
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 17
tgtgtacaat ctaattgcca ta                                      22
```

<210> SEQ ID NO 18
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 18
tgtgtacaat ctagttgcca ta                                              22

<210> SEQ ID NO 19
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 19
tgtgtgcaat ctaattgcca ta                                              22

<210> SEQ ID NO 20
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 20
tgtgtrcaat ctagttgcca ta                                              22

<210> SEQ ID NO 21
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 21
tgtgtgcaat ctarttgcca ta                                              22

<210> SEQ ID NO 22
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 22
tgtgtrcaat ctaattgcca ta                                              22

<210> SEQ ID NO 23
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 23
tgtgtacaat ctarttgcca ta                                              22

<210> SEQ ID NO 24
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 24
tgtgtrcaat ctarttgcca ta                                    22

<210> SEQ ID NO 25
<211> LENGTH: 24
<212> TYPE: DNA
<213> ORGANISM: Artificial Sequence
<220> FEATURE:
<223> OTHER INFORMATION: synthetic oligonucleotide for detection

<400> SEQUENCE: 25
aatgtgtgca atctagttgc cata                                  24

<210> SEQ ID NO 26
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 26
ttctaaatgt gtacaatcta gttgccata                             29

<210> SEQ ID NO 27
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 27
ttctaaatgt gtacaatcta attgccata                             29

<210> SEQ ID NO 28
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 28
ttctaaatgt gtgcaatcta attgccata                             29

<210> SEQ ID NO 29
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 29
ttctaaatgt gtgcaatcta gttgccata                             29

<210> SEQ ID NO 30
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 30
ttctaaatgt gtrcaatcta gttgccata                             29

<210> SEQ ID NO 31
<211> LENGTH: 29

```
<212> TYPE: DNA
<213> ORGANISM: Artificial Sequence
<220> FEATURE:
<223> OTHER INFORMATION: synthetic oligonucleotide for detection

<400> SEQUENCE: 31
ttctaaatgt gtgcaatcta rttgccata                                              29

<210> SEQ ID NO 32
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 32
ttctaaatgt gtrcaatcta attgccata                                              29

<210> SEQ ID NO 33
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 33
ttctaaatgt gtacaatcta rttgccata                                              29

<210> SEQ ID NO 34
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 34
ttctaaatgt gtrcaatcta rttgccata                                              29

<210> SEQ ID NO 35
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 35
ttctagatgt gtacaatcta gttgccata                                              29

<210> SEQ ID NO 36
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 36
ttctagatgt gtacaatcta attgccata                                              29

<210> SEQ ID NO 37
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 37
ttctagatgt gtgcaatcta attgccata                                              29
```

<210> SEQ ID NO 38
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 38
ttctagatgt gtgcaatcta gttgccata                                29

<210> SEQ ID NO 39
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 39
ttctagatgt gtrcaatcta gttgccata                                29

<210> SEQ ID NO 40
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 40
ttctagatgt gtgcaatcta rttgccata                                29

<210> SEQ ID NO 41
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 41
ttctagatgt gtrcaatcta attgccata                                29

<210> SEQ ID NO 42
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 42
ttctagatgt gtacaatcta rttgccata                                29

<210> SEQ ID NO 43
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 43
ttctagatgt gtrcaatcta rttgccata                                29

<210> SEQ ID NO 44
<211> LENGTH: 29
<212> TYPE: DNA
<213> ORGANISM: Artificial Sequence
<220> FEATURE:
<223> OTHER INFORMATION: synthetic oligonucleotide for detection

```
<400> SEQUENCE: 44
ttctaratgt gtacaatcta gttgccata                                              29

<210> SEQ ID NO 45
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 45
ttctaratgt gtacaatcta attgccata                                              29

<210> SEQ ID NO 46
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 46
ttctaratgt gtgcaatcta attgccata                                              29

<210> SEQ ID NO 47
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 47
ttctaratgt gtgcaatcta gttgccata                                              29

<210> SEQ ID NO 48
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 48
ttctaratgt gtrcaatcta gttgccata                                              29

<210> SEQ ID NO 49
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 49
ttctaratgt gtgcaatcta rttgccata                                              29

<210> SEQ ID NO 50
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 50
ttctaratgt gtrcaatcta attgccata                                              29

<210> SEQ ID NO 51
<211> LENGTH: 29
```

```
<212> TYPE: DNA
<213> ORGANISM: Artificial Sequence
<220> FEATURE:
<223> OTHER INFORMATION: synthetic oligonucleotide for detection

<400> SEQUENCE: 51
ttctaratgt gtacaatcta rttgccata                                29

<210> SEQ ID NO 52
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 52
ttctaratgt gtrcaatcta rttgccata                                29

<210> SEQ ID NO 53
<211> LENGTH: 22
<212> TYPE: DNA
<213> ORGANISM: Artificial Sequence
<220> FEATURE:
<223> OTHER INFORMATION: synthetic oligonucleotide for detection
<220> FEATURE:
<221> NAME/KEY: misc_feature
<222> LOCATION: (6)..(6)
<223> OTHER INFORMATION: n is inosine (i)
<220> FEATURE:
<221> NAME/KEY: misc_feature
<222> LOCATION: (14)..(14)
<223> OTHER INFORMATION: n is inosine (i)

<400> SEQUENCE: 53
tgtgtncaat ctanttgcca ta                                       22

<210> SEQ ID NO 54
<211> LENGTH: 24
<212> TYPE: DNA
<213> ORGANISM: Artificial Sequence
<220> FEATURE:
<223> OTHER INFORMATION: synthetic oligonucleotide for detection
<220> FEATURE:
<221> NAME/KEY: misc_feature
<222> LOCATION: (8)..(8)
<223> OTHER INFORMATION: n is inosine (i)
<220> FEATURE:
<221> NAME/KEY: misc_feature
<222> LOCATION: (16)..(16)
<223> OTHER INFORMATION: n is inosine (i)

<400> SEQUENCE: 54
aatgtgtnca atctanttgc cata                                     24

<210> SEQ ID NO 55
<211> LENGTH: 29
<212> TYPE: DNA
<213> ORGANISM: Artificial Sequence
<220> FEATURE:
<223> OTHER INFORMATION: synthetic oligonucleotide for detection
<220> FEATURE:
<221> NAME/KEY: misc_feature
<222> LOCATION: (6)..(6)
<223> OTHER INFORMATION: n is inosine (i)
<220> FEATURE:
<221> NAME/KEY: misc_feature
<222> LOCATION: (13)..(13)
<223> OTHER INFORMATION: n is inosine (i)
<220> FEATURE:
<221> NAME/KEY: misc_feature
<222> LOCATION: (21)..(21)
<223> OTHER INFORMATION: n is inosine (i)
```

```
<400> SEQUENCE: 55
ttctanatgt gtncaatcta nttgccata                                    29

<210> SEQ ID NO 56
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 56
tatggcttct aaatgtgtac aatctagttg ccata                             35

<210> SEQ ID NO 57
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 57
tatggcttct aaatgtgtac aatctaattg ccata                             35

<210> SEQ ID NO 58
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 58
tatggcttct aaatgtgtac aatctarttg ccata                             35

<210> SEQ ID NO 59
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 59
tatggcttct aaatgtgtgc aatctaattg ccata                             35

<210> SEQ ID NO 60
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 60
tatggcttct aaatgtgtgc aatctagttg ccata                             35

<210> SEQ ID NO 61
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 61
tatggcttct aaatgtgtgc aatctarttg ccata                             35

<210> SEQ ID NO 62
<211> LENGTH: 35
```

<212> TYPE: DNA
<213> ORGANISM: Artificial Sequence
<220> FEATURE:
<223> OTHER INFORMATION: synthetic oligonucleotide for detection

<400> SEQUENCE: 62
tatggcttct aaatgtgtrc aatctagttg ccata                              35

<210> SEQ ID NO 63
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 63
tatggcttct aaatgtgtrc aatctarttg ccata                              35

<210> SEQ ID NO 64
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 64
tatggcttct aaatgtgtrc aatctaattg ccata                              35

<210> SEQ ID NO 65
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 65
tatggcttct agatgtgtac aatctagttg ccata                              35

<210> SEQ ID NO 66
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 66
tatggcttct agatgtgtac aatctaattg ccata                              35

<210> SEQ ID NO 67
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 67
tatggcttct agatgtgtac aatctarttg ccata                              35

<210> SEQ ID NO 68
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 68
tatggcttct agatgtgtgc aatctaattg ccata                              35

<210> SEQ ID NO 69
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 69
tatggcttct agatgtgtgc aatctagttg ccata                        35

<210> SEQ ID NO 70
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 70
tatggcttct agatgtgtgc aatctarttg ccata                        35

<210> SEQ ID NO 71
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 71
tatggcttct agatgtgtrc aatctagttg ccata                        35

<210> SEQ ID NO 72
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 72
tatggcttct agatgtgtrc aatctarttg ccata                        35

<210> SEQ ID NO 73
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 73
tatggcttct agatgtgtrc aatctaattg ccata                        35

<210> SEQ ID NO 74
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 74
tatggcttct aratgtgtac aatctagttg ccata                        35

<210> SEQ ID NO 75
<211> LENGTH: 35
<212> TYPE: DNA
<213> ORGANISM: Artificial Sequence
<220> FEATURE:
<223> OTHER INFORMATION: synthetic oligonucleotide for detection

```
<400> SEQUENCE: 75
tatggcttct aratgtgtac aatctaattg ccata                    35

<210> SEQ ID NO 76
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 76
tatggcttct aratgtgtac aatctarttg ccata                    35

<210> SEQ ID NO 77
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 77
tatggcttct aratgtgtgc aatctaattg ccata                    35

<210> SEQ ID NO 78
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 78
tatggcttct aratgtgtgc aatctagttg ccata                    35

<210> SEQ ID NO 79
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 79
tatggcttct aratgtgtgc aatctarttg ccata                    35

<210> SEQ ID NO 80
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 80
tatggcttct aratgtgtrc aatctagttg ccata                    35

<210> SEQ ID NO 81
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 81
tatggcttct aratgtgtrc aatctaattg ccata                    35

<210> SEQ ID NO 82
<211> LENGTH: 35
```

```
<212> TYPE: DNA
<213> ORGANISM: Artificial Sequence
<220> FEATURE:
<223> OTHER INFORMATION: synthetic oligonucleotide for detection

<400> SEQUENCE: 82
tatggcttct aratgtgtrc aatctarttg ccata                         35

<210> SEQ ID NO 83
<211> LENGTH: 31
<212> TYPE: DNA
<213> ORGANISM: Artificial Sequence
<220> FEATURE:
<223> OTHER INFORMATION: synthetic oligonucleotide for detection

<400> SEQUENCE: 83
aaagaaatag tagccagctg tgataaatgt c                             31

<210> SEQ ID NO 84
<211> LENGTH: 31
<212> TYPE: DNA
<213> ORGANISM: Artificial Sequence
<220> FEATURE:
<223> OTHER INFORMATION: synthetic oligonucleotide for detection

<400> SEQUENCE: 84
aaagaaatag tggccagctg tgataaatgt c                             31

<210> SEQ ID NO 85
<211> LENGTH: 31
<212> TYPE: DNA
<213> ORGANISM: Artificial Sequence
<220> FEATURE:
<223> OTHER INFORMATION: synthetic oligonucleotide for detection

<400> SEQUENCE: 85
aaagaaatag tggctagctg tgataaatgt c                             31

<210> SEQ ID NO 86
<211> LENGTH: 31
<212> TYPE: DNA
<213> ORGANISM: Artificial Sequence
<220> FEATURE:
<223> OTHER INFORMATION: synthetic oligonucleotide for detection

<400> SEQUENCE: 86
aaagaaatag tagctagctg tgataaatgt c                             31

<210> SEQ ID NO 87
<211> LENGTH: 31
<212> TYPE: DNA
<213> ORGANISM: Artificial Sequence
<220> FEATURE:
<223> OTHER INFORMATION: synthetic oligonucleotide for detection

<400> SEQUENCE: 87
aaagaaatag tagcyagctg tgataaatgt c                             31

<210> SEQ ID NO 88
<211> LENGTH: 31
<212> TYPE: DNA
<213> ORGANISM: Artificial Sequence
<220> FEATURE:
<223> OTHER INFORMATION: synthetic oligonucleotide for detection

<400> SEQUENCE: 88
aaagaaatag trgccagctg tgataaatgt c                             31
```

<210> SEQ ID NO 89
<211> LENGTH: 31
<212> TYPE: DNA
<213> ORGANISM: Artificial Sequence
<220> FEATURE:
<223> OTHER INFORMATION: synthetic oligonucleotide for detection

<400> SEQUENCE: 89
aaagaaatag trgctagctg tgataaatgt c                              31

<210> SEQ ID NO 90
<211> LENGTH: 31
<212> TYPE: DNA
<213> ORGANISM: Artificial Sequence
<220> FEATURE:
<223> OTHER INFORMATION: synthetic oligonucleotide for detection

<400> SEQUENCE: 90
aaagaaatag tggcyagctg tgataaatgt c                              31

<210> SEQ ID NO 91
<211> LENGTH: 31
<212> TYPE: DNA
<213> ORGANISM: Artificial Sequence
<220> FEATURE:
<223> OTHER INFORMATION: synthetic oligonucleotide for detection

<400> SEQUENCE: 91
aaagaaatag trgcyagctg tgataaatgt c                              31

<210> SEQ ID NO 92
<211> LENGTH: 41
<212> TYPE: DNA
<213> ORGANISM: Artificial Sequence
<220> FEATURE:
<223> OTHER INFORMATION: synthetic oligonucleotide for detection

<400> SEQUENCE: 92
tgcgcaaaga aatagtagcc agctgtgata aatgtcgcgc a                   41

<210> SEQ ID NO 93
<211> LENGTH: 41
<212> TYPE: DNA
<213> ORGANISM: Artificial Sequence
<220> FEATURE:
<223> OTHER INFORMATION: synthetic oligonucleotide for detection

<400> SEQUENCE: 93
tgcgcaaaga aatagtggcc agctgtgata aatgtcgcgc a                   41

<210> SEQ ID NO 94
<211> LENGTH: 41
<212> TYPE: DNA
<213> ORGANISM: Artificial Sequence
<220> FEATURE:
<223> OTHER INFORMATION: synthetic oligonucleotide for detection

<400> SEQUENCE: 94
tgcgcaaaga aatagtggct agctgtgata aatgtcgcgc a                   41

<210> SEQ ID NO 95
<211> LENGTH: 41
<212> TYPE: DNA
<213> ORGANISM: Artificial Sequence
<220> FEATURE:
<223> OTHER INFORMATION: synthetic oligonucleotide for detection

<400> SEQUENCE: 95
tgcgcaaaga aatagtagct agctgtgata aatgtcgcgc a                              41

<210> SEQ ID NO 96
<211> LENGTH: 41
<212> TYPE: DNA
<213> ORGANISM: Artificial Sequence
<220> FEATURE:
<223> OTHER INFORMATION: synthetic oligonucleotide for detection

<400> SEQUENCE: 96
tgcgcaaaga aatagtagcy agctgtgata aatgtcgcgc a                              41

<210> SEQ ID NO 97
<211> LENGTH: 41
<212> TYPE: DNA
<213> ORGANISM: Artificial Sequence
<220> FEATURE:
<223> OTHER INFORMATION: synthetic oligonucleotide for detection

<400> SEQUENCE: 97
tgcgcaaaga aatagtrgcc agctgtgata aatgtcgcgc a                              41

<210> SEQ ID NO 98
<211> LENGTH: 41
<212> TYPE: DNA
<213> ORGANISM: Artificial Sequence
<220> FEATURE:
<223> OTHER INFORMATION: synthetic oligonucleotide for detection

<400> SEQUENCE: 98
tgcgcaaaga aatagtrgct agctgtgata aatgtcgcgc a                              41

<210> SEQ ID NO 99
<211> LENGTH: 41
<212> TYPE: DNA
<213> ORGANISM: Artificial Sequence
<220> FEATURE:
<223> OTHER INFORMATION: synthetic oligonucleotide for detection

<400> SEQUENCE: 99
tgcgcaaaga aatagtggcy agctgtgata aatgtcgcgc a                              41

<210> SEQ ID NO 100
<211> LENGTH: 41
<212> TYPE: DNA
<213> ORGANISM: Artificial Sequence
<220> FEATURE:
<223> OTHER INFORMATION: synthetic oligonucleotide for detection

<400> SEQUENCE: 100
tgcgcaaaga aatagtrgcy agctgtgata aatgtcgcgc a                              41

<210> SEQ ID NO 101
<211> LENGTH: 41
<212> TYPE: DNA
<213> ORGANISM: Artificial Sequence
<220> FEATURE:
<223> OTHER INFORMATION: synthetic oligonucleotide for detection

<400> SEQUENCE: 101
cgcgcaaaga aatagtagcc agctgtgata aatgtcgcgc g                              41

<210> SEQ ID NO 102
<211> LENGTH: 41

```
<212> TYPE: DNA
<213> ORGANISM: Artificial Sequence
<220> FEATURE:
<223> OTHER INFORMATION: synthetic oligonucleotide for detection

<400> SEQUENCE: 102
cgcgcaaaga aatagtggcc agctgtgata aatgtcgcgc g                    41

<210> SEQ ID NO 103
<211> LENGTH: 41
<212> TYPE: DNA
<213> ORGANISM: Artificial Sequence
<220> FEATURE:
<223> OTHER INFORMATION: synthetic oligonucleotide for detection

<400> SEQUENCE: 103
cgcgcaaaga aatagtggct agctgtgata aatgtcgcgc g                    41

<210> SEQ ID NO 104
<211> LENGTH: 41
<212> TYPE: DNA
<213> ORGANISM: Artificial Sequence
<220> FEATURE:
<223> OTHER INFORMATION: synthetic oligonucleotide for detection

<400> SEQUENCE: 104
cgcgcaaaga aatagtagct agctgtgata aatgtcgcgc g                    41

<210> SEQ ID NO 105
<211> LENGTH: 41
<212> TYPE: DNA
<213> ORGANISM: Artificial Sequence
<220> FEATURE:
<223> OTHER INFORMATION: synthetic oligonucleotide for detection

<400> SEQUENCE: 105
cgcgcaaaga aatagtrgcc agctgtgata aatgtcgcgc g                    41

<210> SEQ ID NO 106
<211> LENGTH: 41
<212> TYPE: DNA
<213> ORGANISM: Artificial Sequence
<220> FEATURE:
<223> OTHER INFORMATION: synthetic oligonucleotide for detection

<400> SEQUENCE: 106
cgcgcaaaga aatagtrgct agctgtgata aatgtcgcgc g                    41

<210> SEQ ID NO 107
<211> LENGTH: 41
<212> TYPE: DNA
<213> ORGANISM: Artificial Sequence
<220> FEATURE:
<223> OTHER INFORMATION: synthetic oligonucleotide for detection

<400> SEQUENCE: 107
cgcgcaaaga aatagtggcy agctgtgata aatgtcgcgc g                    41

<210> SEQ ID NO 108
<211> LENGTH: 41
<212> TYPE: DNA
<213> ORGANISM: Artificial Sequence
<220> FEATURE:
<223> OTHER INFORMATION: synthetic oligonucleotide for detection

<400> SEQUENCE: 108
cgcgcaaaga aatagtrgcy agctgtgata aatgtcgcgc g                    41
```

<210> SEQ ID NO 109
<211> LENGTH: 41
<212> TYPE: DNA
<213> ORGANISM: Artificial Sequence
<220> FEATURE:
<223> OTHER INFORMATION: synthetic oligonucleotide for detection

<400> SEQUENCE: 109
cgcgcaaaga aatagtrgcy agctgtgata aatgtcgcgc g            41

<210> SEQ ID NO 110
<211> LENGTH: 25
<212> TYPE: DNA
<213> ORGANISM: Artificial Sequence
<220> FEATURE:
<223> OTHER INFORMATION: synthetic oligonucleotide for detection

<400> SEQUENCE: 110
atagtagcca gctgtgataa atgtc                              25

<210> SEQ ID NO 111
<211> LENGTH: 25
<212> TYPE: DNA
<213> ORGANISM: Artificial Sequence
<220> FEATURE:
<223> OTHER INFORMATION: synthetic oligonucleotide for detection

<400> SEQUENCE: 111
atagtagcta gctgtgataa atgtc                              25

<210> SEQ ID NO 112
<211> LENGTH: 25
<212> TYPE: DNA
<213> ORGANISM: Artificial Sequence
<220> FEATURE:
<223> OTHER INFORMATION: synthetic oligonucleotide for detection

<400> SEQUENCE: 112
atagtggcca gctgtgataa atgtc                              25

<210> SEQ ID NO 113
<211> LENGTH: 25
<212> TYPE: DNA
<213> ORGANISM: Artificial Sequence
<220> FEATURE:
<223> OTHER INFORMATION: synthetic oligonucleotide for detection

<400> SEQUENCE: 113
atagtggcta gctgtgataa atgtc                              25

<210> SEQ ID NO 114
<211> LENGTH: 25
<212> TYPE: DNA
<213> ORGANISM: Artificial Sequence
<220> FEATURE:
<223> OTHER INFORMATION: synthetic oligonucleotide for detection

<400> SEQUENCE: 114
atagtagcya gctgtgataa atgtc                              25

<210> SEQ ID NO 115
<211> LENGTH: 25
<212> TYPE: DNA
<213> ORGANISM: Artificial Sequence
<220> FEATURE:
<223> OTHER INFORMATION: synthetic oligonucleotide for detection

```
<400> SEQUENCE: 115
atagtrgcca gctgtgataa atgtc                                      25

<210> SEQ ID NO 116
<211> LENGTH: 25
<212> TYPE: DNA
<213> ORGANISM: Artificial Sequence
<220> FEATURE:
<223> OTHER INFORMATION: synthetic oligonucleotide for detection

<400> SEQUENCE: 116
atagtrgcta gctgtgataa atgtc                                      25

<210> SEQ ID NO 117
<211> LENGTH: 25
<212> TYPE: DNA
<213> ORGANISM: Artificial Sequence
<220> FEATURE:
<223> OTHER INFORMATION: synthetic oligonucleotide for detection

<400> SEQUENCE: 117
atagtggcya gctgtgataa atgtc                                      25

<210> SEQ ID NO 118
<211> LENGTH: 25
<212> TYPE: DNA
<213> ORGANISM: Artificial Sequence
<220> FEATURE:
<223> OTHER INFORMATION: synthetic oligonucleotide for detection

<400> SEQUENCE: 118
atagtrgcya gctgtgataa atgtc                                      25

<210> SEQ ID NO 119
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 119
tgcgcatagt agccagctgt gataaatgtc gcgca                           35

<210> SEQ ID NO 120
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 120
tgcgcatagt agctagctgt gataaatgtc gcgca                           35

<210> SEQ ID NO 121
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 121
tgcgcatagt ggccagctgt gataaatgtc gcgca                           35

<210> SEQ ID NO 122
<211> LENGTH: 35
```

```
<212> TYPE: DNA
<213> ORGANISM: Artificial Sequence
<220> FEATURE:
<223> OTHER INFORMATION: synthetic oligonucleotide for detection

<400> SEQUENCE: 122
tgcgcatagt ggctagctgt gataaatgtc gcgca                        35

<210> SEQ ID NO 123
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 123
tgcgcatagt agcyagctgt gataaatgtc gcgca                        35

<210> SEQ ID NO 124
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 124
tgcgcatagt rgccagctgt gataaatgtc gcgca                        35

<210> SEQ ID NO 125
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 125
tgcgcatagt rgctagctgt gataaatgtc gcgca                        35

<210> SEQ ID NO 126
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 126
tgcgcatagt ggcyagctgt gataaatgtc gcgca                        35

<210> SEQ ID NO 127
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 127
tgcgcatagt rgcyagctgt gataaatgtc gcgca                        35

<210> SEQ ID NO 128
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 128
cgcgcatagt agccagctgt gataaatgtc gcgcg                        35
```

<210> SEQ ID NO 129
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 129
cgcgcatagt agctagctgt gataaatgtc gcgcg                                    35

<210> SEQ ID NO 130
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 130
cgcgcatagt ggccagctgt gataaatgtc gcgcg                                    35

<210> SEQ ID NO 131
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 131
cgcgcatagt ggctagctgt gataaatgtc gcgcg                                    35

<210> SEQ ID NO 132
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 132
cgcgcatagt agcyagctgt gataaatgtc gcgcg                                    35

<210> SEQ ID NO 133
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 133
cgcgcatagt rgccagctgt gataaatgtc gcgcg                                    35

<210> SEQ ID NO 134
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 134
cgcgcatagt rgctagctgt gataaatgtc gcgcg                                    35

<210> SEQ ID NO 135
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 135
cgcgcatagt ggcyagctgt gataaatgtc gcgcg                                35

<210> SEQ ID NO 136
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 136
cgcgcatagt rgcyagctgt gataaatgtc gcgcg                                35

<210> SEQ ID NO 137
<211> LENGTH: 25
<212> TYPE: DNA
<213> ORGANISM: Artificial Sequence
<220> FEATURE:
<223> OTHER INFORMATION: synthetic oligonucleotide for detection
<220> FEATURE:
<221> NAME/KEY: misc_feature
<222> LOCATION: (6)..(6)
<223> OTHER INFORMATION: n is inosine (i)
<220> FEATURE:
<221> NAME/KEY: misc_feature
<222> LOCATION: (9)..(9)
<223> OTHER INFORMATION: n is inosine (i)

<400> SEQUENCE: 137
atagtngcna gctgtgataa atgtc                                           25

<210> SEQ ID NO 138
<211> LENGTH: 35
<212> TYPE: DNA
<213> ORGANISM: Artificial Sequence
<220> FEATURE:
<223> OTHER INFORMATION: synthetic oligonucleotide for detection
<220> FEATURE:
<221> NAME/KEY: misc_feature
<222> LOCATION: (11)..(11)
<223> OTHER INFORMATION: n is inosine (i)
<220> FEATURE:
<221> NAME/KEY: misc_feature
<222> LOCATION: (14)..(14)
<223> OTHER INFORMATION: n is inosine (i)

<400> SEQUENCE: 138
cgcgcatagt ngcnagctgt gataaatgtc gcgcg                                35

<210> SEQ ID NO 139
<211> LENGTH: 24
<212> TYPE: DNA
<213> ORGANISM: Artificial Sequence
<220> FEATURE:
<223> OTHER INFORMATION: synthetic oligonucleotide for detection

<400> SEQUENCE: 139
ggaggaaatg aaaaaataga taaa                                            24

<210> SEQ ID NO 140
<211> LENGTH: 21
<212> TYPE: DNA
<213> ORGANISM: Artificial Sequence
<220> FEATURE:
<223> OTHER INFORMATION: synthetic oligonucleotide for detection

<400> SEQUENCE: 140
ttggagagca ctagctagtg a                                               21

<210> SEQ ID NO 141
<211> LENGTH: 21
<212> TYPE: DNA
<213> ORGANISM: Artificial Sequence
<220> FEATURE:
<223> OTHER INFORMATION: synthetic oligonucleotide for detection

<400> SEQUENCE: 141
ttggagagca ttagctagtg a                                              21

<210> SEQ ID NO 142
<211> LENGTH: 21
<212> TYPE: DNA
<213> ORGANISM: Artificial Sequence
<220> FEATURE:
<223> OTHER INFORMATION: synthetic oligonucleotide for detection

<400> SEQUENCE: 142
ttggaaagca ctagctagtg a                                              21

<210> SEQ ID NO 143
<211> LENGTH: 21
<212> TYPE: DNA
<213> ORGANISM: Artificial Sequence
<220> FEATURE:
<223> OTHER INFORMATION: synthetic oligonucleotide for detection

<400> SEQUENCE: 143
ttggaaagca ttagctagtg a                                              21

<210> SEQ ID NO 144
<211> LENGTH: 21
<212> TYPE: DNA
<213> ORGANISM: Artificial Sequence
<220> FEATURE:
<223> OTHER INFORMATION: synthetic oligonucleotide for detection

<400> SEQUENCE: 144
ttggagagca ytagctagtg a                                              21

<210> SEQ ID NO 145
<211> LENGTH: 21
<212> TYPE: DNA
<213> ORGANISM: Artificial Sequence
<220> FEATURE:
<223> OTHER INFORMATION: synthetic oligonucleotide for detection

<400> SEQUENCE: 145
ttggaragca ctagctagtg a                                              21

<210> SEQ ID NO 146
<211> LENGTH: 21
<212> TYPE: DNA
<213> ORGANISM: Artificial Sequence
<220> FEATURE:
<223> OTHER INFORMATION: synthetic oligonucleotide for detection

<400> SEQUENCE: 146
ttggaaagca ytagctagtg a                                              21

<210> SEQ ID NO 147
<211> LENGTH: 21
<212> TYPE: DNA
<213> ORGANISM: Artificial Sequence
<220> FEATURE:
<223> OTHER INFORMATION: synthetic oligonucleotide for detection

```
<400> SEQUENCE: 147
ttggaragca ttagctagtg a                                              21

<210> SEQ ID NO 148
<211> LENGTH: 21
<212> TYPE: DNA
<213> ORGANISM: Artificial Sequence
<220> FEATURE:
<223> OTHER INFORMATION: synthetic oligonucleotide for detection

<400> SEQUENCE: 148
ttggaragca ytagctagtg a                                              21

<210> SEQ ID NO 149
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 149
aattggagag cattagctag tga                                            23

<210> SEQ ID NO 150
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 150
aattggaaag cactagctag tga                                            23

<210> SEQ ID NO 151
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 151
aattggaaag cattagctag tga                                            23

<210> SEQ ID NO 152
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 152
aattggagag cactagctag tga                                            23

<210> SEQ ID NO 153
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 153
aattggarag cactagctag tga                                            23

<210> SEQ ID NO 154
<211> LENGTH: 23
```

```
<212> TYPE: DNA
<213> ORGANISM: Artificial Sequence
<220> FEATURE:
<223> OTHER INFORMATION: synthetic oligonucleotide for detection

<400> SEQUENCE: 154
aattggaaag caytagctag tga                                              23

<210> SEQ ID NO 155
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 155
aattggarag cattagctag tga                                              23

<210> SEQ ID NO 156
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 156
aattggarag caytagctag tga                                              23

<210> SEQ ID NO 157
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 157
aattggarag caytagctag tga                                              23

<210> SEQ ID NO 158
<211> LENGTH: 23
<212> TYPE: DNA
<213> ORGANISM: Artificial Sequence
<220> FEATURE:
<223> OTHER INFORMATION: synthetic oligonucleotide for detection
<220> FEATURE:
<221> NAME/KEY: misc_feature
<222> LOCATION: (8)..(8)
<223> OTHER INFORMATION: n is inosine (i)
<220> FEATURE:
<221> NAME/KEY: misc_feature
<222> LOCATION: (13)..(13)
<223> OTHER INFORMATION: n is inosine (i)

<400> SEQUENCE: 158
aattgganag cantagctag tga                                              23

<210> SEQ ID NO 159
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 159
tcactaattg gagagcatta gctagtga                                         28

<210> SEQ ID NO 160
<211> LENGTH: 28
```

```
<212> TYPE: DNA
<213> ORGANISM: Artificial Sequence
<220> FEATURE:
<223> OTHER INFORMATION: synthetic oligonucleotide for detection

<400> SEQUENCE: 160
tcactaattg gaaagcacta gctagtga                                         28

<210> SEQ ID NO 161
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 161
tcactaattg gaaagcatta gctagtga                                         28

<210> SEQ ID NO 162
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 162
tcactaattg gagagcacta gctagtga                                         28

<210> SEQ ID NO 163
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 163
tcactaattg garagcacta gctagtga                                         28

<210> SEQ ID NO 164
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 164
tcactaattg gaaagcayta gctagtga                                         28

<210> SEQ ID NO 165
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 165
tcactaattg garagcatta gctagtga                                         28

<210> SEQ ID NO 166
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 166
tcactaattg garagcayta gctagtga                                         28
```

```
<210> SEQ ID NO 167
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 167
tcactaattg garagcayta gctagtga                                        28

<210> SEQ ID NO 168
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 168
tgtgtgcaat ctatttgcca ta                                              22

<210> SEQ ID NO 169
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 169
tgtgtacaat ctatttgcca ta                                              22

<210> SEQ ID NO 170
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 170
tgtgtrcaat ctatttgcca ta                                              22

<210> SEQ ID NO 171
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 171
ttctaaatgt gtacaatcta tttgccata                                       29

<210> SEQ ID NO 172
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 172
ttctagatgt gtgcaatcta tttgccata                                       29

<210> SEQ ID NO 173
<211> LENGTH: 29
<212> TYPE: DNA
<213> ORGANISM: Artificial Sequence
<220> FEATURE:
<223> OTHER INFORMATION: synthetic oligonucleotide for detection
```

```
<400> SEQUENCE: 173
ttctaaatgt gtgcaatcta tttgccata                    29

<210> SEQ ID NO 174
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 174
ttctagatgt gtacaatcta tttgccata                    29

<210> SEQ ID NO 175
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 175
ttctaratgt gtacaatcta tttgccata                    29

<210> SEQ ID NO 176
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 176
ttctaratgt gtgcaatcta tttgccata                    29

<210> SEQ ID NO 177
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 177
ttctaaatgt gtrcaatcta tttgccata                    29

<210> SEQ ID NO 178
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 178
ttctagatgt gtrcaatcta tttgccata                    29

<210> SEQ ID NO 179
<211> LENGTH: 29
<212> TYPE: DNA
<213> ORGANISM: Artificial Sequence
<220> FEATURE:
<223> OTHER INFORMATION: synthetic oligonucleotide for detection

<400> SEQUENCE: 179
ttctaratgt gtrcaatcta tttgccata                    29

<210> SEQ ID NO 180
<211> LENGTH: 29
```

```
<212> TYPE: DNA
<213> ORGANISM: Artificial Sequence
<220> FEATURE:
<223> OTHER INFORMATION: synthetic oligonucleotide for detection
<220> FEATURE:
<221> NAME/KEY: misc_feature
<222> LOCATION: (6)..(6)
<223> OTHER INFORMATION: n is inosine (i)
<220> FEATURE:
<221> NAME/KEY: misc_feature
<222> LOCATION: (13)..(13)
<223> OTHER INFORMATION: n is inosine (i)

<400> SEQUENCE: 180
ttctanatgt gtncaatcta tttgccata                                    29

<210> SEQ ID NO 181
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 181
tatggcttct aaatgtgtac aatctatttg ccata                             35

<210> SEQ ID NO 182
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 182
tatggcttct agatgtgtgc aatctatttg ccata                             35

<210> SEQ ID NO 183
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 183
tatggcttct aaatgtgtgc aatctatttg ccata                             35

<210> SEQ ID NO 184
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 184
tatggcttct agatgtgtac aatctatttg ccata                             35

<210> SEQ ID NO 185
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 185
tatggcttct aratgtgtac aatctatttg ccata                             35

<210> SEQ ID NO 186
<211> LENGTH: 35
```

```
<212> TYPE: DNA
<213> ORGANISM: Artificial Sequence
<220> FEATURE:
<223> OTHER INFORMATION: synthetic oligonucleotide for detection

<400> SEQUENCE: 186
tatggcttct aratgtgtgc aatctatttg ccata                              35

<210> SEQ ID NO 187
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 187
tatggcttct aaatgtgtrc aatctatttg ccata                              35

<210> SEQ ID NO 188
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 188
tatggcttct agatgtgtrc aatctatttg ccata                              35

<210> SEQ ID NO 189
<211> LENGTH: 35
<212> TYPE: DNA
<213> ORGANISM: Artificial Sequence
<220> FEATURE:
<223> OTHER INFORMATION: synthetic oligonucleotide for detection

<400> SEQUENCE: 189
tatggcttct aratgtgtrc aatctatttg ccata                              35

<210> SEQ ID NO 190
<211> LENGTH: 32
<212> TYPE: DNA
<213> ORGANISM: Artificial Sequence
<220> FEATURE:
<223> OTHER INFORMATION: synthetic oligonucleotide for detection

<400> SEQUENCE: 190
gaaatcattg ctagttgtcc taaatgtcat at                                 32

<210> SEQ ID NO 191
<211> LENGTH: 42
<212> TYPE: DNA
<213> ORGANISM: Artificial Sequence
<220> FEATURE:
<223> OTHER INFORMATION: synthetic oligonucleotide for detection

<400> SEQUENCE: 191
tgcgcgaaat cattgctagt tgtcctaaat gtcatatgcg ca                      42

<210> SEQ ID NO 192
<211> LENGTH: 42
<212> TYPE: DNA
<213> ORGANISM: Artificial Sequence
<220> FEATURE:
<223> OTHER INFORMATION: synthetic oligonucleotide for detection

<400> SEQUENCE: 192
cgcgcgaaat cattgctagt tgtcctaaat gtcatatgcg cg                      42
```

<210> SEQ ID NO 193
<211> LENGTH: 33
<212> TYPE: DNA
<213> ORGANISM: Artificial Sequence
<220> FEATURE:
<223> OTHER INFORMATION: synthetic oligonucleotide for detection

<400> SEQUENCE: 193
agtctacctg accatgaatt gcttcccctt tta                          33

<210> SEQ ID NO 194
<211> LENGTH: 45
<212> TYPE: DNA
<213> ORGANISM: Artificial Sequence
<220> FEATURE:
<223> OTHER INFORMATION: synthetic oligonucleotide for detection

<400> SEQUENCE: 194
cgcgcaagtc tacctgacca tgaattgctt cccctttat gcgcg              45

<210> SEQ ID NO 195
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 195
aggaagrcar acagcactct tc                                       22

<210> SEQ ID NO 196
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 196
aggaaggcaa acagcactct tc                                       22

<210> SEQ ID NO 197
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 197
aggaagacar acagcactct tc                                       22

<210> SEQ ID NO 198
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 198
aggaaggcar acagcactct tc                                       22

<210> SEQ ID NO 199
<211> LENGTH: 22
<212> TYPE: DNA
<213> ORGANISM: Artificial Sequence
<220> FEATURE:
<223> OTHER INFORMATION: synthetic oligonucleotide for detection

```
<400> SEQUENCE: 199
aggaagacaa acagcactct tc                                              22

<210> SEQ ID NO 200
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 200
aggaaggcag acagcactct tc                                              22

<210> SEQ ID NO 201
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 201
aggaagacag acagcactct tc                                              22

<210> SEQ ID NO 202
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 202
aggaagrcaa acagcactct tc                                              22

<210> SEQ ID NO 203
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 203
aggaagrcag acagcactct tc                                              22

<210> SEQ ID NO 204
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 204
aggaagacag acagctctct tc                                              22

<210> SEQ ID NO 205
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 205
aggaagrcar acagctctct tc                                              22

<210> SEQ ID NO 206
<211> LENGTH: 22
```

```
<212> TYPE: DNA
<213> ORGANISM: Artificial Sequence
<220> FEATURE:
<223> OTHER INFORMATION: synthetic oligonucleotide for detection

<400> SEQUENCE: 206
aggaagacaa acagctctct tc                                                  22

<210> SEQ ID NO 207
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 207
aggaaggcag acagctctct tc                                                  22

<210> SEQ ID NO 208
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 208
aggaaggcaa acagctctct tc                                                  22

<210> SEQ ID NO 209
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 209
aggaagrcag acagctctct tc                                                  22

<210> SEQ ID NO 210
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 210
aggaagrcaa acagctctct tc                                                  22

<210> SEQ ID NO 211
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 211
aggaagacar acagctctct tc                                                  22

<210> SEQ ID NO 212
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 212
aggaaggcar acagctctct tc                                                  22
```

```
<210> SEQ ID NO 213
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 213
aggaagacaa acagcwctct tc                                            22

<210> SEQ ID NO 214
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 214
aggaaggcag acagcwctct tc                                            22

<210> SEQ ID NO 215
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 215
aggaagacag acagcwctct tc                                            22

<210> SEQ ID NO 216
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 216
aggaaggcaa acagcwctct tc                                            22

<210> SEQ ID NO 217
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 217
aggaagrcag acagcwctct tc                                            22

<210> SEQ ID NO 218
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 218
aggaagrcaa acagcwctct tc                                            22

<210> SEQ ID NO 219
<211> LENGTH: 22
<212> TYPE: DNA
<213> ORGANISM: Artificial Sequence
<220> FEATURE:
<223> OTHER INFORMATION: synthetic oligonucleotide for detection
```

```
<400> SEQUENCE: 219
aggaagacar acagcwctct tc                                          22

<210> SEQ ID NO 220
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 220
aggaaggcar acagcwctct tc                                          22

<210> SEQ ID NO 221
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 221
aggaagrcar acagcwctct tc                                          22

<210> SEQ ID NO 222
<211> LENGTH: 25
<212> TYPE: DNA
<213> ORGANISM: Artificial Sequence
<220> FEATURE:
<223> OTHER INFORMATION: synthetic oligonucleotide for detection
<220> FEATURE:
<221> NAME/KEY: misc_feature
<222> LOCATION: (8)..(8)
<223> OTHER INFORMATION: n is inosine (i)
<220> FEATURE:
<221> NAME/KEY: misc_feature
<222> LOCATION: (11)..(11)
<223> OTHER INFORMATION: n is inosine (i)
<220> FEATURE:
<221> NAME/KEY: misc_feature
<222> LOCATION: (17)..(17)
<223> OTHER INFORMATION: n is inosine (i)

<400> SEQUENCE: 222
caggaagnca nacagcnctc ttcct                                       25

<210> SEQ ID NO 223
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 223
gaagagagga agrcaracag cactcttc                                    28

<210> SEQ ID NO 224
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 224
gaagagagga agacaaacag cactcttc                                    28

<210> SEQ ID NO 225
<211> LENGTH: 28
```

```
<212> TYPE: DNA
<213> ORGANISM: Artificial Sequence
<220> FEATURE:
<223> OTHER INFORMATION: synthetic oligonucleotide for detection

<400> SEQUENCE: 225
gaagagagga aggcagacag cactcttc                                            28

<210> SEQ ID NO 226
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 226
gaagagagga aggcaaacag cactcttc                                            28

<210> SEQ ID NO 227
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 227
gaagagagga agacagacag cactcttc                                            28

<210> SEQ ID NO 228
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 228
gaagagagga agacaracag cactcttc                                            28

<210> SEQ ID NO 229
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 229
gaagagagga aggcaracag cactcttc                                            28

<210> SEQ ID NO 230
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 230
gaagagagga agrcaaacag cactcttc                                            28

<210> SEQ ID NO 231
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 231
gaagagagga agrcagacag cactcttc                                            28
```

<210> SEQ ID NO 232
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 232
gaagagagga agrcaracag ctctcttc                                      28

<210> SEQ ID NO 233
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 233
gaagagagga agacaaacag ctctcttc                                      28

<210> SEQ ID NO 234
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 234
gaagagagga aggcagacag ctctcttc                                      28

<210> SEQ ID NO 235
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 235
gaagagagga aggcaaacag ctctcttc                                      28

<210> SEQ ID NO 236
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 236
gaagagagga agacagacag ctctcttc                                      28

<210> SEQ ID NO 237
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 237
gaagagagga agacaracag ctctcttc                                      28

<210> SEQ ID NO 238
<211> LENGTH: 28
<212> TYPE: DNA
<213> ORGANISM: Artificial Sequence
<220> FEATURE:
<223> OTHER INFORMATION: synthetic oligonucleotide for detection -continued

```
<400> SEQUENCE: 238
gaagagagga aggcaracag ctctcttc                                      28

<210> SEQ ID NO 239
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 239
gaagagagga agrcaaacag ctctcttc                                      28

<210> SEQ ID NO 240
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 240
gaagagagga agrcagacag ctctcttc                                      28

<210> SEQ ID NO 241
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 241
gaagagagga agacaaacag cwctcttc                                      28

<210> SEQ ID NO 242
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 242
gaagagagga aggcagacag cwctcttc                                      28

<210> SEQ ID NO 243
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 243
gaagagagga aggcaaacag cwctcttc                                      28

<210> SEQ ID NO 244
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 244
gaagagagga agacagacag cwctcttc                                      28

<210> SEQ ID NO 245
<211> LENGTH: 28
```

```
<212> TYPE: DNA
<213> ORGANISM: Artificial Sequence
<220> FEATURE:
<223> OTHER INFORMATION: synthetic oligonucleotide for detection

<400> SEQUENCE: 245
gaagagagga agacaracag cwctcttc                                          28

<210> SEQ ID NO 246
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 246
gaagagagga aggcaracag cwctcttc                                          28

<210> SEQ ID NO 247
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 247
gaagagagga agrcaaacag cwctcttc                                          28

<210> SEQ ID NO 248
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 248
gaagagagga agrcagacag cwctcttc                                          28

<210> SEQ ID NO 249
<211> LENGTH: 28
<212> TYPE: DNA
<213> ORGANISM: Artificial Sequence
<220> FEATURE:
<223> OTHER INFORMATION: synthetic oligonucleotide for detection

<400> SEQUENCE: 249
gaagagagga agrcaracag cwctcttc                                          28

<210> SEQ ID NO 250
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 250
ggtactccra aggtttgttc tat                                               23

<210> SEQ ID NO 251
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 251
ggtactccra aggattgttc tat                                               23
```

<210> SEQ ID NO 252
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 252
ggtactccra aggtttgctc tat                                              23

<210> SEQ ID NO 253
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 253
ggtactccra aggattgctc tat                                              23

<210> SEQ ID NO 254
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 254
ggtactccra aggwttgctc tat                                              23

<210> SEQ ID NO 255
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 255
ggtactccra aggwttgttc tat                                              23

<210> SEQ ID NO 256
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 256
ggtactccra aggattgytc tat                                              23

<210> SEQ ID NO 257
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 257
ggtactccra aggtttgytc tat                                              23

<210> SEQ ID NO 258
<211> LENGTH: 23
<212> TYPE: DNA
<213> ORGANISM: Artificial Sequence
<220> FEATURE:
<223> OTHER INFORMATION: synthetic oligonucleotide for detection

```
<400> SEQUENCE: 258
ggtactccaa aggattgctc tat                                          23

<210> SEQ ID NO 259
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 259
ggtactccaa aggwttgctc tat                                          23

<210> SEQ ID NO 260
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 260
ggtactccaa aggwttgttc tat                                          23

<210> SEQ ID NO 261
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 261
ggtactccaa aggwttgytc tat                                          23

<210> SEQ ID NO 262
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 262
ggtactccaa aggattgytc tat                                          23

<210> SEQ ID NO 263
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 263
ggtactccaa aggtttgytc tat                                          23

<210> SEQ ID NO 264
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 264
ggtactccaa aggtttgttc tat                                          23

<210> SEQ ID NO 265
<211> LENGTH: 23
```

```
<212> TYPE: DNA
<213> ORGANISM: Artificial Sequence
<220> FEATURE:
<223> OTHER INFORMATION: synthetic oligonucleotide for detection

<400> SEQUENCE: 265
ggtactccaa aggattgttc tat                                              23

<210> SEQ ID NO 266
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 266
ggtactccaa aggtttgctc tat                                              23

<210> SEQ ID NO 267
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 267
ggtactccga aggtttgttc tat                                              23

<210> SEQ ID NO 268
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 268
ggtactccga aggattgttc tat                                              23

<210> SEQ ID NO 269
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 269
ggtactccga aggtttgctc tat                                              23

<210> SEQ ID NO 270
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 270
ggtactccga aggattgctc tat                                              23

<210> SEQ ID NO 271
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 271
ggtactccga aggwttgctc tat                                              23
```

<210> SEQ ID NO 272
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 272
ggtactccga aggwttgttc tat                                         23

<210> SEQ ID NO 273
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 273
ggtactccga aggwttgytc tat                                         23

<210> SEQ ID NO 274
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 274
ggtactccga aggattgytc tat                                         23

<210> SEQ ID NO 275
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 275
ggtactccga aggtttgytc tat                                         23

<210> SEQ ID NO 276
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 276
ggtactccra aggwttgytc tat                                         23

<210> SEQ ID NO 277
<211> LENGTH: 23
<212> TYPE: DNA
<213> ORGANISM: Artificial Sequence
<220> FEATURE:
<223> OTHER INFORMATION: synthetic oligonucleotide for detection
<220> FEATURE:
<221> NAME/KEY: misc_feature
<222> LOCATION: (9)..(9)
<223> OTHER INFORMATION: n is inosine (i)
<220> FEATURE:
<221> NAME/KEY: misc_feature
<222> LOCATION: (14)..(14)
<223> OTHER INFORMATION: n is inosine (i)
<220> FEATURE:
<221> NAME/KEY: misc_feature
<222> LOCATION: (18)..(18)
<223> OTHER INFORMATION: n is inosine (i)

<400> SEQUENCE: 277
ggtactccna aggnttgntc tat        23

<210> SEQ ID NO 278
<211> LENGTH: 23
<212> TYPE: DNA
<213> ORGANISM: Artificial Sequence
<220> FEATURE:
<223> OTHER INFORMATION: synthetic oligonucleotide for detection
<220> FEATURE:
<221> NAME/KEY: misc_feature
<222> LOCATION: (9)..(9)
<223> OTHER INFORMATION: n is inosine (i)
<220> FEATURE:
<221> NAME/KEY: misc_feature
<222> LOCATION: (14)..(14)
<223> OTHER INFORMATION: n is inosine (i)

<400> SEQUENCE: 278
ggtactccna aggnttgttc tat        23

<210> SEQ ID NO 279
<211> LENGTH: 30
<212> TYPE: DNA
<213> ORGANISM: Artificial Sequence
<220> FEATURE:
<223> OTHER INFORMATION: synthetic oligonucleotide for detection

<400> SEQUENCE: 279
atagaacggt actccraagg tttgttctat        30

<210> SEQ ID NO 280
<211> LENGTH: 30
<212> TYPE: DNA
<213> ORGANISM: Artificial Sequence
<220> FEATURE:
<223> OTHER INFORMATION: synthetic oligonucleotide for detection

<400> SEQUENCE: 280
atagaacggt actccgaagg tttgttctat        30

<210> SEQ ID NO 281
<211> LENGTH: 30
<212> TYPE: DNA
<213> ORGANISM: Artificial Sequence
<220> FEATURE:
<223> OTHER INFORMATION: synthetic oligonucleotide for detection

<400> SEQUENCE: 281
atagaacggt actccraagg attgttctat        30

<210> SEQ ID NO 282
<211> LENGTH: 30
<212> TYPE: DNA
<213> ORGANISM: Artificial Sequence
<220> FEATURE:
<223> OTHER INFORMATION: synthetic oligonucleotide for detection

<400> SEQUENCE: 282
atagaacggt actccaaagg wttgttctat        30

<210> SEQ ID NO 283
<211> LENGTH: 30
<212> TYPE: DNA
<213> ORGANISM: Artificial Sequence
<220> FEATURE:
<223> OTHER INFORMATION: synthetic oligonucleotide for detection

```
<400> SEQUENCE: 283
atagaacggt actccaaagg tttgttctat                                              30

<210> SEQ ID NO 284
<211> LENGTH: 30
<212> TYPE: DNA
<213> ORGANISM: Artificial Sequence
<220> FEATURE:
<223> OTHER INFORMATION: synthetic oligonucleotide for detection

<400> SEQUENCE: 284
atagaacggt actccaaagg attgttctat                                              30

<210> SEQ ID NO 285
<211> LENGTH: 30
<212> TYPE: DNA
<213> ORGANISM: Artificial Sequence
<220> FEATURE:
<223> OTHER INFORMATION: synthetic oligonucleotide for detection

<400> SEQUENCE: 285
atagaacggt actccgaagg attgttctat                                              30

<210> SEQ ID NO 286
<211> LENGTH: 30
<212> TYPE: DNA
<213> ORGANISM: Artificial Sequence
<220> FEATURE:
<223> OTHER INFORMATION: synthetic oligonucleotide for detection

<400> SEQUENCE: 286
atagaacggt actccgaagg wttgttctat                                              30

<210> SEQ ID NO 287
<211> LENGTH: 30
<212> TYPE: DNA
<213> ORGANISM: Artificial Sequence
<220> FEATURE:
<223> OTHER INFORMATION: synthetic oligonucleotide for detection

<400> SEQUENCE: 287
atagaacggt actccraagg wttgttctat                                              30

<210> SEQ ID NO 288
<211> LENGTH: 30
<212> TYPE: DNA
<213> ORGANISM: Artificial Sequence
<220> FEATURE:
<223> OTHER INFORMATION: synthetic oligonucleotide for detection

<400> SEQUENCE: 288
atagagcggt actccraagg tttgctctat                                              30

<210> SEQ ID NO 289
<211> LENGTH: 30
<212> TYPE: DNA
<213> ORGANISM: Artificial Sequence
<220> FEATURE:
<223> OTHER INFORMATION: synthetic oligonucleotide for detection

<400> SEQUENCE: 289
atagagcggt actccraagg attgctctat                                              30

<210> SEQ ID NO 290
<211> LENGTH: 30
```

```
<212> TYPE: DNA
<213> ORGANISM: Artificial Sequence
<220> FEATURE:
<223> OTHER INFORMATION: synthetic oligonucleotide for detection

<400> SEQUENCE: 290
atagagcggt actccaaagg attgctctat                                    30

<210> SEQ ID NO 291
<211> LENGTH: 30
<212> TYPE: DNA
<213> ORGANISM: Artificial Sequence
<220> FEATURE:
<223> OTHER INFORMATION: synthetic oligonucleotide for detection

<400> SEQUENCE: 291
atagagcggt actccaaagg wttgctctat                                    30

<210> SEQ ID NO 292
<211> LENGTH: 30
<212> TYPE: DNA
<213> ORGANISM: Artificial Sequence
<220> FEATURE:
<223> OTHER INFORMATION: synthetic oligonucleotide for detection

<400> SEQUENCE: 292
atagagcggt actccaaagg tttgctctat                                    30

<210> SEQ ID NO 293
<211> LENGTH: 30
<212> TYPE: DNA
<213> ORGANISM: Artificial Sequence
<220> FEATURE:
<223> OTHER INFORMATION: synthetic oligonucleotide for detection

<400> SEQUENCE: 293
atagagcggt actccgaagg tttgctctat                                    30

<210> SEQ ID NO 294
<211> LENGTH: 30
<212> TYPE: DNA
<213> ORGANISM: Artificial Sequence
<220> FEATURE:
<223> OTHER INFORMATION: synthetic oligonucleotide for detection

<400> SEQUENCE: 294
atagagcggt actccgaagg attgctctat                                    30

<210> SEQ ID NO 295
<211> LENGTH: 30
<212> TYPE: DNA
<213> ORGANISM: Artificial Sequence
<220> FEATURE:
<223> OTHER INFORMATION: synthetic oligonucleotide for detection

<400> SEQUENCE: 295
atagagcggt actccgaagg wttgctctat                                    30

<210> SEQ ID NO 296
<211> LENGTH: 30
<212> TYPE: DNA
<213> ORGANISM: Artificial Sequence
<220> FEATURE:
<223> OTHER INFORMATION: synthetic oligonucleotide for detection

<400> SEQUENCE: 296
atagagcggt actccraagg wttgctctat                                    30
```

<210> SEQ ID NO 297
<211> LENGTH: 23
<212> TYPE: DNA
<213> ORGANISM: Artificial Sequence
<220> FEATURE:
<223> OTHER INFORMATION: synthetic oligonucleotide for detection

<400> SEQUENCE: 297
ggccaataac acacttgcac aca                                              23

<210> SEQ ID NO 298
<211> LENGTH: 33
<212> TYPE: DNA
<213> ORGANISM: Artificial Sequence
<220> FEATURE:
<223> OTHER INFORMATION: synthetic oligonucleotide for detection

<400> SEQUENCE: 298
agcgcggcca ataacacact tgcacacagc gct                                   33

<210> SEQ ID NO 299
<211> LENGTH: 33
<212> TYPE: DNA
<213> ORGANISM: Artificial Sequence
<220> FEATURE:
<223> OTHER INFORMATION: synthetic oligonucleotide for detection

<400> SEQUENCE: 299
cgcgcggcca ataacacact tgcacacagc gcg                                   33

<210> SEQ ID NO 300
<211> LENGTH: 22
<212> TYPE: DNA
<213> ORGANISM: Artificial Sequence
<220> FEATURE:
<223> OTHER INFORMATION: synthetic oligonucleotide for detection

<400> SEQUENCE: 300
gcctatcaca cacctgcaca ca                                               22

<210> SEQ ID NO 301
<211> LENGTH: 32
<212> TYPE: DNA
<213> ORGANISM: Artificial sequence
<220> FEATURE:
<223> OTHER INFORMATION: synthetic oligonucleotide for detection

<400> SEQUENCE: 301
agcgcgccta tcacacacct gcacacagcg ct                                    32

<210> SEQ ID NO 302
<211> LENGTH: 32
<212> TYPE: DNA
<213> ORGANISM: Artificial sequence
<220> FEATURE:
<223> OTHER INFORMATION: synthetic oligonucleotide for detection

<400> SEQUENCE: 302
cgcgcgccta tcacacacct gcacacagcg cg                                    32

<210> SEQ ID NO 303
<211> LENGTH: 32
<212> TYPE: DNA
<213> ORGANISM: Artificial sequence
<220> FEATURE:
<223> OTHER INFORMATION: synthetic oligonucleotide for detection

<400> SEQUENCE: 303
ccgcggccta tcacacacct gcacacacgc gg          32

<210> SEQ ID NO 304
<211> LENGTH: 33
<212> TYPE: DNA
<213> ORGANISM: Artificial sequence
<220> FEATURE:
<223> OTHER INFORMATION: synthetic oligonucleotide for detection
<220> FEATURE:
<221> NAME/KEY: misc_feature
<222> LOCATION: (10)..(10)
<223> OTHER INFORMATION: n is inosine (i)
<220> FEATURE:
<221> NAME/KEY: misc_feature
<222> LOCATION: (13)..(13)
<223> OTHER INFORMATION: n is inosine (i)
<220> FEATURE:
<221> NAME/KEY: misc_feature
<222> LOCATION: (20)..(20)
<223> OTHER INFORMATION: n is inosine (i)

<400> SEQUENCE: 304
cgcgcggccn atnacacacn tgcacacagc gcg          33

<210> SEQ ID NO 305
<211> LENGTH: 254
<212> TYPE: DNA
<213> ORGANISM: Human immunodeficiency virus

<400> SEQUENCE: 305
ggaggaaatg aacaagtaga taaattagtc agtgctggaa tcaggaaagt actatttta     60 gatggaatag ataaggccca agatgaacat gagaaatatc acagtaattg gagagcaatg    120
gctagtgatt ttaacctgcc acctgtagta gcaaagaaa tagtagccag ctgtgataaa    180
tgtcagctaa aaggagaagc catgcatgga caagtagact gtagtccagg aatatggcaa    240
ctagattgta caca                                                      254

<210> SEQ ID NO 306
<211> LENGTH: 149
<212> TYPE: DNA
<213> ORGANISM: Human immunodeficiency virus

<400> SEQUENCE: 306
aattggagag caatggctag tgattttaac ctgccacctg tagtagcaaa agaaatagta     60
gccagctgtg ataaatgtca gctaaaagga gaagccatgc atggacaagt agactgtagt    120
ccaggaatat ggcaactaga ttgtacaca                                      149

<210> SEQ ID NO 307
<211> LENGTH: 147
<212> TYPE: DNA
<213> ORGANISM: Human immunodeficiency virus

<400> SEQUENCE: 307
ttggagagca atggctagtg attttaacct gccacctgta gtagcaaaag aaatagtagc     60
cagctgtgat aaatgtcagc taaaaggaga agccatgcat ggacaagtag actgtagtcc    120
aggaatatgg caactagatt gtacaca                                        147

<210> SEQ ID NO 308
<211> LENGTH: 149
<212> TYPE: DNA
<213> ORGANISM: Human immunodeficiency virus

```
<400> SEQUENCE: 308
ttggagagca atggctagtg attttaacct gccacctgta gtagcaaaag aaatagtagc    60
cagctgtgat aaatgtcagc taaaaggaga agccatgcat ggacaagtag actgtagtcc   120
aggaatatgg caactagatt gtacacatt                                     149

<210> SEQ ID NO 309
<211> LENGTH: 254
<212> TYPE: DNA
<213> ORGANISM: Human immunodeficiency virus

<400> SEQUENCE: 309
ggaggaaatg aaaaaataga taaattagta agcaaggata ttagaagagt cctgttccta    60
gaaggaatag accaggcaca agaagatcat gaaaaatatc atagtaattg gaaagcacta   120
gctagtgaat ttggactacc accagtggtg gccaaggaaa tcattgctag ctgtcctaaa   180
tgtcatataa aagggaagc aattcatggt caggtagact gcagtccaga agtatggcaa   240
atagattgca caca                                                    254

<210> SEQ ID NO 310
<211> LENGTH: 149
<212> TYPE: DNA
<213> ORGANISM: Human immunodeficiency virus

<400> SEQUENCE: 310
aattggaaag cactagctag tgaatttgga ctaccaccag tggtggccaa ggaaatcatt    60
gctagctgtc ctaaatgtca tataaaaggg gaagcaattc atggtcaggt agactgcagt   120
ccagaagtat ggcaaataga ttgcacaca                                    149

<210> SEQ ID NO 311
<211> LENGTH: 147
<212> TYPE: DNA
<213> ORGANISM: Human immunodeficiency virus

<400> SEQUENCE: 311
ttggaaagca ctagctagtg aatttggact accaccagtg gtggccaagg aaatcattgc    60
tagctgtcct aaatgtcata taaaggggga agcaattcat ggtcaggtag actgcagtcc   120
agaagtatgg caaatagatt gcacaca                                     147
```

HIV TYPE AND SUBTYPE DETECTION

FIELD OF THE INVENTION

The present invention relates to the field of HIV and HIV subtypes. More precisely, the invention relates to the detection of HIV types and subtypes, and especially to the multiplex detection of HIV types and subtypes.

BACKGROUND ART

HIV (Human Immunodeficiency Virus) is the virus responsible for the acquired immunodeficiency syndrome (AIDS), and belongs to the human retrovirus family. AIDS is now considered as one of the greatest threats to human health. An HIV-infected individual can transmit the disease, although remain asymptomatic for years.

The suspected etiological agent responsible for AIDS was independently identified in 1983-1984 by several research groups (see e.g. Barre-Sinoussi et al., Science 220:868-871; Montagnier et al., in Human T-Cell Leukemia Viruses (Gallo, Essex & Gross, eds.); Vilmer et al., The Lancet 1:753), and HIV nomenclature was subsequently unified.

The HIV family comprises several types and subtypes. HIV1 viruses can be classified according to subtypes. Examples of HIV1 sub-types include HIV1-M and HIV1-O. Similarly, HIV2 viruses encompass various sub-types, e.g. HIV2-A and HIV2-B.

For drug development assays, prophylaxis, as well as for treatment of AIDS, it has now become of great importance to be able to quickly and easily identify and quantify the group(s), type(s) and subtype(s) of HIV viruses present in a given sample.

By HIV group, we herein understand any HIV group, irrespective of it being known at the priority date or not. Various HIV groups are known in the art, and are described in the corresponding literature and databases, e.g. ncbi on the internet. Examples thereof include HIV1-M and HIV1-O.

By HIV subtype, we herein understand any HIV subtype, irrespective of it being known at the priority date or not. Various HIV subtypes are known in the art, and are described in the corresponding literature and databases, e.g. ncbi on the internet.

By HIV isolate, we herein understand any HIV isolate or strain, irrespective of it being known at the priority date or not. Various HIV isolates are known in the art, and are described in the corresponding literature and databases, e.g. ncbi on the internet. Some isolates are regarded as references. Examples thereof include K03455, L20587 and M30502.

A possible approach could rely on the development of specific antibodies. However, in terms of sensitivity and specificity, a PCR-based approach usually looks very promising. Also, it generally offers the possibility to work on small samples.

Amplification methods, especially polymerase chain reaction (PCR) and PCR-based methods, e.g. reverse-transcriptase PCR (RT-PCR) and PCR are known in the art (Molecular Cloning: A Laboratory Manual, Maniatis, Fritsch, and Sambrook, CSHL Press; Molecular Biology of the Cell, Alberts et al.; PCR Primer: A Laboratory Manual, Dieffenbach and Dveksler, CSHL Press; The Polymerase Chain Reaction, Mullis, Ferré, and Gibbs, Birkhauser Boston Press; Gene quantification, Ferré, Birkhauser Boston Press.)

These methods are generally very efficient tools for the qualitative and quantitative analysis of complex biological samples.

However, the efficiency of these techniques typically crucially depends on the design and the choice of primers.

There is prior art describing HIV1-specific primers (U.S. Pat. No. 5,712,385; EP 1 043 407; WO 03/020878; EP 1 344 837). There is also prior art describing HIV2-specific primers (U.S. Pat. No. 5,962,665).

Depending upon the working conditions, at least some of these prior art primers may show a sufficient HIV1 or HIV2 specificity, thereby allowing for a specific detection of HIV1 and HIV2. However, to the applicant's knowledge, none of them allows for:

a real-time quantitative specific detection of said subtypes, or for a detection of said subtypes in multiplex which would remain specific, or for a detection of said subtypes in multiplex which would remain quantitative, even when implemented in real-time.

Such a real-time quantitative multiplex specific detection would however be more reliable and informative on the patient's actual infection stage. It would thus give access to a more accurate diagnosis, and as a consequence, would allow to more accurately balance the positive against the deleterious effects of a given treatment. It would allow adjusting or choosing the treatment which should be the most efficient to the particular patient being diagnosed.

Such a real-time quantitative multiplex specific detection would also have the advantage of being faster and easier to run, especially on a large scale.

DESCRIPTION OF THE INVENTION

The present invention provides a process for HIV detection.

The present invention provides oligonucleotides, including primers and probes, and sets thereof, which are suitable for the detection of HIV.

In this respect, the present invention also relates to the field of amplification, PCR and PCR-based methods, as well as diagnostics.

By PCR or PCR reaction, we hereby understand any PCR-based method. This includes standard PCR, qualitative, quantitative and semi-quantitative PCR, real-time PCR, reverse-transcriptase PCR (RT-PCR), simplex and multiplex PCR, and the like.

By real-time PCR, we hereby understand any PCR-based method allowing for monitoring of fluorescence emitted during the reaction as an indicator of amplicon production during each PCR cycle as opposed to the endpoint detection by conventional PCR methods.

By quantitative PCR, we hereby understand any PCR-based method allowing for the estimation of the initial amount of a given PCR target in a given sample.

By multiplex PCR, we hereby understand any PCR reaction aiming at the amplification of more than one target. For instance, multiplex PCR include duplex PCR (two targets), triplex PCR (three targets), and higher multiplex PCR. Multiplex PCR includes PCR reactions with more than one primer pair, for instance two primer pairs. In this case, there might be four different primers, but it is also possible for the two primer pairs to have one primer in common, e.g. the forward primer, and to have two distinct reverse primers. Multiplex PCR also includes PCR reactions with a unique primer pair, but with more than one probe.

By oligonucleotide, we hereby understand any short polymer of nucleotides, wherein nucleotides can be ribonucleotides, deoxyribonucleotides, dideoxyribonucleotides, degenerated nucleotides, and the like. Said oligonucleotides are preferably single-stranded. The length of said oligonucleotides can vary, and is usually under 150 nucleotides (nt), preferably in the range of 10-100 nt, more preferably 15-60 nt, even more preferably 18-50 nt. Said oligonucleotides can bear chemical modifications, such as tagging or marking, for instance radioactive, fluorescent, biotinylated, dig labelling. An oligonucleotide according to the invention can be either forward (sense) or reverse (antisense). In addition, it should be stressed, that although preferred functions may be mentioned in relation to some oligonucleotides according to the present invention, it is obvious that a given oligonucleotide may assume several functions, and may be used in different ways according to the present invention. For example, an oligonucleotide can be used either as a primer, or as a probe. Also, when an oligonucleotide is described as being useful as an amplicon-targeting probe, the skilled person understands that the complementary sequence of this oligonucleotide is equally useful as a probe to target the same amplicon. Moreover, it is also obvious, that any primer suitable for a multiplex assay, can also, within the meaning of the present invention, be used in a simplex protocol. The same applies to a primer suitable for a real-time protocol, which can also be used in the framework of an end-point assay within the meaning of the present invention.

Oligonucleotides according to the invention especially include PCR primers and probes. Unless otherwise stated, nucleic acid sequences are given in the 5' to 3' direction. Said oligonucleotides can be under many forms, e.g. under dry state, in solution/suspension with the desired solvent and the desired concentration. The skilled person would know, which solvents, concentrations, storage conditions are suitable for the oligonucleotides of the invention. In particular, the skilled person would know how to prepare said oligonucleotides as stock solutions. The oligonucleotides according to the invention can also assume various degrees of purity, as can be judged by those skilled in the art, e.g. by HPLC chromatography.

By set of oligonucleotides, we hereby understand any combination comprising at least one oligonucleotide, preferably at least two, e.g. 2-10 oligonucleotides. Said set can thus comprise one PCR primer, or a pair of PCR primers, or a probe, or a probe and a pair of primers. Said oligonucleotides can be separately kept, or partially mixed, or entirely mixed.

The notion of primer or PCR primer is known to those skilled in the art. For example, it includes any oligonucleotide able to anneal to a target template under suitable stringency conditions, and allowing for polymerase strand elongation. The typical length of said primer is 15-30 nt, preferably 18, 19, 20, 21, 22, 23, 24 or 25 nt.

The notion of probe is also known to those skilled in the art. For example, it includes any oligonucleotide able to anneal to a target template under the desired hybridization conditions. The typical length of said probe is 20-55 nt, preferably 15-60 nt, more preferably 20-55 nt, more preferably 30-50 nt, more preferably 35-45 nt. Preferably, said probe is fluorescently labelled. However, it is clear to those skilled in the art that under certain conditions, one may use a primer as a probe and vice-versa. Moreover, it is herein stressed that the products according to the present invention, especially, inter alia, oligonucleotides, are not limited to the intended use herein mentioned, but rather are to be broadly construed, irrespective of the indicated destination. For instance, a claim to a product (oligonucleotide) for a particular use should be construed as meaning a product (oligonucleotide) which is in fact suitable for the stated use. Thus, an oligonucleotide suitable for use as a primer in a multiplex protocol is also clearly adapted to a simplex protocol within the meaning of the present invention.

Various formats (types) of probes, including Taqman™ probes (hydrolysis probes), molecular Beacons™ (beacon probes or molecular beacon probes), and Scorpion™ probes are known in the art.

In a preferred embodiment, the probes according to the invention can all be synthesized and used in the molecular beacon format.

The structure of molecular beacons is as follows. A short nucleotide sequence (so-called beacon arm) which is unrelated to the target sequence is thus covalently linked to both ends of the probe. A short unrelated arm is thus linked in 5' of the probe, and is labelled with a fluorescent moiety (i.e. fluorescent dye or fluorescent marker). Another but still unrelated arm is linked to the 3' end of probe and is labelled with a fluorescence quenching moiety. Thus, molecular beacons have a fluorophore and a quencher at opposite ends. The 5' short arm is totally complementary to the one in 3' so that they can anneal together, and thus can assume a hairpin structure when unhybridized to the target in solution. In this hairpin conformation, the quencher and the fluorescent dye are close enough to each other to allow efficient quenching of the fluorophore. However, when the probe encounters a target molecule, annealing is favoured with respect to the hairpin conformation when values of beacon arm Tm and probe Tm are suitably chosen (theoretically: probe Tm>beacon arm Tm>primer Tm, wherein Tm is the melting temperature of interest). The fluorophore and quencher move away from each other and the fluorophore can then fluoresce when illuminated by suitable light excitation. As PCR proceeds, amplification product accumulates, and the amount of fluorescence at any given cycle depends on the amount of amplification product present at that time. (See e.g. Sanjay Tyagi and Fred Russell Kramer, *Nature Biotechnology* 1996, volume 14, pages 303-308; *Nature Biotechnology* 1998, volume 16, pages 49-53).

(Remark: It is also possible to link the fluorophore at the 3' end, while attaching the quencher at the 5' end.)

Schematically, said probe can have the following formulae (molecular beacon format):

5' Fluorophore-(arm 1)-probe-(arm2)-Quencher 3'
5' Quencher-(arm 1)-probe-(arm2)-Fluorophore 3' wherein arm1 and arm2 can be any short nucleotide sequences, e.g. in the range of 3-10 nucleotides, preferably 5, 6, 7 nucleotides, allowing for the hair pin structure formation under suitable stringency conditions, i.e. arm1 and arm2 are totally complementary to anneal under the desired stringency conditions (standard PCR stringency conditions include, for example, an annealing temperature of 55 to 65° C. and an Mg concentration of 4 to 8 mM). However, arm1 and arm2 are unrelated to the target sequence of the probe, i.e. the hairpin conformation resulting from the annealing between arm1 and arm2 is essentially the only possible secondary structure for the probe when unhybridized. The skilled person would know how to choose such arms for a given probe.

For example, possible beacon formats include:

```
TGCGC-(probe sequence)-GCGCA

GCGCA-(probe sequence)-TGCGC

AGCGC-(probe sequence)-GCGCT

GCGCT-(probe sequence)-AGCGC
```

-continued

```
CGCGA-(probe sequence)-TCGCG

CGCGC-(probe sequence)-GCGCG.
```

By fluorophore, it is herein understood any fluorescent marker/dye known in the art. Examples of such suitable fluorescent markers include Fam, Hex, Tet, Joe, Rox, Tamra, Max, Edans, Cy dyes such as Cy5, Fluorescein, Coumarin, Eosine, Rhodamine, Bodipy, Alexa, Cascade Blue, Yakima Yellow, Lucifer Yellow and Texas Red (all of them are Trade-Marks).

By quencher, we herein understand any quencher known in the art. Examples of such quenchers include Dabcyl, Dark Quencher, Eclipse Dark Quencher, ElleQuencher, Tamra, BHQ and QSY (all of them are Trade-Marks).

The skilled person would know which combinations of dye/quencher are suitable when designing a probe.

In a preferred embodiment according to the invention, spectral properties of said probes can be chosen as to not interfere with each other. In particular, when probes are used in multiplex, each single probe can have its own fluorophore being spectrally significantly different from each other, i.e. the absorption/emission spectra are essentially non-overlapping. This advantageously allows for low-noise multiplex detection for all single probes, making sure that individual signals do not interfere with each other in detection. Examples of dyes which can be used together in multiplex include Fam with Tamra, Fam with Tamra with Texas Red.

According to the invention, all the provided oligonucleotides can be either kept separately, or partially mixed, or totally mixed.

Said oligonucleotides can be provided under dry form, or solubilized in a suitable solvent, as judged by the skilled person. Suitable solvents include TE, PCR-grade water, and the like.

Thereafter, sequences are identified by a SEQ ID NO:

The corresponding sequences are given on the tables in the figures appended thereto. In said tables, the standard code for degenerated nucleotides is used. In particular: R is G or A; Y is C or T; W is A or T.

In the given sequences, where several positions are degenerated, it is clear to those skilled in the art that each degenerated position can be chosen independently from each other. For example, RY can be GC, GT, AC, AT, combinations and mixtures thereof. Thus, SEQ ID NO: 52 may be any one of SEQ ID NO: 25 to 51 (see table) or combinations or mixtures thereof, etc.

In addition, in said tables, d indicates a degenerated oligonucleotide; e denotes an expanded oligonucleotide (i.e. a lengthened version of another oligonucleotide); and l designates a loop oligonucleotide.

By loop oligonucleotide, we hereby understand any oligonucleotide, whose 5' end has been modified by addition of a few nucleotides (generally 3, 4, 5, 6 or 7 nt) so as to be complementary to the 3' end of said any oligonucleotide. Thus, said loop oligonucleotide has the advantageous feature of being able to adopt a loop conformation under given stringency conditions. This property is extremely advantageous in increasing the specificity and sensitivity in a PCR protocol, in particular in a multiplex protocol, by avoiding interactions between primers, or between primers and probes.

The present invention provides a process for the detection of HIV. In one aspect, the invention provides a process for the detection of at least one HIV target, comprising the step of producing at least one amplicon by means of at least two oligonucleotides, wherein said oligonucleotides are suitable for use in the specific amplification of at least one reference template sequence selected from the group consisting of:
  positions 4281-4436 (SEQ ID NO: 2) of the K03455 HIV1-M reference isolate; and the fragments of SEQ ID NO: 2 selected from positions 4281-4429 (SEQ ID NO: 306), 4283-4429 (SEQ ID NO: 307), 4283-4431 (SEQ ID NO: 308) of said HIV1-M isolate;
  positions 4336-4491 (SEQ ID NO: 4) of the L20587 HIV1 O reference isolate, and the fragments of SEQ ID NO: 4 selected from positions 4336-4484 (SEQ ID NO: 310), 4338-4484 (SEQ ID NO:311) of said HIV 1-O isolate;
  positions 4889-5036 (SEQ ID NO: 5) of the M30502 HIV2 reference isolate;
  positions 4176-4436 (SEQ ID NO: 1) of the K03455 HIV1-M reference isolate, and the fragment of SEQ ID NO:1 which is identical to positions 4176-4429 (SEQ ID NO: 305) of said HIV1-M isolate; and
  positions 4231-4491 (SEQ ID NO: 3) of the L20587 HIV1-O reference isolate, and the fragment of SEQ ID NO:3 which is identical to positions 4231-4484 (SEQ ID NO: 309) of said HIV1-O isolate.

The reference template sequences hence correspond to isolated fragments of a determined HIV isolate (i.e. the fragment which is identical to the sequence extending from the indicated positions). The oligonucleotides suitable for use in the specific amplification of at least said reference template sequence are hence selected to target this reference template sequence, in such a location that they would lead to the amplification of this reference template sequence under the form of an isolated fragment.

In another aspect, the invention provides a process for the detection of at least one HIV target, comprising the step of producing at least one amplicon by means of at least two oligonucleotides, wherein said oligonucleotides are 'quantitative friendly' and/or 'multiplex-friendly' primers which are suitable for use in the specific amplification of at least one reference template sequence selected from the group consisting of:
  positions 4281-4436 (SEQ ID NO: 2) of the K03455 HIV1-M reference isolate; and the fragments of SEQ ID NO: 2 selected from positions 4281-4429, 4283-4429, 4283-4431 of said HIV1-M isolate (SEQ ID NO: 306, 307 and 308);
  positions 4336-4491 (SEQ ID NO: 4) of the L20587 HIV1-O reference isolate, and the fragments of SEQ ID NO: 4 selected from positions 4336-4484, 4338-4484 of said HIV1-O isolate (SEQ ID NO: 310 and 311);
  positions 4889-5036 (SEQ ID NO: 5) of the M30502 HIV2 reference isolate;
  positions 4176-4436 (SEQ ID NO: 1) of the K03455 HIV1-M reference isolate, and the fragment of SEQ ID NO:1 which is identical to positions 4176-4429 (SEQ ID NO: 305) of said HIV1-M isolate; and
  positions 4231-4491 (SEQ ID NO: 3) of the L20587 HIV1-O reference isolate, and the fragment of SEQ ID NO:3 which is identical to positions 4231-4484 (SEQ ID NO: 309) of said HIV1-O isolate.

In another aspect, the invention provides a process for the detection of at least one HIV target, comprising the amplification of at least one reference template sequence selected from the group consisting of:
  positions 4281-4436 (SEQ ID NO: 2) of the K03455 HIV1-M reference isolate; and the fragments of SEQ ID NO: 2 selected from positions 4281-4429, 4283-4429, 4283-4431 of said HIV1-M isolate;

positions 4336-4491 (SEQ ID NO: 4) of the L20587 HIV1-O reference isolate, and the fragments of SEQ ID NO: 4 selected from positions 4336-4484, 4438-4484 of said HIV1-O isolate;

positions 4889-5036 (SEQ ID NO: 5) of the M30502 HIV2 reference isolate;

positions 4176-4436 (SEQ ID NO: 1) of the K03455 HIV1-M reference isolate, and the fragment of SEQ ID NO:1 which is identical to positions 4176-4429 of said HIV1-M isolate; and positions 4231-4491 (SEQ ID NO: 3) of the L20587 HIV1-O reference isolate, and the fragment of SEQ ID NO:3 which is identical to positions 4231-4484 of said HIV1-O isolate.

In a preferred embodiment, said process comprises the step of detecting said amplicon by means of at least one probe.

The term amplicon is known to those skilled in the art. By amplicon, we herein understand any amplification product.

Amplification is known in the art, and can be any process involving at least one amplification step, in particular at least one PCR or a PCR-based amplification step.

By 'multiplex-friendly' oligonucleotide, we herein understand any oligonucleotide which can be successfully used in a multiplex (PCR) protocol. In particular, 'multiplex-friendly' oligonucleotides allow specific and sensitive results in a multiplex protocol.

By 'quantitative friendly' oligonucleotide, we herein understand any oligonucleotide which can be successfully used in a quantitative (PCR) protocol. In particular, 'quantitative-friendly' oligonucleotides allow specific, sensitive and quantitative results.

A sequence complementary to another sequence is herein meant as a sequence which is complementary to said other sequence over the entire length of this other sequence.

Although the process according to the present invention can advantageously be carried out in the framework of a multiplex protocol, it is also clearly possible to carry it out as a simplex protocol, for example a simplex end-point or qualitative protocol.

By reference template sequence, we herein understand any template sequence which can be used as a reference for alignment. For example, some genomes are considered as reference genome. Sequence alignment is known in the art. Advantageously according to the invention, SEQ ID NO: 1 to 5 and the above-mentioned fragments thereof are reference template sequences sharing the specific technical feature of being suitable references to construct and produce primers which allow for a quantitative detection of at least one of the HIV1-M, HIV1-O, HIV2-A and HIV2-B subtypes. Said reference template sequences are suitable references to construct and produce primers which allow for:

a real-time quantitative detection of at least one of said HIV subtypes, a multiplex detection of at least one of said HIV subtypes, a real-time quantitative multiplex detection of at least one of said HIV subtypes.

The reference template sequences of the invention notably comprise the sequences selected from the group consisting of:

positions 4176-4436 (SEQ ID NO: 1) of the K03455 HIV1-M reference isolate, and the fragments of SEQ ID NO:1 selected from positions 4281-4436 (SEQ ID NO: 2), 4281-4429, 4283-4429, 4283-4431, and 4176-4429 of said K03455 HIV1-M reference isolate;

positions 4231-4491 (SEQ ID NO: 3) of the L20587 HIV1-O reference isolate, and the fragments of SEQ ID NO:3 selected from positions 4336-4491 (SEQ ID NO: 4), 4336-4484, 4338-4484, and 4231-4484 of said L20587 HIV1-O reference isolate;

positions 4889-5036 (SEQ ID NO: 5) of the M30502 HIV2 reference isolate.

Thus, the process according to the invention advantageously allows the specific and sensitive detection of the main HIV groups and/or types and/or subtypes, and of possibly virtually any HIV groups and/or types and/or subtypes, by a real-time quantitative and/or multiplex amplification protocol. Examples of such groups and/or types and/or subtypes covered by the process according to the present invention include HIV1-M subtypes A (A1 and A2), B, C, D, F (F1 and F2), G, H, J and K, but also the recombinant forms AE, AG, AB, DF, BC, CD, BF and BG, and also U (highly divergent). Further examples thereof comprises HIV2 subtypes A, B.

The invention hence provides a HIV detection process by nucleic by acid amplification which:

can be group- and/or type- and/or subtype-specific, is quantitative, and more particularly allows for a real-time quantitative HIV detection, can be implemented in multiplex while still remaining specific, and can even be implemented in a (possibly real-time) quantitative multiplex amplification protocol.

Thus, the process according to the invention can advantageously facilitate diagnostics procedures by differentiating-HIV1-M and HIV1-O groups from HIV2 group and covering a very broad spectrum of HIV types and/or sub-types using a single procedure.

In one aspect of the invention, said reference template sequence is SEQ ID NO: 2, from the K03455 HIV1-M reference isolate, or a fragment of SEQ ID NO: 2 selected from positions 4281-4429, 4283-4429, 4283-4431.

In one embodiment, said reference template sequence is SEQ ID NO: 2, from the K03455 HIV1-M reference isolate, or one of said fragments of SEQ ID NO: 2, and said process is carried out with at least one oligonucleotide selected from the group consisting of:

SEQ ID NO: 9, 12, 14, 15, 24, 52, 82, 91, 100, 109, 118, 127, 136, and the sequences which are complementary to one of SEQ ID NO: 91, 100, 109, 118, 127, 136 over the entire length of this SEQ ID NO:

In a preferred embodiment, said process is carried out with at least one primer selected from the group consisting of:

SEQ ID NO: 9, 12, 14, 15, 24, 52, 82.

In another embodiment, said process is carried out with at least one probe selected from the group consisting of:

SEQ ID NO: 91, 100, 109, 118, 127, 136, and the complementary sequences thereof.

In a more preferred embodiment, said process is carried out with at least one primer selected from the group consisting of:

SEQ ID NO:9, 12, 14, 15.

and with at least one primer selected from the group consisting of:

SEQ ID NO: 24, 52, 82.

In a still more preferred embodiment, said process is carried out with at least one primer selected from the group consisting of:

SEQ ID NO: 9, 12, 14, 15;

and with at least one primer selected from the group consisting of:

SEQ ID NO: 24, 52, 82;

and, optionally, with at least one probe selected from the group consisting of:

SEQ ID NO: 91, 100, 109, 110, 118, 127, 136, and the complementary sequences thereof.

The possible combinations of primers (primer pairs) are thus as follows:

| SEQ ID NO: | 9 | 12 | 14 | 15 |
|---|---|---|---|---|
| 24 | X | X | X | X |
| 52 | X | X | X | X |
| 82 | X | X | X | X | wherein X indicates that the primers can be combined with each other as a pair, and that each primer pair can in addition be used in combination with any one of the probes selected from the group consisting of:

SEQ ID NO: 91, 100, 109, 110, 118, 127, 136, and the complementary sequences thereof.

In another aspect of the invention, said reference template sequence is SEQ ID NO: 4, from the L20587 HIV1-O reference isolate, or a fragment of SEQ ID NO: 4 selected from 4336-4484, 4338-4484.

In one embodiment of the invention, said reference template sequence is SEQ ID NO: 4, from the L20587 HIV1-O reference isolate or one of said fragments of SEQ ID NO: 4, and said process is carried out with at least one oligonucleotide selected from the group consisting of:

SEQ ID NO: 148, 157, 167, 170, 179, 189, 190 to 194, and the sequences which are complementary to one of SEQ ID NO: 190 to 194 over the entire length of this SEQ ID NO:

In a preferred embodiment, said process is carried out with at least one primer selected from the group consisting of:

SEQ ID NO: 148, 157, 167, 170, 179, 189.

In another embodiment, said process is carried out with at least one probe selected from the group consisting of:

SEQ ID NO: 190 to 194, and the complementary sequences thereof.

In a more preferred embodiment, said process is carried out with at least one primer selected from the group consisting of:

SEQ ID NO: 148, 157, 167;

and with at least one primer selected from the group consisting of:

SEQ ID NO: 170, 179, 189.

In a still more preferred embodiment, said process is carried out with at least one primer selected from the group consisting of:

SEQ ID NO: 148, 157, 167;

and with at least one primer selected from the group consisting of:

SEQ ID NO: 170, 179, 189;

and, optionally, with at least one probe selected from the group consisting of:

SEQ ID NO: 190 to 194, and the complementary sequences thereof.

The possible combinations of primers (primer pairs) are thus as follows:

| SEQ ID NO: | 148 | 157 | 167 |
|---|---|---|---|
| 170 | X | X | X |
| 179 | X | X | X |
| 189 | X | X | X | wherein X indicates that the primers can be combined with each other as a pair, and that each primer pair can in addition be used in combination with any one of the probes selected from the group consisting of:

SEQ ID NO: 190, 191, 192, 193, 194, and the complementary sequences thereof.

In another aspect of the invention, said reference template sequence is SEQ ID NO: 5, from the M30502 HIV2 reference isolate.

In one embodiment of the invention, said reference template sequence is SEQ ID NO: 5, from the M30502 HIV2 reference isolate, and said process is carried out with at least one oligonucleotide selected from the group consisting of:

SEQ ID NO: 221, 249, 276, 287, 296, 297 to 303, and the sequences which are complementary to one of SEQ ID NO: 297 to 303 over the entire length of this SEQ ID NO:

In a preferred embodiment, said process is carried out with at least one primer selected from the group consisting of:

SEQ ID NO: 221, 249, 276, 287, 296.

In another embodiment, said process is carried out with at least one probe selected from the group consisting of:

SEQ ID NO: 297 to 303, and the complementary sequences thereof.

In a more preferred embodiment, said process is carried out with at least one primer selected from the group consisting of:

SEQ ID NO: 221, 249;

and with at least one primer selected from the group consisting of:

SEQ ID NO: 276, 287, 296.

In a still more preferred embodiment, said process is carried out with at least one primer selected from the group consisting of:

SEQ ID NO: 221, 249;

and with at least one primer selected from the group consisting of:

SEQ ID NO: 276, 287, 296;

and, optionally, with at least one probe selected from the group consisting of:

SEQ ID NO: 297 to 303, and the complementary sequences thereof.

The possible combinations of primers (primer pairs) are thus as follows:

| SEQ ID NO: | 221 | 249 |
|---|---|---|
| 276 | X | X |
| 287 | X | X |
| 296 | X | X | wherein X indicates that the primers can be combined with each other as a pair, and that each primer pair can in addition be used in combination with any one of the probes selected from the group consisting of:

SEQ ID NO: 297, 298, 299, 300, 301, 302, 303, and the complementary sequences thereof.

In another aspect of the invention, said reference template sequence is SEQ ID NO: 1, from the K03455 HIV1-M reference isolate, or the fragment of SEQ ID NO:1 which is identical to positions 4176-4429 of said K03455 HIV1-M reference isolate.

In one embodiment of the invention, said reference template sequence is SEQ ID NO: 1, from the K03455 HIV1-M reference isolate, or said fragment thereof, and said process is carried out with at least one oligonucleotide selected from the group consisting of:

SEQ ID NO: 6, 24, 52, 82, 91, 100, 109, 118, 127, 136, and the sequences which are complementary to one of SEQ ID NO: 91, 100, 109, 118, 127, 136, over the entire length of this SEQ ID NO:

In a preferred embodiment, said process is carried out with at least one primer selected from the group consisting of:
SEQ ID NO: 6, 24, 52, 82.

In another embodiment, said process is carried out with at least one probe selected from the group consisting of:
SEQ ID NO: 91, 100, 109, 118, 127, 136, and the complementary sequences thereof.

In a more preferred embodiment, said process is carried out with at least one primer selected which is:
SEQ ID NO: 6;
and with at least one primer selected from the group consisting of:
SEQ ID NO: 24, 52, 82.

In a still more preferred embodiment, said process is carried out with at least one primer selected which is:
SEQ ID NO: 6;
and with at least one primer selected from the group consisting of:
SEQ ID NO: 24, 52, 82;
and, optionally, with at least one probe selected from the group consisting of:
SEQ ID NO: 91, 100, 109, 118, 127, 136, and the complementary sequences thereof.

The possible combinations of primers (primer pairs) are thus as follows:

| SEQ ID NO: | 24 | 52 | 82 |
|---|---|---|---|
| 6 | X | X | X | wherein X indicates that the primers can be combined with each other as a pair, and that each primer pair can in addition be used in combination with any one of the probes selected from the group consisting of:
SEQ ID NO: 91, 100, 109, 118, 127, 136, and the complementary sequences thereof.

In another aspect of the invention, said reference template sequence is SEQ ID NO: 3, from the L20587 HIV1-O reference isolate, or the fragment of SEQ ID NO:3 which is identical to positions 4231-4484 of said L20587 HIV1-O reference isolate.

In one embodiment of the invention, said reference template sequence is SEQ ID NO: 3, from the L20587 HIV1-O reference isolate, or said fragment thereof, and said process is carried out with at least one oligonucleotide selected from the group consisting of:
SEQ ID NO: 139, 170, 179, 189, 190 to 194, and the sequences which are complementary to one of SEQ ID NO: 190 to 194 over the entire length of this SEQ ID NO:

In a preferred embodiment, said process is carried out with at least one primer selected from the group consisting of:
SEQ ID NO: 139, 170, 179, 189.

In another embodiment, said process is carried out with at least one probe selected from the group consisting of:
SEQ ID NO: 190 to 194, and the complementary sequences thereof.

In a more preferred embodiment, said process is carried out with at least one primer which is:
SEQ ID NO: 139;
and with at least one primer selected from the group consisting of:
SEQ ID NO: 170, 179, 189.

In a still more preferred embodiment, said process is carried out with at least one primer which is:
SEQ ID NO: 139;
and with at least one primer selected from the group consisting of:
SEQ ID NO: 170, 179, 189;
and, optionally, with at least one probe selected from the group consisting of:
SEQ ID NO: 190 to 194, and the complementary sequences thereof.

The possible combinations of primers (primer pairs) are thus as follows:

| SEQ ID NO: | 170 | 179 | 189 |
|---|---|---|---|
| 139 | X | X | X | wherein X indicates that the primers can be combined with each other as a pair, and that each primer pair can in addition be used in combination with any one of the probes selected from the group consisting of:
SEQ ID NO: 190, 191, 192, 193, 194, and the complementary sequences thereof.

In one aspect of the invention, said step of producing at least one amplicon comprises at least one quantitative and/or qualitative, multiplex and/or simplex PCR amplification.

In another aspect of the invention, said step of detecting preferentially includes real-time and/or quantitative and/or end-point detection.

In another aspect, the present invention provides an amplicon obtainable by the above-described process, i.e. by implementation of the process of the invention on a HIV-containing sample.

In a further aspect, there is provided an amplification composition comprising at least one amplicon according to the invention. By amplification composition, we herein understand any composition obtainable by amplification, especially by PCR.

The invention is also directed to a polynucleotide suitable for use as a reference template sequence in the design of primers that can be used in multiplex to cover at least HIV1-M, HIV1-O, HIV2-A and HIV2-B in a single amplification run while still offering a real time quantitative amplification thereof. Naturally, the polynucleotides according to the present invention are also suitable for further protocols, including simplex protocols, multiplex protocols, end-point protocols, qualitative protocols, quantitative protocols, combinations thereof, and the like.

By polynucleotide, we hereby understand any polymer of nucleotides, wherein nucleotides can be ribonucleotides, deoxyribonucleotides, dideoxyribonucleotides, degenerated nucleotides, and the like. Said nucleotides are preferably single-stranded, but can also be double stranded. The length of said polynucleotides can vary, and is usually under 500 nucleotides (nt), preferably in the range of 50-400 nt, more preferably 100-300 nt, even more preferably 150-250 nt.

In a preferred embodiment, said reference template polynucleotide is:
positions 4281-4436 (SEQ ID NO: 2) of the K03455 HIV1-M reference isolate (see FIG. 7), or a fragment of SEQ ID NO: 2 selected from 4281-4429, 4283-4429, 4283-4431.

In another embodiment, said reference template polynucleotide is:
positions 4336-4491 (SEQ ID NO: 4) of the L20587 HIV1-O reference isolate (see FIG. 7), or a fragment of SEQ ID NO: 4 selected from 4336-4484, 4338-4484.

In another embodiment, said reference template polynucleotide is:
positions 4889-5036 (SEQ ID NO: 5) of the M30502 HIV2 reference isolate (see FIG. 7).

In yet another embodiment, said reference template polynucleotide is:
positions 4176-4436 (SEQ ID NO: 1) of the K03455 HIV1-M reference isolate (see FIG. 7), or the fragment of SEQ ID NO: 1 which is identical to positions 4176-4429 of said K03455 HIV1-M isolate.

In a further embodiment, said reference template polynucleotide is:
positions 4231-4491 (SEQ ID NO: 3) of the L20587 HIV1-O reference isolate (see FIG. 7), or the fragment of SEQ ID NO:3 which is identical to positions 4231-4484 of said L20587 HIV1-O isolate.

According to the present invention, there is provided an oligonucleotide suitable for HIV detection: see FIGS. 7 to 21.

In one embodiment, the invention provides an oligonucleotide which is selected from the group consisting in:
SEQ ID NO: 6 to 304, and the sequences which are complementary to one of SEQ ID NO: 83-138, 190-194, 297-304 over the entire length of this SEQ ID NO:

In a preferred embodiment, the invention provides an oligonucleotide which is selected from the group consisting in:
SEQ ID NO: 6, 9, 12, 14, 15, 24, 52, 82, 91, 100, 109, 118, 127, 136, 139, 148, 157, 167, 170, 179, 189, 190 to 194, 221, 249, 276, 287, 296, 297 to 303, and
the sequences which are complementary to one of SEQ ID NO: 91, 100, 109, 118, 127, 136, 190, 191, 192, 193, 194, 297, 298, 299, 300, 301, 302, 303, over the entire length of this SEQ ID NO:

In one aspect, the invention provides an oligonucleotide which is suitable for HIV1-M detection, and which is selected from the group consisting in:
SEQ ID NO: 6, 9, 12, 14, 15, 24, 52, 82, 91, 100, 109, 118, 127, 136, and the sequences which are complementary to one of SEQ ID NO: 91, 100, 109, 118, 127, 136 over the entire length of this SEQ ID NO.

In another aspect, the invention provides an oligonucleotide which is suitable for HIV1-O detection and which is selected from the group consisting in:
SEQ ID NO: 139, 148, 157, 167, 170, 179, 189, 190 to 194, and the sequences which are complementary to one of SEQ ID NO: 190-194, over the entire length of this SEQ ID NO.

In yet another aspect, the invention provides an oligonucleotide which is suitable for HIV2-A detection and which is selected from the group consisting in:
SEQ ID NO: 221, 249, 276, 287, 296, 297 to 299, and the sequences which are complementary to one of SEQ ID NO: 297-299, over the entire length of this SEQ ID NO.

In yet another aspect, the invention provides an oligonucleotide which is suitable for HIV2-B detection and which is selected from the group consisting in:
SEQ ID NO: 221, 249, 276, 287, 296, 300 to 303, and the sequences which are complementary to one of SEQ ID NO: 300-303, over the entire length of this SEQ ID NO:

Please note that sequences such as SEQ ID NO: 9 or SEQ ID N:12 are degenerated sequences: SEQ ID NO: 9 with R=A is identical to SEQ ID NO: 8; SEQ ID NO: 12 with R=A is identical to SEQ ID NO: 11.

In another aspect, the invention provides the following oligonucleotides, being suitable for the indicated uses:

| possible use | SEQ ID NO: |
| --- | --- |
| HIV1-M forward primer | 6-15 |
| HIV1-M reverse primer | 16-82 |
| HIV1-M probe | 83-138 |
|  | (+complementary sequences thereof) |
| HIV1-O forward primer | 139-167 |
| HIV1-O reverse primer | 168-189 |
| HIV1-O probe | 190-194 |
|  | (+complementary sequences thereof) |
| HIV2 forward primer | 195-249 |
| HIV2 reverse primer | 250-296 |
| HIV2-A probe | 297-299 |
|  | (+complementary sequences thereof) |
| HIV2-B probe | 300-303 |
|  | (+complementary sequences thereof) |

In a further aspect, the invention provides the following oligonucleotides, being suitable for the indicated uses:

| possible use | SEQ ID NO: |
| --- | --- |
| HIV1-M forward primer | 6, 9, 12, 14, 15 |
| HIV1-M reverse primer | 24, 52, 82 |
| HIV1-M probe | 91, 100, 109, 118, 127, 136 |
|  | (+complementary sequences thereof) |
| HIV1-O forward primer | 139, 148, 157, 167 |
| HIV1-O reverse primer | 170, 179, 189 |
| HIV1-O probe | 190 to 194 |
|  | (+complementary sequences thereof) |
| HIV2 forward primer | 221, 249 |
| HIV2 reverse primer | 276, 287, 296 |
| HIV2-A probe | 297 to 299 |
|  | (+complementary sequences thereof) |
| HIV2-B probe | 300 to 303 |
|  | (+complementary sequences thereof) |

In a preferred embodiment, the invention provides the following oligonucleotides:

| possible use | SEQ ID NO: |
| --- | --- |
| HIV1-M loop forward primer | 14, 15 |
| HIV1-M loop reverse primer | 82 |
| HIV1-M beacon probe | 100, 109, 127, 136 |
|  | (+complementary sequences thereof) |
| HIV1-O loop forward primer | 167 |
| HIV1-O loop reverse primer | 189 |
| HIV1-O beacon probe | 191, 192, 194 |
|  | (+complementary sequences thereof) |
| HIV2 loop forward primer | 249 |
| HIV2 loop reverse primer | 287, 296 |
| HIV2-A beacon probe | 298-299 |
|  | (+complementary sequences thereof) |
| HIV2-B beacon probe | 301-303 |
|  | (+complementary sequences thereof) |

In a preferred embodiment, any nucleotide according to the invention can be fluorescently labelled.

In another aspect, the invention provides a set of oligonucleotides suitable for HIV detection.

In one embodiment, the invention provides a set of oligonucleotides suitable for HIV1-M detection.

In a preferred embodiment, the invention provides a set of oligonucleotides suitable for HIV1-M detection comprising:
   at least one oligonucleotide (primer) selected from the group consisting in SEQ ID NO: 6, 9, 12, 14, 15; and/or
   at least one oligonucleotide (primer) selected from the group consisting in SEQ ID NO: 24, 52, 82; and/or
   at least one oligonucleotide (probe) selected from the group consisting in SEQ ID NO: 91, 100, 109, 118, 127, 136, and the sequences which are complementary to one of SEQ ID NO: 91, 100, 109, 118, 127, 136, over the entire length of this SEQ ID NO.

The possible combinations of oligonucleotides are thus as follows:

| SEQ ID NO: | 6 | 9 | 12 | 14 | 15 |
|---|---|---|---|---|---|
| 24 | X | X | X | X | X |
| 52 | X | X | X | X | X |
| 82 | X | X | X | X | X | wherein X indicates that the oligonucleotides can be combined with each other as a pair (primer pair), and that each primer pair can in addition be used in combination with any one of the oligonucleotides (probes) selected from the group consisting of:
   SEQ ID NO: 91, 100, 109, 110, 118, 127, 136, and the complementary sequences thereof.

In a further aspect, the invention provides a set of oligonucleotides suitable for HIV1-O detection.

In a preferred embodiment, the invention provides a set of oligonucleotides suitable for HIV1-O detection, comprising:
   at least one oligonucleotide (primer) selected from the group consisting in SEQ ID NO: 139, 148, 157, 167; and/or
   at least one oligonucleotide (primer) selected from the group consisting in SEQ ID NO: 170, 179, 189; and/or
   at least one oligonucleotide (probe) selected from the group consisting in SEQ ID NO: 190 to 194, and the sequences which are complementary to one of SEQ ID NO: 190-194, over the entire length of this SEQ ID NO.

The possible combinations of oligonucleotides are thus as follows:

| SEQ ID NO: | 170 | 179 | 189 |
|---|---|---|---|
| 139 | X | X | X |
| 148 | X | X | X |
| 157 | X | X | X |
| 167 | X | X | X | wherein X indicates that the oligonucleotides can be combined with each other as a pair (primer pair), and that each primer pair can in addition be used in combination with any one of the oligonucleotides (probes) selected from the group consisting of:
   SEQ ID NO: 190, 191, 192, 193, 194, and the complementary sequences thereof.

In a further aspect, the invention provides a set of oligonucleotides suitable for HIV2-A detection.

In a preferred embodiment, there is provided a set of oligonucleotides suitable for HIV2-A detection, comprising:
   at least one oligonucleotide (primer) selected from the group consisting in SEQ ID NO: 221, 249; and/or
   at least one oligonucleotide (primer) selected from the group consisting in SEQ ID NO: 276, 287, 296; and/or
   at least one oligonucleotide (probe) selected from the group consisting in SEQ ID NO: 297 to 299 and the sequences which are complementary to one of SEQ ID NO: 297-299 other the entire length of this SEQ ID NO.

The possible combinations of oligonucleotides are thus as follows:

| SEQ ID NO: | 221 | 249 |
|---|---|---|
| 276 | X | X |
| 287 | X | X |
| 296 | X | X | wherein X indicates that the oligonucleotides can be combined with each other as a pair (primer pair), and that each primer pair can in addition be used in combination with any one of the oligonucleotides (probes) selected from the group consisting of:
   SEQ ID NO: 297, 298, 299 and the complementary sequence thereof.

In a further aspect, the invention provides a set of oligonucleotides suitable for HIV2-B detection.

In a preferred embodiment, there is provided a set of oligonucleotides suitable for HIV2-B detection, comprising:
   at least one oligonucleotide (primer) selected from the group consisting in SEQ ID NO: 221, 249; and/or
   at least one oligonucleotide (primer) selected from the group consisting in SEQ ID NO: 276, 287, 296; and/or
   at least one oligonucleotide (probe) selected from the group consisting in SEQ ID NO: 300 to 303, and the sequences which are complementary to one of SEQ ID NO: 300-303, over the entire length of this SEQ ID NO.

The possible combinations of oligonucleotides are thus as follows:

| SEQ ID NO: | 221 | 249 |
|---|---|---|
| 276 | X | X |
| 287 | X | X |
| 296 | X | X | wherein X indicates that the oligonucleotides can be combined with each other as a pair (primer pair), and that each primer pair can in addition be used in combination with any one of the oligonucleotides (probes) selected from the group consisting of:
   SEQ ID NO: 300, 301, 302, 303, and the complementary sequences thereof.

In a further aspect, the invention provides a set of oligonucleotides suitable for HIV multiplex detection.

In a preferred embodiment, there is provided a set of oligonucleotides suitable for HIV detection, preferably multiplex detection, comprising:
   at least one oligonucleotide selected from the group consisting in SEQ ID NO: 91, 100, 109, 118, 127, 136, and the complementary sequences thereof; and/or at least one oligonucleotide selected from the group consisting in SEQ ID NO: 190 to 194, and the complementary sequences thereof; and/or at least one oligonucleotide selected from the group consisting in SEQ ID NO: 297 to 299, and the complementary sequences thereof; and/or at least one oligonucleotide selected from the group consisting in SEQ ID NO: 300 to 303, and the complementary sequences thereof; and/or combinations thereof.

Such a set of oligonucleotides according to the invention may thus comprise any combination thereof of 2, 3, 4, 5 and more of said oligonucleotides.

In a preferred embodiment, such a set of oligonucleotides can be a combination of probes, e.g. a combination of an HIV1-M probe and an HIV1-O probe:

| SEQ ID NO: | 91 | 100 | 109 | 118 | 127 | 136 |
|---|---|---|---|---|---|---|
| 190 | X | X | X | X | X | X |
| 191 | X | X | X | X | X | X |
| 192 | X | X | X | X | X | X |
| 193 | X | X | X | X | X | X |
| 194 | X | X | X | X | X | X |

(X = possible combination, optionally with any further probe(s), eg HIV2-A or HIV2-B probes)

In another embodiment, such a set of oligonucleotides can be a combination of probes, e.g. a combination of an HIV2-A probe and an HIV2-B probe:

| SEQ ID NO: | 297 | 298 | 299 |
|---|---|---|---|
| 300 | X | X | X |
| 301 | X | X | X |
| 302 | X | X | X |
| 303 | X | X | X |

Further possibilities include:

| SEQ ID NO: | 91 | 100 | 109 | 118 | 127 | 136 |
|---|---|---|---|---|---|---|
| 297 | X | X | X | X | X | X |
| 298 | X | X | X | X | X | X |
| 299 | X | X | X | X | X | X |
| 300 | X | X | X | X | X | X |
| 301 | X | X | X | X | X | X |
| 302 | X | X | X | X | X | X |
| 303 | X | X | X | X | X | X |

(X = possible combination, optionally with any further probe(s), eg for HIV1-O)

| SEQ ID NO: | 190 | 191 | 192 | 193 | 194 |
|---|---|---|---|---|---|
| 297 | X | X | X | X | X |
| 298 | X | X | X | X | X |
| 299 | X | X | X | X | X |
| 300 | X | X | X | X | X |
| 301 | X | X | X | X | X |
| 302 | X | X | X | X | X |
| 303 | X | X | X | X | X |

(X = possible combination, optionally with any further probe(s), eg for HIV1-M)

In a preferred embodiment, in any set of oligonucleotides according to the invention, at least one of said oligonucleotides is fluorescently labelled.

There is further provided an amplicon obtainable by means of at least one oligonucleotide according to the invention, and/or at least one set of nucleotides according to the invention.

There is more particularly provided an amplicon obtainable by amplification from a HIV-containing sample with a pair of primers selected from:

a primer of SEQ ID NO: 9, 12, 14 or 15, and a primer of SEQ ID NO: 24, 52 or 82; or a primer of SEQ ID NO: 148, 157 or 167, and a primer of SEQ ID NO: 170, 179 or 189; or a primer of SEQ ID NO: 221 or 249, and a primer of SEQ ID NO: 276, 287 or 296; or a primer of SEQ ID NO: 6, and a primer of SEQ ID NO: 24, 52 or 82; or a primer of SEQ ID NO: 139, and a primer of SEQ ID NO: 170, 179 or 189.

There is also provided an amplicon which has a nucleotide length identical to the nucleotide length of one of the reference template sequences of the invention (i.e. SEQ ID NO: 2, 4, 5, 1 or 3 and the above-mentioned fragments thereof), and which comprises a sequence having a percentage of nucleotide identity of at least 90%, preferably of at least 91%, most preferably of at least 92%, most preferably of at least 93%, most preferably of at least 94%, most preferably of at least 95%, most preferably of at least 96%, most preferably of at least 97%, most preferably of at least 98%, most preferably of at least 99%, most preferably of 100%, with a probe sequence, over the entire length of this probe sequence, wherein this probe sequence is one of the following: SEQ ID NO: 91, 100, 109, 118, 127, 136, 190, 191, 192, 193, 194, 297, 298, 299, 300, 301, 302, 303, and the sequences which are complementary to these SEQ ID NO: over the entire length of these SEQ ID NO.

An amplification composition comprising such an amplicon is also encompassed by the present invention.

It is another object of the present invention to provide with a kit.

In a preferred embodiment, said kit comprises at least one oligonucleotide (primer or probe) according to the invention, as described above.

In another embodiment, said kit comprises at least one primer pair according to the invention, as described above.

In yet another embodiment, said kit comprises at least a set of oligonucleotides according to the invention, for example at least one plurality of probes according to the invention, as described above.

In the kit according to the invention, the oligonucleotides (primers, probes) can be either kept separately, or partially mixed, or totally mixed.

Said oligonucleotides can be provided under dry form, or solubilized in a suitable solvent, as judged by the skilled person. Suitable solvents include TE, PCR-grade water, and the like.

In a preferred embodiment, the kit according to the invention can also contain further reagents suitable for a PCR step, possibly including reagents suitable for an RT-PCR step.

Such reagents are known to those skilled in the art, and include water, like nuclease-free water, RNase free water, DNAse-free water, PCR-grade water; salts, like magnesium, potassium; buffers such as Tris; enzymes, including polymerases, such as Taq, Vent, Pfu (all of them Trade-Marks), activable polymerase, reverse transcriptase, and the like; nucleotides like deoxynucleotides, dideoxunucleotides, dNTPs, dATP, dTTP, dCTP, dGTP, dUTP; other reagents, like DTT and/or RNase inhibitors; and polynucleotides like polyT, polydT, and other oligonucleotides, e.g. primers.

In another preferred embodiment, the kit according to the invention comprises PCR controls. Such controls are known in the art, and include qualitative controls, positive controls, negative controls, internal controls, quantitative controls, internal quantitative controls, as well as calibration ranges. The internal control for said PCR step can be a template which is unrelated to the target template in the PCR step. Such controls also may comprise control primers and/or control probes. For example, in the case of HIV detection, it is possible to use as an internal control, a polynucleotide chosen within a gene whose presence is excluded in a sample originating from a human body (for example, from a plant gene), and whose size and GC content is equivalent to those from the target sequence.

In a preferred embodiment, the kit according to the invention contains means for extracting and/or purifying nucleic acid from a biological sample, e.g. from blood, serum, plasma. Such means are well known to those skilled in the art. In a preferred embodiment, the kit according to the invention contains instructions for the use thereof. Said instructions can advantageously be a leaflet, a card, or the like. Said instructions can also be present under two forms: a detailed one, gathering exhaustive information about the kit and the use thereof, possibly also including literature data; and a quick-guide form or a memo, e.g. in the shape of a card, gathering the essential information needed for the use thereof.

In a preferred embodiment, said kit is a diagnostics kit, especially an in vitro diagnostics kit, i.e. an HIV diagnostics kit.

The present invention also relates to the field of diagnostics.

The oligonucleotides according to the present invention, and as described above, can be used for the in vitro diagnostics of HIV types and subtypes. In particular, the primers and probes according to the invention can be used for in vitro typing, sub-typing, and quantification of HIV nucleic acids present in an in vitro sample, for instance, in a patient's blood, plasma and/or serum, or in a cell culture supernatant.

It is also an object of the present invention to provide with a method to detect HIV nucleic acid presence in a sample.

In one embodiment, said method comprises the step of providing with at least one sample suspected of comprising at least one target template from at least one HIV type and/or sub-type and/or isolate.

By nucleic acid, we hereby understand any nucleic acid: it can be synthetic or not, recombinant or naturally occurring, linear or circular. This includes DNA and RNA. The nucleic acid can be either single stranded or double stranded or even triple stranded. It can stem from various biological sources, such as micro organisms (bacteria, yeasts, and the like), or higher organisms, like mammal cells. Said nucleic acid can also be of viral nature, e.g. retroviral nature, like HIV's. The nucleic acid can also comprise total DNA, total RNA, genomic DNA, mitochondrial DNA, plasmidic DNA, BAC DNA, and mixtures thereof. Moreover, the nucleic acid can assume various states of purity.

By sample, we hereby understand any kind of sample, naturally occurring or not. Preferably, said sample is from biological origin. Said sample may also stem from a cell culture supernatant. In a preferred embodiment, said sample derives from blood. More preferably, said nucleic acid containing sample derives from serum and/or plasma. Said sample might also result from a preliminary step. For instance, said sample might be obtainable via a purification and/or extraction procedure, e.g. from a blood sample. In particular, said sample may result from a separation and/or purification and/or extraction process carried out on a biological sample. Said sample can also be a control sample. Control samples include samples as qualitative control, positive control, negative control, quantitative control, and calibrating control. Said control can be internal as well as external. Any sample according to the present invention can be present several times. For instance, said sample can be provided as duplicate, as triplicate, as quadruplicate . . . as multiplicate, which is advantageous in the case of quantitative experiments.

The skilled person is familiar with the notion of target template. Said target template can be any nucleic acid, whose presence is to be assessed in said method. Said target template is possibly, but not necessarily, the nucleic acid to be amplified in said method (PCR amplicon).

Said method may comprise the step of providing with at least one nucleic acid-containing sample suspected of comprising at least one target template from at least one HIV type and/or sub-type.

In one aspect of the invention, said method comprises the step of providing with at least one oligonucleotide according to the invention (e.g. PCR primer and/or probe) and/or at least one set of nucleotides (e.g. a primer pair) according to the invention.

In one embodiment, said method comprises the step of contacting said nucleic acid-containing sample with at least one oligonucleotide according to the invention and/or at least one set of nucleotides according to the invention, under conditions enabling the annealing of said primer and/or said primer pair and/or said probe onto said template.

In another aspect, said method comprises the step of observing or detecting the presence of an annealed product, thereby revealing the initial presence of an HIV nucleic acid in said sample.

It is a further object of the invention to provide with a method for the quantitative specific detection of HIV types and sub-types in a sample, preferably through real-time quantitative multiplex PCR analysis.

In one embodiment, said method comprises the step of providing with at least one sample suspected of comprising at least one target template from at least one HIV type and/or sub-type.

In another preferred embodiment, said method comprises the step of providing with at least one oligonucleotide according to the invention (e.g. PCR primer and/or probe) and/or at least one set of nucleotides according to the invention (e.g. primer pair).

In a preferred embodiment, said probe is suitable for the detection of a putative HIV amplicon obtainable with said primer pair.

In a preferred embodiment according to the invention, spectral properties of said probes can be chosen as to not interfere with each other. In particular, when probes are used in multiplex, each single probe can have its own fluorophore being spectrally significantly different from each other, i.e. the absorption/emission spectra are essentially non-overlapping. This advantageously allows for low-noise multiplex detection for all single probes, making sure that individual signals do not interfere with each other in detection. Examples of dyes which can be used together in multiplex include Fam with Tamra, Fam with Tamra and Texas Red.

In another preferred embodiment, said method comprises the step of contacting said sample, in presence of said oligonucleotide(s) and/or primer(s) and/or pair(s) or primers and/or probe(s) and/or set(s) of oligonucleotides and possibly in the presence of suitable reagents, to the conditions suitable for the PCR amplification of said target template with said primer pair(s) and/or set(s).

Said PCR amplification can be any PCR reaction, including RT-PCR. Such suitable reagents are known in the art, and examples thereof include water, like nuclease-free water, RNase free water, DNAse-free water, PCR-grade water; salts, like magnesium, potassium; buffers such as Tris; enzymes, including polymerases, such as Taq, Vent, Pfu (all of them Trade-Marks), activable polymerase, reverse transcriptase, and the like; nucleotides like deoxynucleotides, dideoxynucleotides, dNTPs, dATP, dTTP, dUTP, dCTP, dGTP; other reagents, like DTT and/or RNase inhibitors; and polynucleotides like polyT, polydT. Advantageously according to the invention, at least part of these reagents can be used as a pre-mix. The amounts thereof to be used are known to those skilled in the art.

In a preferred embodiment, the primers according to the invention are used in a final concentration range 100-200 nM. Typically, said primers can be used at a final concentration range 200-1500 nM, preferably 250-1000 nM, more preferably 500-1000 nM, even more preferably 600-1000 nM.

Probe concentration in a PCR reaction can be optimized, typically by varying the final concentration from 50 nM to 1000 nM. In a preferred embodiment, the probes according to the invention are used at a final concentration range 50-1000 nM, preferably 100-800 nM, more preferably 100-600 nM, even more preferably 200-600 nM.

Said conditions are known to those skilled in the art. They include temperature conditions, in particular thermal cycling conditions, e.g. temperature, duration, number, heating rate of the cycles. In a preferred embodiment, said temperature conditions include conditions suitable for an RT-PCR. In another preferred embodiment, said conditions include conditions suitable for a QPCR. In yet another preferred embodiment, said conditions include conditions suitable for a quantitative RT-PCR.

In another embodiment, said method comprises the step of bringing said sample, in the presence of said probe(s) under conditions suitable for the annealing of said probe to said putative amplicon.

In yet another preferred embodiment, said method comprises the step of detecting at least once, preferably real-time, potential amplification products, i.e. whether said probe(s) meet(s) said amplicon to anneal with, preferably for each sample. This advantageously allows for the assessment of the presence of said HIV type and/or sub-type. This can be advantageously achieved by fluorescence intensity measurements. Fluorescence measurement procedures are known in the art. Briefly, the sample is illuminated at around the excitation wavelength of the fluorophore, and emission intensity is measured.

In another embodiment, said method comprises the step of measuring at least once, preferably real-time, the amount of said probe annealed to said amplicon. This can be advantageously achieved by fluorescence intensity measurements. Fluorescence measurement procedures are known in the art. Briefly, the sample is illuminated at around the excitation wavelength of the fluorophore, and emission intensity is measured In another preferred embodiment, said method comprises the step of estimating at least once the number of target template copies initially present in said sample. The skilled person would know how to carry out such a step. For example, this can be advantageously performed having used calibration standards and/or internal controls. Preferably, this step includes the determination of the so-called threshold cycle (CT) for each sample, which correlates to the number of target template copies initially present in said sample.

In a preferred embodiment, at least one step, preferably several steps, more preferably most of the steps of said method can be carried out in a PCR plate. Suitable such PCR plates are known in the art. They include 24-well plates, 48-well plates, 96-well-plates, and 284-well plates. This advantageously ensures that samples can be processed in parallel in said steps. In addition, this allows for high throughput screening, which advantageously saves time. In another preferred embodiment, at least one step, preferably several steps, more preferably most steps of said method can be carried out in a thermal cycler. Such thermal cycler might be equipped for real-time fluorescence intensity measurements, in which case said plates can advantageously be of optical-grade.

This application also relates to the amplification of HIV nucleic acids with at least one oligonucleotide and/or PCR primer and/or at least one PCR primer pair and/or at least one probe and/or at least one set of nucleotides according to the invention.

The skilled person can appreciate that the present invention can incorporate any number of the preferred features described above. All citations mentioned herein are hereby incorporated by reference in their entirety.

Other embodiments of the present invention are not presented here, which are obvious to those skilled in the art, and thus are within the scope and the spirit of the present invention. In particular, although being suitable for detection via multiplex and/or real-time protocols, the methods, processes, polynucleotides, oligonucleotides, sets of oligonucleotides, amplicons, and kits of the present invention are obviously also suitable for simplex protocols, qualitative protocols, quantitative protocols, end-point detection protocols, and combinations thereof.

The advantages of the products, processes and methods according to the invention will become apparent from the following examples, which are given below as mere illustrations, and are non limitative.

FIGS. 5A and 5B illustrate HIV1/HIV2 multiplex detection according to the present invention (see example 4 below).

FIGS. 6A, 6B and 6C illustrate an HIV2/internal control assay according to the present invention (see example 5 below).

FIGS. 7 to 21 illustrate sequences according to the present invention.

EXAMPLES

Example 1

Figure 1A:
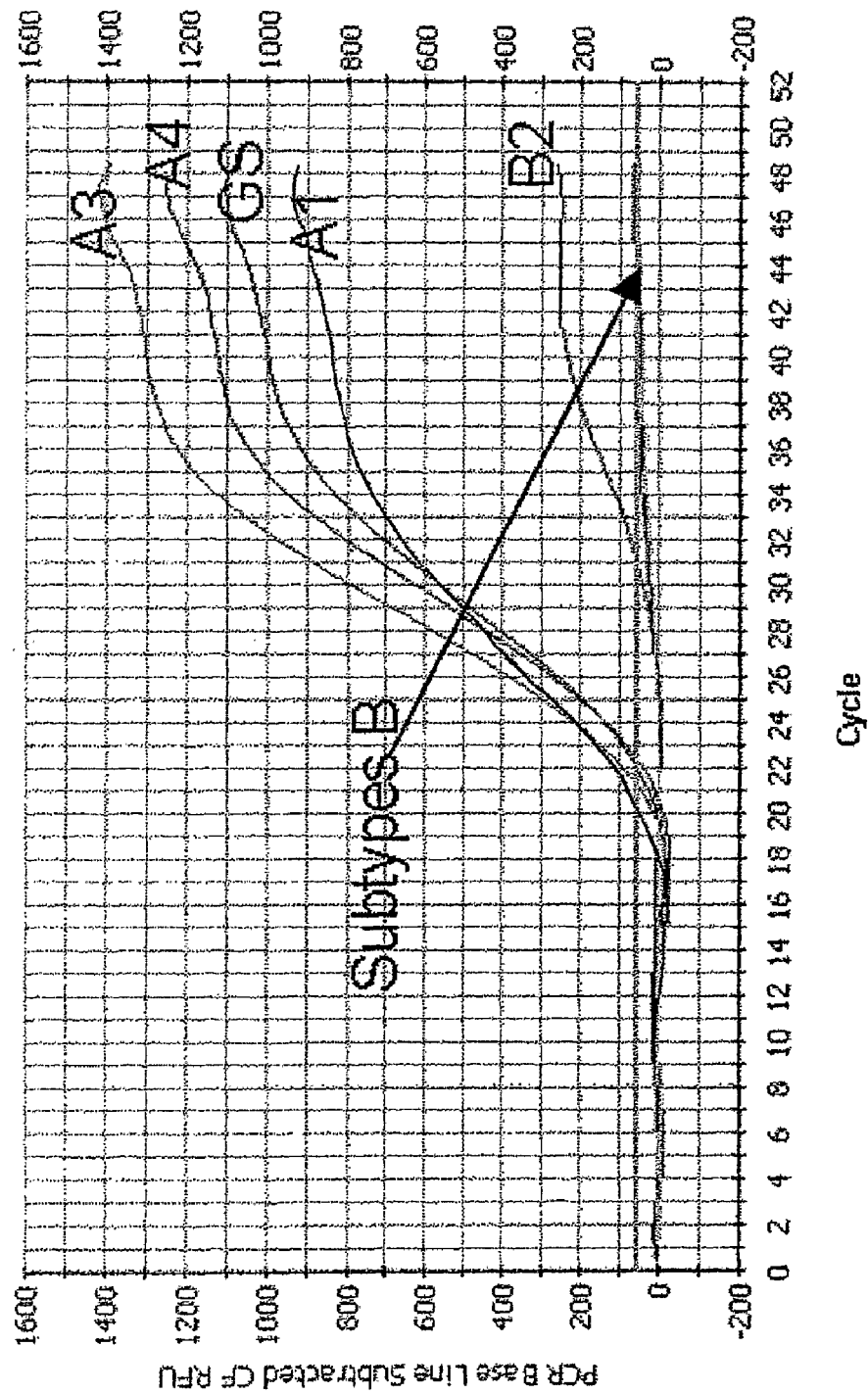
FIGS. 1A, 1B, 2A, 2B and 3 illustrate HIV2-A and HIV2-B detection according to the present invention (see example 1 below).

HIV2 Detection (Sub-Types A and B) (FIGS. 1A, 1B, 2A, 2B and 3)

This example illustrates that the HIV2 primers and probes of the invention allow for RT-PCR specific real-time detection of HIV2 sub-types A and B.

This example involves the use of one pair of HIV2 primers, and two different HIV2 probes. One probe is an HIV2-A probe (sub-type A probe), and the other one is an HIV2-B probe (sub-type B probe). These primers and probes target a 147 bp sequence in HIV2 isolates.

They have the following sequences:

```
HIV2 forward primer (H2A3f, SEQ ID NO: 195):
AGGAAGRCARACAGCACTCTTC
with R = A/G (Tm = 66° C.)

HIV2 reverse primer (H2A3r, SEQ ID NO: 250):
GGTACTCCRAAGGGGTTTGTTCTAT
with R = A/G (Tm = 65°)
```

As already mentioned, R corresponds to an A or G, so that there are 4 forms for the forward primer (AA, AG, GA and GG) et 2 forms for the reverse primer (AG or GA).

```
HIV2-A probe (HIV2-A probe, SEQ ID NO: 297):
GGCCAATAACACACTTGCACACA

HIV2-B probe (HIV2-B probe, SEQ ID NO: 300):
GCCTATCACACACCTGCACACA
```

Each of these probes is used as a molecular beacon in this example. The target-unrelated beacon arms which have been added at each end of each probe are shown underlined (FAM=fluorophore; DQ=Dark Quencher).

```
HIV2-A probe in molecular beacon format
(HIV2-A beacon probe, SH2A9a, SEQ ID NO: 298):
FAM-AGCGCGGCCAATAACACACTTGCACACAGCGCT-DQ H1V2-B probe in molecular beacon format
(HIV2-B beacon probe, SH2A1b, SEQ ID NO: 301):
FAM-AGCGCGCCTATCACACACCTGCACACAGCGCT-DQ
```

Three series of real-time quantitative amplification experiments are performed on a panel of HIV2-positive plasma samples (HIV2-A positive HIV2-B negative samples and HIV2-B positive HIV2-A negative samples):
  a) HIV2 primer pair+HIV2-A beacon probe (H2A3f, H2A3r, SH2A9a, SEQ ID NO: 195, 250, 298),
  b) HIV2 primer pair+HIV2-B beacon probe (H2A3f, H2A3r, SH2A1b, SEQ ID NO: 195, 250, 301),
  c) HIV2 primer pair+HIV2-A beacon probe+HIV2-B beacon probe (H2A3f, H2A3r, SH2A9a, SH2A1b, SEQ ID NO: 195, 250, 298, 301).

Details of the procedure are as follows:
Panel of HIV2-positive samples: HIV2-A positive HIV2-B negative plasma samples (sub-type A samples) and HIV2-B positive HIV2-A negative plasma samples (sub-type B samples) are obtained from infected patients (Centre Hospitalier Bichat, Laboratory of Virology, Assistance Publique—Hôpitaux de Paris, France);
Negative controls: HIV2-negative plasma;
Nucleic acid extraction: Kit Qiagen QiaAmp Viral RNA (reference 52904) used in accordance with the manufacturer's recommendations (volume of sample for extraction=140 microliters);
Primer pair: 1 microM each per reaction (SEQ ID NO: 11, 12);
Probes: FAM-Dark Quencher beacon probes as described above (SEQ ID NO: 298, 301); 0.2 microM each per reaction;
RT-PCR reagents: RNAse-free water, and Qiagen Quanti-Tect Probe RT-PCR kit (Qiagen reference: 204443) used according to the manufacturer's instructions, [$MgCl_2$] =4 mM;
Apparatus: IQ-Cycler Bio-Rad;
Thermal cycling:
  30' at 42° C. (RT step),
  15' at 95° C. (polymerase activation step),
  (30" at 94° C.-30" at 55° C.-30" at 72° C.)×50, +4° C.

The panel of sub-type A samples and sub-type B samples are submitted to nucleic acid extraction and RT-PCR amplification using the HIV2 primer pair together with either only one of the probes (experiments a) and b)), or both probes (experiment c)).

Interpretation of the results: for each assay, one determines a threshold cycle (Ct) which is the level of fluorescence that is considered to be significantly above the background level of fluorescence measured in the early cycles of the amplification. The Ct value is inversely proportional to the concentration of target: the lower the Ct, the higher the concentration of target.

In the following tables, CT=Threshold Cycle; RFU max=maximal Relative Fluorescence Units observed at the end of the PCR run; CTL-=negative control; N/A=sample whose level of fluorescence is below the background level.

TABLE 1

Results obtained with HIV2 primer pair + HIV2-A molecular beacon probe in experiment a) (H2A3f, H2A3r, SH2A9a, SEQ ID NO: 195, 250, 298).

| | | | |
|---|---|---|---|
| Sub-type A Samples dilution | A1 1/10 | CT | 20.2 |
| | | RFUmax | 916 |
| | GS 1/800 | CT | 22 |
| | | RFUmax | 1078 |
| | A3 1/10 | CT | 21.2 |
| | | RFUmax | 1382 |
| | A4 1/10 | CT | 22.4 |
| | | RFUmax | 1221 |
| Sub-type B Samples dilution | B1 1/10 | CT | 42.9 |
| | | RFUmax | 67 |
| | B2 1/10 | CT | 30.9 |
| | | RFUmax | 265 |
| | B3 1/10 | CT | N/A |
| | | RFUmax | 50 |
| | B4 1/10 | CT | 37.8 |
| | | RFUmax | 52 |
| Negative control | CTL- | CT | N/A |
| | | RFU max | N/A |

Figure 1B:
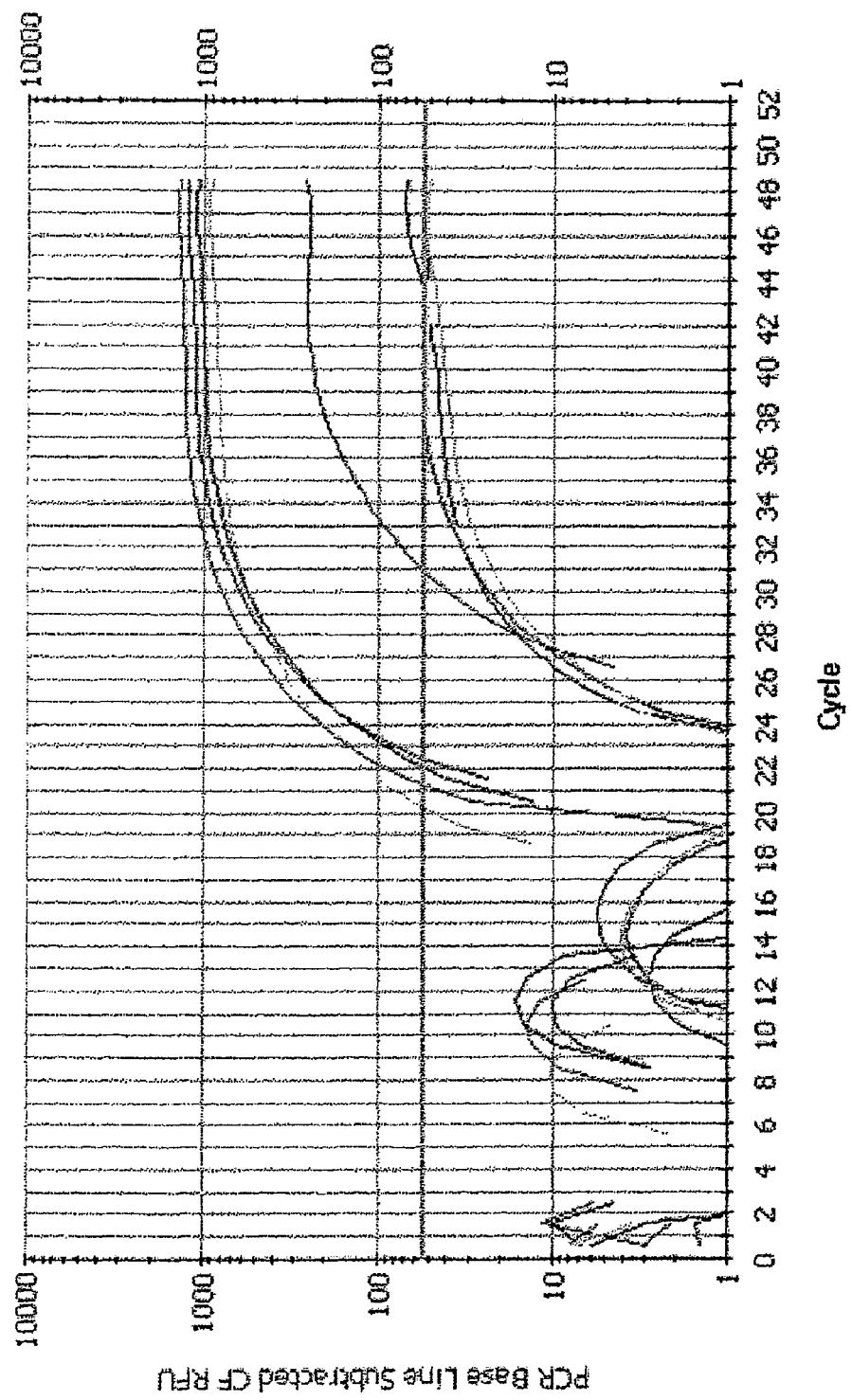

These results are illustrated by FIGS. 1A and 1B.

Advantageously according to the invention, the HIV2-A probe (SH2A9a, SEQ ID NO: 298) allows for targeted detection of sub-type A positive samples in combination with the HIV2 primers according to the invention (H2A3f, H2A3r, SEQ ID NO: 195, 250), without cross-detection of sub-type B positive samples (see Table 1, and FIGS. 1A and 1B).

TABLE 2

Results obtained with HIV2 primer pair + HIV2-B probe in experiment b) (H2A3f, H2A3r, SH2A1b, SEQ ID NO: 195, 250, 301).

| | | | | |
|---|---|---|---|---|
| Sub-type A Samples dilution | A1 1/10 | CT | 35.1 | 39.5 |
| | | RFUmax | 84 | 53 |
| | GS 1/800 | CT | 36.8 | 40.5 |
| | | RFUmax | 81 | 57 |
| | A3 1/10 | CT | 26.9 | 26.7 |
| | | RFUmax | 159 | 137 |
| | A4 1/10 | CT | 44 | N/A |
| | | RFUmax | 55 | — |
| Sub-type B samples | B1 1/10 | CT | 21.4 | 21.5 |
| | | RFUmax | 1018 | 996 |
| | B2 1/10 | CT | 29.6 | 29.9 |
| | | RFUmax | 286 | 292 |
| | B3 1/10 | CT | 26.3 | 27.2 |
| | | RFUmax | 768 | 690 |
| | B4 1/10 | CT | 27 | 27.1 |
| | | RFUmax | 832 | 779 |

TABLE 2-continued

Results obtained with HIV2 primer pair + HIV2-B probe in experiment b) (H2A3f, H2A3r, SH2A1b, SEQ ID NO: 195, 250, 301).

| Negative control | CTL- | CT | N/A | N/A |
|---|---|---|---|---|
| | | RFU max | N/A | N/A |

Figure 2A:
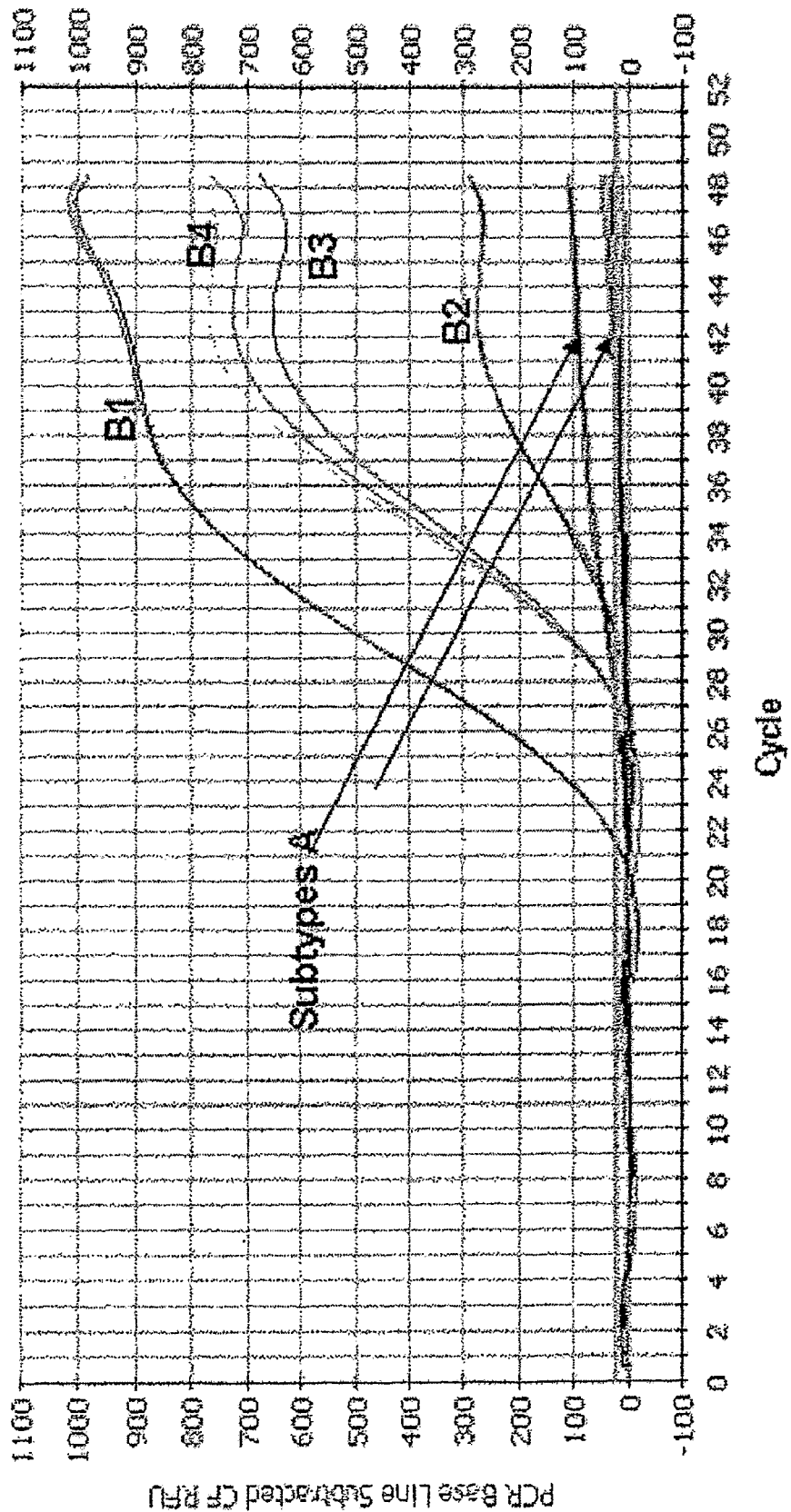
Figure 2B:
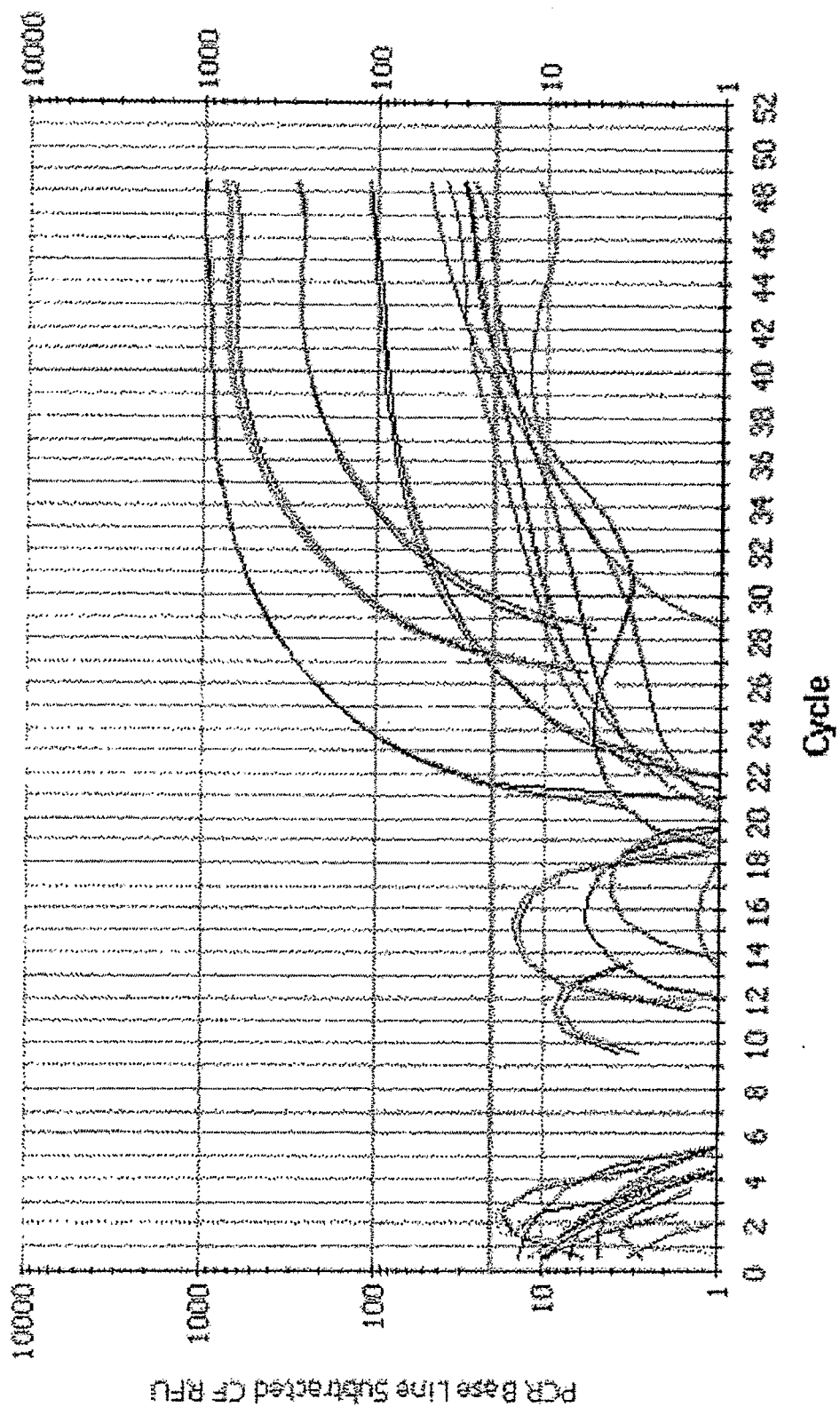

These results are illustrated by FIGS. 2A and 2B.

Advantageously according to the invention, the HIV2-B probe (SH2A1b, SEQ ID NO: 301) allows for targeted detection of sub-type B positive samples in combination with the HIV2 primers (H12A3r, H2A3f, SEQ ID NO: 195, 250) of the invention, without cross-detection of sub-type A positive samples (see Table 2, and FIGS. 2A and 2B).

TABLE 3

Results obtained with HIV2 primer pair + HIV2-A probe + HIV2-B probe in experiment c) (H2A3f, H2A3r, SH2A9a, SH2A1b, SEQ ID NO: 195, 250, 298, 301).

| Sub-type A Samples dilution | A1 1/10 | CT | 20.3 | 20.6 |
|---|---|---|---|---|
| | | RFU max | 1673 | 1550 |
| | GS 1/800 | CT | 23.7 | 23.9 |
| | | RFU max | 1709 | 1580 |
| | A3 1/10 | CT | 21.4 | 21.5 |
| | | RFU max | 2439 | 2201 |
| | A4 1/10 | CT | 22.6 | 22.8 |
| | | RFU max | 1974 | 1911 |
| Sub-type B samples | B1 1/10 | CT | 23.3 | 23.6 |
| | | RFU max | 1197 | 1122 |
| | B2 1/10 | CT | 30.2 | 30.5 |
| | | RFU max | 635 | 672 |
| | B3 1/10 | CT | 28.6 | 28.7 |
| | | RFU max | 814 | 834 |
| | B4 1/10 | CT | 28.7 | 28.8 |
| | | RFU max | 837 | 841 |
| Negative control | CTL- | CT | N/A | N/A |
| | | RFU max | N/A | N/A |

Figure 3:
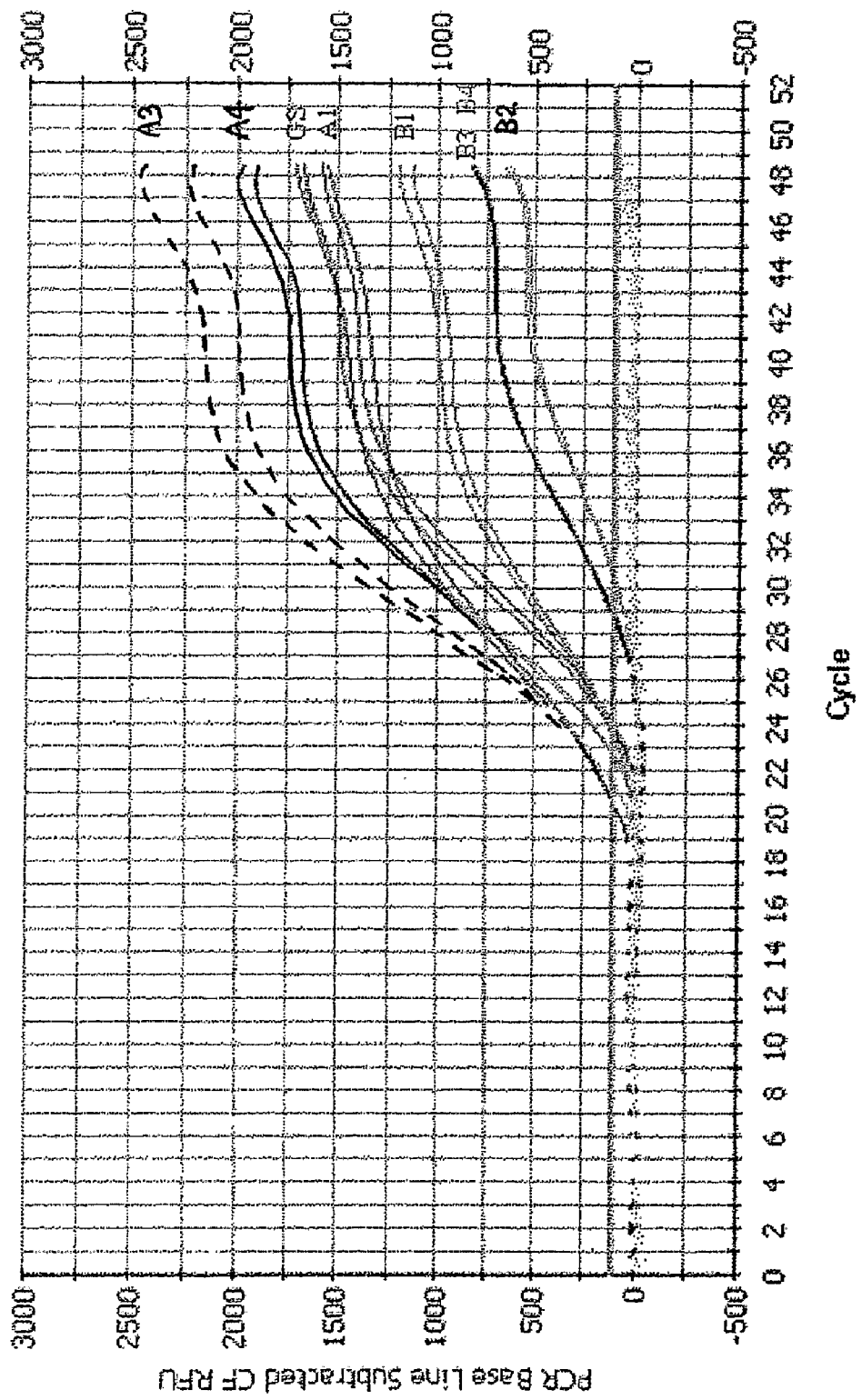

These results are illustrated by FIG. 3.

As a remarkable feature of the invention, the HIV2-A probe (SH2A9a, SEQ ID NO: 298) and the HIV2-B probe (SH2A1b, SEQ ID NO: 301) can be used simultaneously (see Table 3 and FIG. 3) and allow for detection of both sub-types in a one-step multiplex (here duplex) procedure.

As a surprising feature, a synergistic effect is observed for the simultaneous use of both A and B probes (sub-type A probe and sub-type B probe) (duplex protocol), compared to the use of a single probe alone (sub-type A probe or sub-type B probe). The detection signal obtained with a single probe is slightly less accurate than the respectively obtained with both probes, as can be judged from the comparison of the results obtained in experiment a) with those obtained in experiment c) on sub-type A samples, and from the comparison of the results obtained in experiment b) with those obtained on sub-type B samples in experiment c).

The sets of oligonucleotides (primers and probes) according to the invention thus prove an increased specificity when probes are used simultaneously (multiplex, duplex protocol), as a surprising and unexpected synergistic effect Example 2

Figure 4A:
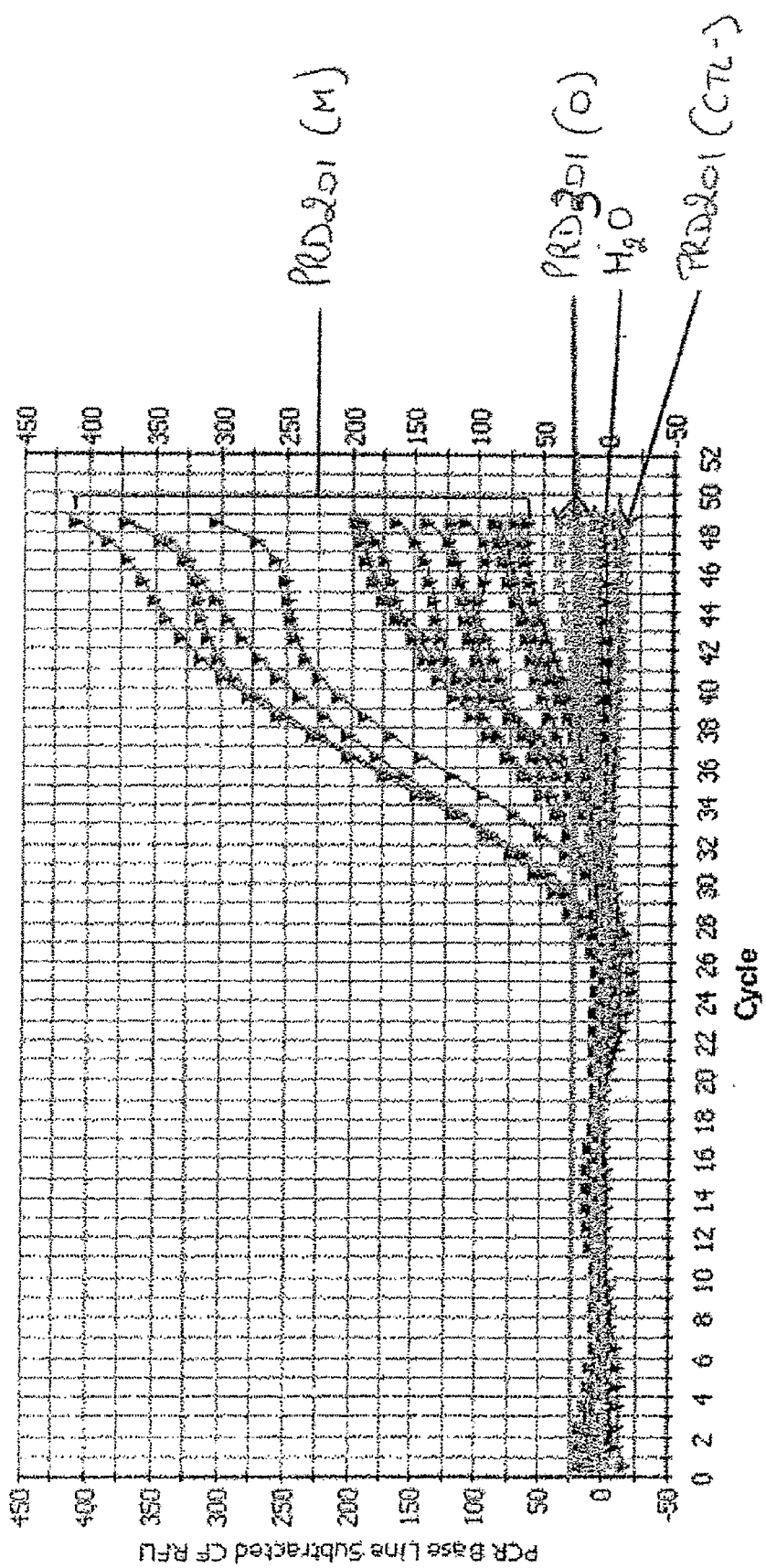
FIGS. 4A and 4B illustrate HIV1-M and HIV1-O detection according to the present invention (see example 2 below).
Figure 4B:
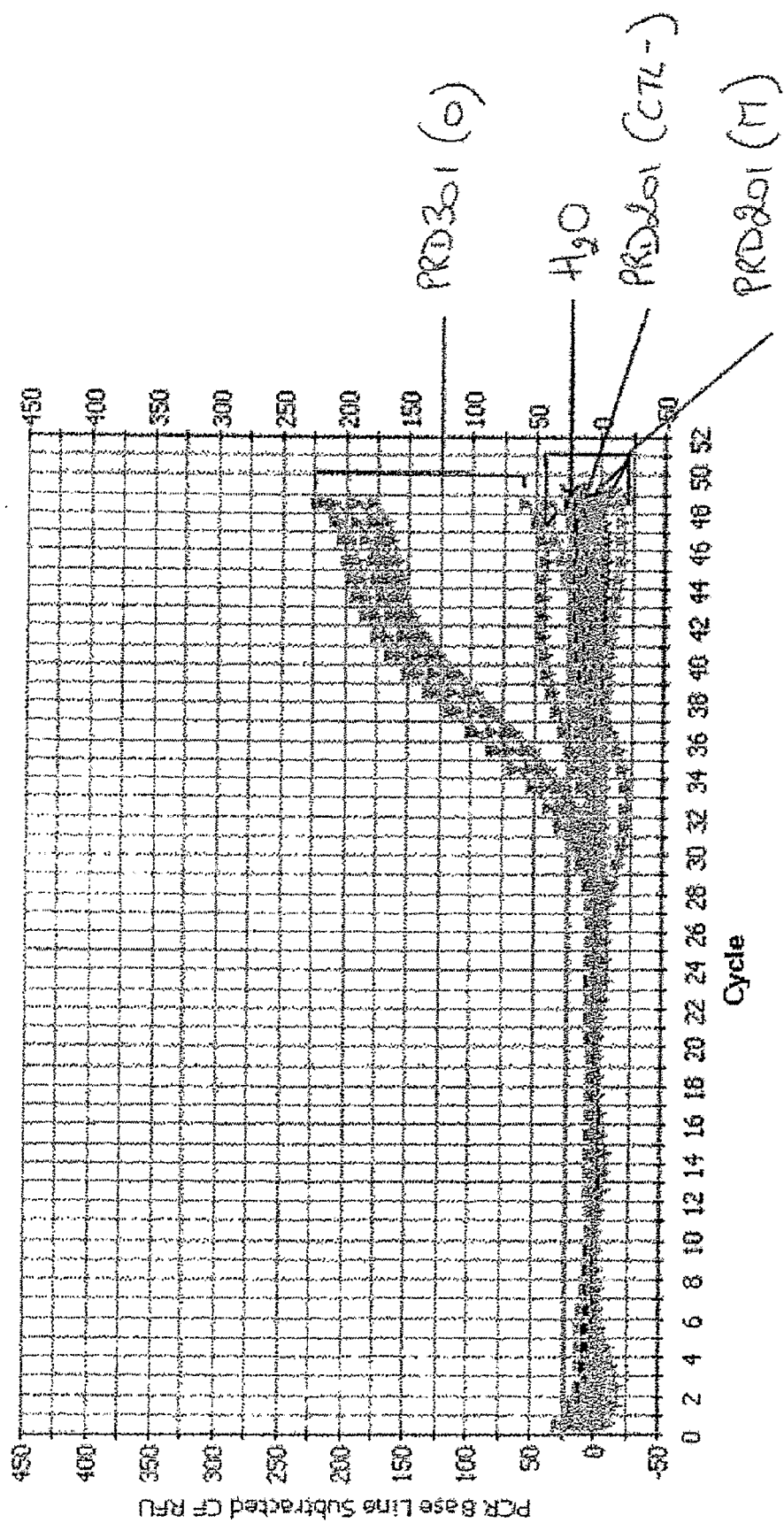

HIV1-M/HIV1-O Primers and Probes (FIGS. 4A and 4B)

In one run, representative reference panels of HIV1-M positive HIV1-O negative serum samples (HIV1-M panel samples) and representative reference panels of HIV1-O positive HIV1-M negative serum samples (HIV1-O panel samples) are subjected to real-time quantitative RT-PCR amplification with the HIV1-M primers (H1B4f, H1B10r, SEQ ID NO: 7, 16) and an HIV1-M probe (SH1BM5, SEQ ID NO: 119) of the invention.

In another run, the same panels are subjected to real-time quantitative RT-PCR amplification with the HIV1-O primers (H1B5f, H1B13r, SEQ ID NO: 140, 168) and a HIV1-O probe (SH1BO2 SEQ ID NO: 191 or SH1BO10 SEQ ID N° 194) of the invention The HIV1 primers and probes have the following sequences:

```
HIV1-M primers:
Forward:
                              (H1B4f, SEQ ID NO: 7)
    TTGGAGAGCAATGGCTAGTGA Reverse:
                              (H1B10r, SEQ ID NO: 16)
    TGTGTGCAATCTAGTTGCCATA HIV1-M probe:
                              (SEQ ID NO: 110)
    ATAGTAGCCAGCTGTGATAAATGTC HIV1-O primers:
Forward:
                              (H1B5f, SEQ ID NO: 140)
    TTGGAGAGCACTAGCTAGTGA Reverse:
                              (HIB13r, SEQ ID NO: 168)
    TGTGTGCAATCTATTTGCCATA HIV1-O probe:
                              (SEQ ID NO: 190)
    GAAATCATTGCTAGTTGTCCTAAATGTCATAT
```

According to the invention, each probe is produced here as a molecular beacon, with "TGCGC" as target-unrelated arm in 5', and with "GCGCA" as target-unrelated arm in 3' (both arms are underlined). The 5'-arm is labelled with a FAM fluorophore, and the 3' arm with a Dark Quencher.

Probe sequences are then the following:

```
HIV1-M probe in a molecular beacon format:
                              (SH1BM5, SEQ ID NO: 119)
FAM-TGCGCATAGTAGCCAGCTGTGATAAATGTCGCGCA-DQ HIV1-O probe in a molecular beacon format:
                              (SH1BO2, SEQ ID NO: 191)
FAM-TGCGCGAAATCATTGCTAGTTGTCCTAAATGTCATATGCGCA-DQ
```

Details of the RT-PCR procedure are as follows:
Panels: BBI Performance Panel reference PRD301 (HIV1-O cultures diluted in human plasma at about $10^5$ copies per mL; sample numbers have the format 301-xx, wherein xx is the sample number) is used as representative HIV1-O panel;

BBI Performance Panel reference PRD201 (HIV1-M cultures diluted in human plasma at about $10^5$ copies per mL; sample numbers have the format 201-yy, wherein yy is the sample number) is used as representative HIV1-M panel;

Negative controls: HIV1 negative plasma;

Extraction: Kit Qiagen QiaAmp Viral RNA (reference 52904) used in accordance with the manufacturer's recommendations (volume of sample for extraction: 140 microliters);

Primer pairs: HIV1-O primer pair (H1B5f, H1B13r, SEQ ID NO: 140, 168) and HIV1-M (H1B4f, H1B10r, SEQ ID NO: 7, 16) primer pair have each been used at 0.6 μM per reaction;

Probes: FAM-Dark Quencher probes (SH1BM5, SH1BO2, SEQ ID NO: 119, 191) at 0.6 μM each per reaction;
RT-PCR reagents: RNAse-free water, and Qiagen Quanti-Tect Probe RT-PCR kit (Qiagen reference: 204443), used according to the manufacturer's instructions, [MgCl$_2$]=4 mM;
Apparatus: IQ-Cycler Bio-Rad;
Thermal cycling:
30' at 42° C.,
15' at 95° C.,
(15" at 94° C.-30" at 55° C.-30" at 72° C.)×50, +4° C.

The same RT-PCR procedure has been followed for both types of amplification experiments.

Interpretation of the results: for each assay, one determines a threshold cycle (Ct) which is the level of fluorescence that is considered to be significantly above the background level of fluorescence measured in the early cycles of the amplification. The Ct value is inversely proportional to the concentration of target: the lower the Ct, the higher the concentration of target.

In the following tables:
CT=Threshold Cycle;
RFU max=maximal Relative Fluorescence Units observed at the end of the PCR run;
CTL-=negative control;
N/A=sample whose level of fluorescence is below the background level;
Avg.: average.

Table 4 below gives illustrative experimental results:

| Sample | Group/Subtype | HIV1-M primers and probe CT | | Avg | HIV1-O primers and probe CT | | Avg |
|---|---|---|---|---|---|---|---|
| 201-1 | A | 37.6 | 38.3 | 38.0 | 44.3 | N/A | |
| 201-2 | B | 29.0 | 29.3 | 29.2 | N/A | N/A | |
| 201-3 | C | 37.5 | 38.8 | 38.2 | N/A | N/A | |
| 201-4 | D | 34.1 | 34.1 | 34.1 | N/A | N/A | |
| 201-5 | E | 32.1 | 35.2 | 33.7 | N/A | N/A | |
| 201-6 | F | 28.1 | 31.0 | 29.6 | N/A | N/A | |
| 201-7 | G | 31.9 | 32.0 | 32.0 | N/A | N/A | |
| 201-8 | H | 35.2 | 35.2 | 35.2 | N/A | N/A | |
| 201-9 | CTL- | N/A | N/A | | N/A | N/A | |
| 301-1 | O | N/A | N/A | | 32.4 | 31.8 | 32.1 |
| 301-2 | O | 41.1 | N/A | | 33.0 | 32.8 | 32.9 |
| 301-3 | O | N/A | N/A | | 30.9 | 31.0 | 31.0 |
| 301-4 | O | N/A | 47.5 | | N/A | 35.7 | 35.7 |
| Control (water) | | N/A | | | N/A | | |
| | | N/A | | | N/A | | |
| | | N/A | | | N/A | | |

The results are illustrated by FIGS. 4A and 4B.

On FIG. 4A, are shown the results obtained with the HIV1-M primers (H1B4f, H1B10r, SEQ ID NO: 7, 16) and HIV1-M probes (SH1BM5, SEQ ID NO: 119) of the invention on the HIV1-M panel (BBI PRD201), on the HIV1-O panel (BBI PRD301), and on the controls.

On FIG. 4B, are shown the results obtained with the HIV 1-O primers (H1B5f, H1B13r, SEQ ID NO: 140, 168) and HIV1-O probes (SH1BO2, SEQ ID NO: 191) of the invention on the HIV1-O panel, on the HIV1-M panel, and on the controls.

In both cases, no amplification is detected in quantitative real-time RT-PCR when the HIV1-M primers and probes of the invention are used on HIV1-O samples, and conversely.

Advantageously according to the invention, no cross-hybridization occurs between the HIV1-M amplicon and the HIV1-O probes, nor between the HIV1-O amplicon and the HIV1-M probes.

The HIV1-M and HIV 1-O primers and probes according to the invention have thus proven to allow for very high specificity detection in real-time quantitative RT-PCR conditions.

Example 3

HIV1-M and HIV1-O Quantification

This example illustrates that the primers and probes of the invention allows for quantification of HIV viral charge by RT-PCR.

The primers and probes have the following sequences:

```
HIV1-M primers:
Forward:
                            (H1B4f, SEQ ID NO: 7)
TTGGAGAGCAATGGCTAGTGA Reverse:
                           (H1B10r, SEQ ID NO: 16)
TGTGTGCAATCTAGTTGCCATA HIV1-M probe:
                                  (SEQ ID NO: 110)
ATAGTAGCCAGCTGTGATAAATGTC HIV1-O primers:
Forward:
                            (H1B5f, SEQ ID NO: 140)
TTGGAGAGCACTAGCTAGTGA Reverse:
                          (HIB13r, SEQ ID NO: 168)
TGTGTGCAATCTATTTGCCATA HIV1-O probe:
                                  (SEQ ID NO: 190)
GAAATCATTGCTAGTTGTCCTAAATGTCATAT
```

According to the invention, each probe is in this case produced as a molecular beacon, with "TGCGC" as target-unrelated arm in 5', and with "GCGCA" as target-unrelated arm in 3' (both arms are underlined). The 5' arm is labelled with a FAM fluorophore, and the 3' arm with a Dark Quencher.

Probe sequences are thus as follows (beacon arms are shown underlined):

```
HIV1-M probe in a molecular beacon format:
                             (SH1BM5, SEQ ID NO: 119)
FAM-TGCGCATAGTAGCCAGCTGTGATAAATGTCGCGCA-DQ HIV1-O probe in a molecular beacon format:
                             (SH1BO2, SEQ ID NO: 191)
FAM-TGCGCGAAATCATTGCTAGTTGTCCTAAATGTCATATGCGCA-DQ
```

Details of the RT-PCR procedure are as follows:
Panels:
BBI Performance Panel reference PRD301 (HIV1-O cultures diluted in human plasma at about $10^5$ copies per mL; sample numbers have the format 301-xx, wherein xx is the sample number) is used as representative HIV1-O panel;
BBI Performance Panel reference PRD201 (HIV1-M cultures diluted in human plasma at about $10^5$ copies per mL; sample numbers have the format 201-yy, wherein yy is the sample number) is used as representative HIV1-M panel, and corresponds to several different genotypes of the HIV1-M subtype;

BBI Accurun 315 panel series 500 (sub-type B) is used as a reference panel to produce the reference standard curve, constructed by plotting the log of known target concentrations against the corresponding Ct. The concentration of an unknown sample is then defined by mapping the corresponding Ct to the standard curve;

Negative controls: HIV1 negative plasma;

Extraction: Kit Qiagen QiaAmp Viral RNA (reference 52904) used in accordance with the manufacturer's recommendations (volume of sample for extraction: 140 microliters);

Primer pairs: HIV1-O primer pair (SEQ ID NO: 7, 8) and HIV1-M primer pair (SEQ ID NO: 1, 2) have each been used at 0.6 microM per reaction;

Probes: FAM-Dark Quencher probes (SEQ ID NO: 4, 10), 0.2 microM each per reaction;

RT-PCR reagents: RNAse-free water, and Qiagen Quanti-Tect Probe RT-PCR kit (Qiagen reference: 204443), according to the manufacturer's instructions, [MgCl$_2$] 4 mM;

Apparatus: IQ-Cycler Bio-Rad;

Thermal cycling:

30' at 42° C. (RT step),

15' at 95° C. (polymerase activation step), (15" at 94° C.-30" at 55° C.-30" at 72° C.)×50, +4° C.

Two series of amplification experiments are performed with the primers and probes of the invention:

a) RT-PCR with a single pair of primers and probes (HIV1-M primer pair (H1B4f, H1B10r, SEQ ID NO: 7, 16) and HIV1-M probe (SH1BM5, SEQ ID NO: 119);

b) RT-PCR with both pairs of primers and both probes (HIV1-M primer pair (H1B4f, H1B10r, SEQ ID NO: 7, 16)+HIV1-O primer pair (H1B5f, H1B13r, SEQ ID NO: 140, 168) and HIV1-M probe (SH1BM5, SEQ ID NO: 119)+HIV1-O probe (SH1B02, SEQ ID NO: 191)).

The Ct results of each assay are used for the quantification of panels PRD201 and PRD301 by mapping the corresponding Ct to the standard curve. The quantification values corresponding to the number of RNA copies/ml in each pure sample are compared with commercially-available kits used in accordance with the manufacturers' recommendations: kit Amplicor HIV1 Monitor Version 1.5 from Roche (ref 87674), kit Quantiplex HIV1 RNA 3.0 bDNA from Bayer (ref 6147) and kit Nuclisens HIV-1 QT from Organon Teknika (ref 84152).

Representative results are shown in Tables 5 and 6:

TABLE 5

(experiment a): Results obtained a single pair of primers (HIV1-M primer pair, H1B4f, H1B10r, SEQ ID NO: 7, 16) and a single probe (HIV1-M beacon probe, SEQ ID NO: 119) on the HIV1-M sample panel

| Sample | Genotype | Roche Amplicor | Bayer Quantiplex | Organon Nuclisens | Invention CT | Invention Avg. |
|---|---|---|---|---|---|---|
| 201-1 | A | 4.00E+03 | 3.00E+03 | 2.00E+03 | 37.8 | 2.80E+03 |
| 201-2 | B | 2.00E+05 | 8.00E+04 | 2.00E+05 | 29.2 | 4.30E+04 |
| 201-3 | C | 2.00E+03 | 5.00E+03 | 1.00E+04 | 36.8 | 3.90E+03 |
| 201-4 | D | 2.00E+05 | 1.00E+05 | 3.00E+05 | 30.9 | 2.50E+04 |
| 201-5 | E | 2.00E+05 | 9.00E+04 | 6.00E+04 | 33.9 | 9.80E+03 |
| 201-6 | F | 5.00E+05 | 9.00E+04 | 2.00E+05 | 28.7 | 5.00E+04 |
| 201-7 | G | 5.00E+05 | 8.00E+04 | 1.00E+05 | 32.3 | 1.60E+04 |
| 201-8 | H | 2.00E+05 | 3.00E+04 | 9.00E+04 | 34.7 | 7.60E+03 |
| 201-9 | Diluent | ND | ND | ND | N/A | |

It is apparent from these results that the HIV1-M primers and probes of the invention allow for an accurate real-time quantitative detection of all HIV1-M genotypes, and good correlation with the commercially available kits.

TABLE 6

(experiment b): Results obtained with HIV1-M and HIV1-O primers (H1B4f, H1B10r, H1B5f, H1B13r, SEQ ID NO: 7, 16, 140, 168) and HIV1-M and HIV1-O probes (SEQ ID NO: 119, 191) on the HIV1-O sample panel

| Sample | Genotype | Roche Amplicor | Bayer Quantiplex | Organon Nuclisens | Invention CT | Invention Avg. |
|---|---|---|---|---|---|---|
| 301-1 | O | ND | 3.00E+02 | <LDL | 32.1 | 1.60E+04 |
| 301-2 | O | ND | 2.00E+03 | <LDL | 32.9 | 1.00E+04 |
| 301-3 | O | ND | 8.00E+02 | <LDL | 31 | 1.40E+04 |
| 301-4 | O | ND | 3.00E+02 | <LDL | 35.7 | 2.00E+03 |
| 301-5 | Diluent | ND | ND | ND | N/A | |

It can be seen from Table 6 that the higher level of quantification on HIV1-0 panel is obtained with both HIV1-M and HIV1-O primers and probes of the invention. (<LDL=less than lower detection limit).

Example 4

HIV1/HIV2 Multiplex Assay (FIGS. 5A and 5B)

This example illustrates that the HIV1 and HIV2 primers and probes of the invention may be used in a multiplex assay for HIV1 or HIV2 signal. It also demonstrates the possibility to follow the fluorescence of two targets in the same tube by use of two different fluorophores (FAM and ROX).

The primers and probes have the following sequences:

```
HIV1-M primers:
Forward:
TTGGAGAGCAATGGCTAGTGA     (H1b4f, SEQ ID NO: 7)

Reverse:
TGTGTGCAATCTAGTTGCCATA    (GH1B10r, (SEQ ID NO: 16)

HIV1-M probe:
ATAGTAGCCAGCTGTGATAAATGTC(SEQ ID NO: 110)

HIV2 forward primer (H2A3f, SEQ ID NO: 195):
AGGAAGRCARACAGCACTCTTC
with R = A/G (Tm = 66° C.)

HIV2 reverse primer (H2A3r, SEQ ID NO: 250):
GGTACTCCRAAGGGGTTTGTTCTAT
with R = A/G (Tm = 65°)
```

-continued

```
HIV2-A probe (HIV2-A probe, SEQ ID NO: 297):
GGCCAATAACACACTTGCACACA
```

According to the invention, each probe is in this case produced as a molecular beacon, with "CGCGC" as target-unrelated arm in 5', and with "GCGCG" as target-unrelated arm in 3' (both arms are underlined). The 5' arm is labelled with a FAM or ROX fluorophore, and the 3' arm with a Dabcyl moiety.

Probe sequences are thus as follows (beacon arms are shown underlined):

```
HIV1-M probe in a molecular beacon format:
                        (SH1BM10, SEQ ID NO: 128)
FAM-CGCGCATAGTAGCCAGCTGTGATAAATGTCGCGCG-Dabcyl HIV2-A probe in a molecular beacon format:
ROX-CGCGCGGCCAATAACACACTTGCACACAGCGCG-Dabcyl
(HIV2-A beacon probe, SH2A14a, SEQ ID NO: 299)
```

Details of the RT-PCR procedure are as follows:
HIV2-A positive sample: obtained from infected patient (Centre Hospitalier Bichat, Laboratory of Virology, Assistance Publique—Hôpitaux de Paris, France);
BBI Accurun 315 panel series 500 (sub-type B);
Negative controls: HIV1 and HIV2 negative sample;
Extraction: Kit Qiagen QiaAmp Viral RNA (reference 52904) used in accordance with the manufacturer's recommendations (volume of sample for extraction: 140 microliters);
Primer pairs: HIV1-M primer pair (SEQ ID NO: 7, 16) and HIV2 primer pair (SEQ ID NO: 195, 250) have been used respectively at 0.5 microM each per reaction for HIV1-M and 0.3 microM each per reaction for HIV2;
Probes: HIV1-M FAM-Dabcyl probe (SEQ ID NO: 128) and HIV2-A ROX Dabcyl probe (SEQ ID N° 299), 0.4 microM each per reaction;
RT-PCR reagents: RNAse-free water, and Qiagen Quanti-Tect Probe RT-PCR kit (Qiagen reference: 204443), according to the manufacturer's instructions, [$MgCl_2$] 4 mM;
Apparatus: IQ-Cycler Bio-Rad;
Thermal cycling:
30' at 42° C. (RT step),
15' at 95° C. (polymerase activation step),
(15" at 94° C.-30" at 55° C.-30" at 72° C.)×50, +4° C.
Two series of amplification experiments have been performed with the primers and probes of the invention:
a) RT-PCR with a single pair of primers and probe HIV1-M (H1B4f, H1B10r, SH1BM10, SEQ ID NO: 7, 16, 119, a single pair of primers and probe HIV2 (H2A3f, H2A3r, SH2A14a, SEQ ID NO: 195, 250, 299) with a range of HIV1-M target concentrations.
b) RT-PCR with a single pair of primers and probe HIV1-M (H1B4f, H1B10r, SH1BM10, SEQ ID NO: 7, 16, 119), a single pair of primers and probe HIV2 (H2A3f, H2A3r, SH2A14a, SEQ ID NO: 195, 250, 299) with a range of HIV2 target dilutions.
Interpretation of the results: for each assay one determines a threshold cycle (Ct) which is the level of fluorescence that is considered to be significantly above the background level of fluorescence measured in the early cycles of the amplification. The Ct value is inversely proportional to the concentration of target: the lower the Ct, the higher the concentration of target.

In the following tables, CT=Threshold Cycle; RFU max=maximal Relative Fluorescence Units observed at the end of the PCR run; CTL-=negative control; N/A=sample whose level of fluorescence is below the background level; Avg=average; cop=copies.

Illustrative Ct results are shown in Table 7:

| HIV1-M | | | | HIV2-A | | | |
|---|---|---|---|---|---|---|---|
| Number cop/PCR | CT | CT | Avg | Dilution | CT | CT | Avg |
| 10000 | 28.2 | 28.2 | 28.2 | 1/300 | 28.0 | 27.7 | 27.9 |
| 1000 | 31.6 | 31.3 | 31.5 | 1/3000 | 31.9 | 32.4 | 32.2 |
| 100 | 35.7 | 35.7 | 35.7 | 1/30000 | 36.6 | 36.7 | 36.7 |
| 10 | 39.4 | N/A | 39.4 | 1/300000 | 40.7 | N/A | 40.7 |
| CTL- (water) | N/A | N/A | | CTL- (water) | N/A | N/A | |

Its is apparent from these results that the HIV1 and HIV2 primers and probe of the invention may be used in a multiplex assay for the detection of HIV1-M or HIV2 target.

The results are illustrated by FIGS. 5A and 5B (for each dilution, there are 2 curves since experiments are here carried out in duplicate).

Example 5

HIV2/IC Multiplex Assay (FIGS. 6A and 6B)

This example illustrates that the HIV2 target and internal control (IC) may be co-amplified using the HIV2 primers and probes of the invention and selected IC primers and probe without any perturbation of the HIV2 signal. It also demonstrates the possibility to follow the fluorescence of two targets in the same tube by use of two different fluorophores (ROX and TAMRA)

This example involves the use of one pair of HIV2 primers and one HIV2 probe. These primers and probes target a 147 bp sequence in HIV2 isolates. They have the following sequences:

```
HIV2 forward primer (H2A3f, SEQ ID NO: 195):
AGGAAGRCARACAGCACTCTTC
with R = A/G (Tm = 66° C.)

HIV2 reverse primer (H2A3r, SEQ ID NO: 250):
GGTACTCCRAAGGGGTTTGTTCTAT
with R = A/G (Tm = 65°)

HIV2-A probe (HIV2-A probe, SEQ ID NO: 297):
GGCCAATAACACACTTGCACACA
```

This example also involves the use of one pair of IC primers and one IC probe, selected to get the same amplified fragment size and GC % than the HIV target.

Each of these probes is used as a molecular beacon in this example. The target-unrelated beacon arms which have been added at each end of the HIV2 probe is shown underlined (ROX=fluorophore; Dabcyl=quencher).

```
HIV2-A probe in molecular beacon format
(HIV2-A beacon probe, SH2A14a, SEQ ID NO: 299):
ROX-CGCGCGGCCAATAACACACTTGCACACAGCGCG-Dabcyl
```

For IC probe, TAMRA has been chosen as fluorophore and Dabcyl as quencher.

Two series of real-time quantitative amplification experiments have been performed:
a) HIV2 primer pair+HIV2-A beacon probe (H2A3f, H2A3r, SH2A9a, SEQ ID NO: 195, 250, 299)+IC primers pair+IC beacon probe with addition of HIV2 target alone;
b) HIV2 primer pair+HIV2-A beacon probe (H2A3f, H2A3r, SH2A9a, SEQ ID NO: 195, 250, 299)+IC primers pair+IC beacon probe with addition of HIV2 target and IC.

Details of the procedure are as follows:
HIV2-A positive sample: obtained from infected patient (Centre Hospitalier Bichat, Laboratory of Virology, Assistance Publique—Hôpitaux de Paris, France);
IC dilution: IC is diluted in order to obtain $10^6$ cop/PCR;
Negative controls: HIV2-negative plasma;
Nucleic acid extraction: Kit Qiagen QiaAmp Viral RNA (reference 52904) used in accordance with the manufacturer's recommendations (volume of sample for extraction=140 microliters);
Primer pair: 0.3 microM each per reaction (SEQ ID NO: 11, 12 and IC primers);
Probes: HIV2-A Rox-Dabcyl beacon probe as described above (SEQ ID n° 299) and IC Tamra-Dabcyl beacon probe, 0.4 microM each per reaction;
RT-PCR reagents: RNAse-free water, and Qiagen QuantiTect Probe RT-PCR kit (Qiagen reference: 204443) used according to the manufacturer's instructions, $[MgCl_2]$= 4 mM;

Apparatus: IQ-Cycler Bio-Rad;
Thermal cycling:
    30' at 42° C. (RT step),
    15' at 95° C. (polymerase activation step),
    (30" at 94° C.-30" at 55° C.-30" at 72° C.)×50, +4° C.

HIV2-A positive sample was submitted to nucleic acid extraction and, after dilution to ⅓00, ⅓000 and ⅓0000 in water to RT-PCR amplification as described in experiments a) and b).

IC dilution was submitted to RT-PCR amplification (around $10^6$ cop/PCR) as described in experiment b). (cop=copies).

Interpretation of results: for each assay is determined a threshold cycle (Ct) which is the level of fluorescence that is considered to be significantly above the background level of fluorescence measured in the early cycles of the amplification. The Ct value is inversely proportional to the concentration of target: the lower the Ct, the higher the concentration of target.

In the following tables, CT=Threshold Cycle; max RFU=maximal Relative Fluorescence Units observed at the end of the PCR run; CTL-=negative control; N/A=sample whose level of fluorescence is below the background level.

TABLE 8

CT values obtained with HIV2 primer pair + HIV2-A beacon probe + IC primer pair + IC beacon probe in experiments a) and b) (H2A3f, H2A3r, SH2A14a, SEQ ID NO: 195, 250, 299 for HIV2) when fluorescence of ROX is read (HIV2 signal)

| Assay conditions | HIV2-A 1/300 | | | | HIV2-A 1/3000 | | | | HIV2-A 1/30000 | | | |
|---|---|---|---|---|---|---|---|---|---|---|---|---|
| | CT | CT | CT | Avg | CT | CT | CT | Avg | CT | CT | CT | Avg |
| Exp. a): HIV2 target | 25.3 | 25.4 | 25.7 | 25.5 | 28.8 | 28.2 | 28.8 | 28.6 | 32.3 | 33.0 | 32.7 | 32.7 |
| Exp. b): HIV2 target + IC | 25.4 | 25.3 | 25.4 | 25.4 | 29.0 | 20.3 | 28.7 | 29.0 | 33.0 | 34.1 | 34.8 | 34.0 |

It can be seen from this table that the HIV2 Ct values did not change with addition of IC, irrespective of the dilution of HIV2-A extracted sample tested (⅓00, ⅓000, ⅓0000).

TABLE 9

CT values obtained with HIV2 primer pair + HIV2-A beacon probe + IC primer pair + IC beacon probe in experiment b) (H2A3f, H2A3r, SH2A14a, SEQ ID NO: 195, 250, 299 for HIV2) when fluorescence of TAMRA is read (IC signal)

| | IC | | | | | | | | | | | |
|---|---|---|---|---|---|---|---|---|---|---|---|---|
| Assay conditions | HIV2-A 1/300 | | | | HIV2-A 1/3000 | | | | HIV2-A 1/30000 | | | |
| | CT | CT | CT | Avg | CT | CT | CT | Avg | CT | CT | CT | Avg |
| Exp. b): IC + HIV2 target | 28.5 | 28.7 | 28.7 | 28.6 | 27.2 | 27.7 | 28.0 | 27.6 | 27.7 | 27.7 | 27.7 | 27.7 |

It can be seen from this table that the IC Ct values are very reproducible irrespective of the dilution of HIV2-A extracted sample added.

These results are illustrated by FIGS. 6A, 6B and 6C (for each dilution of HIV2-A, there are 3 curves since experiments are here carried out in triplicate in FIGS. 6A and 6B; there are 6 curves for the negative control; and there are 9 curves for the IC, all with the same concentration on FIG. 6C).

The invention claimed is:

1. A polynucleotide selected from the group consisting of:
   SEQ ID NO: 2 and the fragments of SEQ ID NO: 2 selected from SEQ ID NO: 306, SEQ ID NO: 307, SEQ ID NO: 308;
   SEQ ID NO: 4 and the fragments of SEQ ID NO: 4 selected from SEQ ID NO: 310, SEQ ID NO: 311;
   SEQ ID NO: 5
   SEQ ID NO: 1 and the fragment thereof of SEQ ID NO: 305; and
   SEQ ID NO: 3 and the fragment thereof of SEQ ID NO: 309.

2. An amplicon obtainable by implementation of a process for the detection of at least one HIV target on a HIV-containing sample, wherein said process comprises the step of producing at least one amplicon by means of at least two oligonucleotides, wherein said at least two oligonucleotides are primers which are structurally suitable for specifically amplifying at least one reference template sequence selected from the group consisting of:

SEQ ID NO: 2 and the fragments of SEQ ID NO: 2 selected from SEQ ID NO: 306, SEQ ID NO: 307, SEQ ID NO: 308;

SEQ ID NO: 4 and the fragments of SEQ ID NO: 4 selected from SEQ ID NO: 310, SEQ ID NO: 311;

SEQ ID NO: 5;

SEQ ID NO: 1 and the fragment thereof of SEQ ID NO: 305; and

SEQ ID NO: 3 and the fragment thereof of SEQ ID NO: 309;

wherein said primers are structurally suitable for annealing to said HIV reference isolate at such positions that they target on said HIV reference isolate a sequence, which consists of said reference template sequence, wherein the nucleotide length of said amplicon is the nucleotide length of a polynucleotide of claim 1.

3. An amplification composition comprising at least one amplicon of claim 2.

4. The amplicon of claim 2, wherein said process further comprises the step of detecting said amplicon by means of at least one probe.

5. The amplicon of claim 4, wherein each of the 5' and 3' ends of said at least one probe is directly linked to an oligonucleotide of 5-10 nucleotides, said 5' end oligonucleotide and said 3' end oligonucleotide being hybridized together and imparting a hairpin structure to said at least one probe when said at least one probe is not hybridized to said amplicon.

6. An isolated oligonucleotide suitable for HIV detection, selected from the group consisting of:
SEQ ID NOs: 24, 190, 221, 276, 297 and 300, and
SEQ ID NOs: 190, 297 and 300, wherein each of the 5' and 3' ends of said sequence of SEQ ID NO: 190, 297 or 300 is directly linked to an oligonucleotide of 5-10 nucleotides, said 5' end oligonucleotide and said 3' end oligonucleotide being hybridized together and imparting a hairpin structure to said sequence of SEQ ID NO: 190, 297 or 300 when said sequence of SEQ ID NO: 190, 297 or 300 is unhybridized.

7. The isolated oligonucleotide of claim 6 consisting of SEQ ID NO: 24.

8. The isolated oligonucleotide of claim 6, selected from the group consisting of:
SEQ ID NO: 190; and
SEQ ID NO: 190, wherein each of the 5' and 3' ends of said sequence of SEQ ID NO: 190 is directly linked to an oligonucleotide of 5-10 nucleotides, said 5' end oligonucleotide and said 3' end oligonucleotide being hybridized together and imparting a hairpin structure to said sequence of SEQ ID NO: 190 when said sequence of SEQ ID NO: 190 is unhybridized.

9. The isolated oligonucleotide of claim 6 consisting of SEQ ID NO: 221.

10. The isolated oligonucleotide of claim 6 consisting of SEQ ID NO: 276.

11. The isolated oligonucleotide of claim 6, wherein said oligonucleotide is fluorescently labelled.

12. A set of oligonucleotides, comprising at least two oligonucleotides selected from a first group consisting of:
the oligonucleotide consisting of SEQ ID NO: 12,
the oligonucleotide consisting of SEQ ID NO: 24, and
an oligonucleotide selected from a second group consisting of: SEQ ID NO: 118, and
SEQ ID NO: 118, wherein each of the 5' and 3' ends of said sequence of SEQ ID NO: 118 is directly linked to an oligonucleotide of 5-10 nucleotides, said 5' end oligonucleotide and said 3' end oligonucleotide being hybridized together and imparting a hairpin structure to said sequence of SEQ ID NO: 118 when said sequence of SEQ ID NO: 118 is unhybridized,
wherein said set specifically detects HIV.

13. A set of oligonucleotides, comprising at least one oligonucleotide selected from the group consisting of:
SEQ ID NO: 190 and
SEQ ID NO: 190, wherein each of the 5' and 3' ends of said sequence of SEQ ID NO: 190 is directly linked to an oligonucleotide of 5-10 nucleotides, said 5' end oligonucleotide and said 3' end oligonucleotide being hybridized together and imparting a hairpin structure to said sequence of SEQ ID NO: 190 when said sequence of SEQ ID NO: 190 is unhybridized,
wherein said set specifically detects HIV.

14. A set of oligonucleotides, comprising at least one oligonucleotide selected from the group consisting of:
SEQ ID NO: 221;
SEQ ID NO: 276;
SEQ ID NO: 297; and
SEQ ID NO: 297, wherein each of the 5' and 3' ends of said sequence of SEQ ID NO: 297 is directly linked to an oligonucleotide of 5-10 nucleotides, said 5' end oligonucleotide and said 3' end oligonucleotide being hybridized together and imparting a hairpin structure to said sequence of SEQ ID NO: 297 when said sequence of SEQ ID NO: 297 is unhybridized,
wherein said set specifically detects HIV.

15. A set of oligonucleotides, comprising at least one oligonucleotide selected from the group consisting of:
SEQ ID NO: 221;
SEQ ID NO: 276;
SEQ ID NO: 300; and
the oligonucleotide of SEQ ID NO: 300, wherein each of the 5' and 3' ends of said sequence of SEQ ID NO: 300 is directly linked to an oligonucleotide of 5-10 nucleotides, said 5' end oligonucleotide and said 3' end oligonucleotide being hybridized together and imparting a hairpin structure to said sequence of SEQ ID NO: 300 when said sequence of SEQ ID NO: 300 is unhybridized,
wherein said set specifically detects HIV.

16. A set of oligonucleotides, comprising at least one oligonucleotide selected from the group consisting of:
SEQ ID NO: 190;
SEQ ID NO: 297;
SEQ ID NO: 300; and
SEQ ID NO: 190, wherein each of the 5' and 3' ends of said sequence of SEQ ID NO: 190 is directly linked to an oligonucleotide of 5-10 nucleotides, said 5' end oligonucleotide and said 3' end oligonucleotide being hybridized together and imparting a hairpin structure to said sequence of SEQ ID NO: 190 when said sequence of SEQ ID NO: 190 is unhybridized;
SEQ ID NO: 297, wherein each of the 5' and 3' ends of said sequence of SEQ ID NO: 297 is directly linked to an oligonucleotide of 5-10 nucleotides, said 5' end oligonucleotide and said 3' end oligonucleotide being hybridized together and imparting a hairpin structure to said sequence of SEQ ID NO: 297 when said sequence of SEQ ID NO: 297 is unhybridized; and
SEQ ID NO: 300, wherein each of the 5' and 3' ends of said sequence of SEQ ID NO: 300 is directly linked to an oligonucleotide of 5-10 nucleotides, said 5' end oligonucleotide and said 3' end oligonucleotide being hybridized together and imparting a hairpin structure to said sequence of SEQ ID NO: 300 when said sequence of SEQ ID NO: 300 is unhybridized;
wherein said set specifically detects HIV.

17. A set of oligonucleotides according to any one of claims 12-16, wherein at least one of said oligonucleotides is fluorescently labelled.

18. An amplicon obtainable by amplification from a HIV-containing sample with a pair of primers selected from:
a primer of SEQ ID NO: 12 and a primer of SEQ ID NO: 24; or
a primer of SEQ ID NO: 221 and a primer of SEQ ID NO: 276.

19. An amplicon, which has a nucleotide length identical to the nucleotide length of a polynucleotide of claim 1, and which comprises a sequence having a percentage of nucleotide identity of at least 90% with a probe sequence, over the entire length of this probe sequence, wherein this probe sequence is selected from the group consisting of SEQ ID NO: 118, 190, 297, 300 and the sequences, which are complementary to these probe SEQ ID NO: sequences over the entire length of these probe SEQ ID NO: sequences.

20. An amplification composition comprising the amplicon of claim 18 or 19.

21. A kit comprising:
a. at least one oligonucleotide selected from the group consisting of SEQ ID NOs: 24, 190, 221, 276, 297 and 300; and/or
b. at least one set of oligonucleotides of any one of claims 12-16, wherein at least one of the oligonucleotides of said at least one set is optionally fluorescently labelled; and
c. optionally, instructions for the use thereof,
wherein said kit is for HIV diagnostics.

22. The isolated oligonucleotide of claim 6, selected from the group consisting of:
the oligonucleotides of SEQ ID NOs: 297 and 300; and
the oligonucleotides of SEQ ID NOs: 297 and 300, wherein each of the 5' and 3' ends of said sequence of SEQ ID NO: 297 or 300 is directly linked to an oligonucleotide of 5-10 nucleotides, said 5' end oligonucleotide and said 3' end oligonucleotide being hybridized together and imparting a hairpin structure to said sequence of SEQ ID NO: 297 or 300 when said sequence of SEQ ID NO: 297 or 300 is unhybridized.

23. The isolated oligonucleotide of claim 6, wherein said oligonucleotide of SEQ ID NO: 24 is one of SEQ ID NOs: 16-23 and/or said oligonucleotide of SEQ ID NO: 221 is one of SEQ ID NOs: 195-220 and/or said oligonucleotide of SEQ ID NO: 276 is one of SEQ ID NOs: 250-275.

24. The set of oligonucleotides of claim 12, wherein said oligonucleotide of SEQ ID NO: 12 is one of SEQ ID NOs: 10-11 and/or said oligonucleotide of SEQ ID NO: 24 is one of SEQ ID NOs: 16-23 and/or said oligonucleotide of SEQ ID NO: 118 is one of SEQ ID NOs: 110-117.

25. The set of oligonucleotides of claim 14, wherein said oligonucleotide of SEQ ID NO: 221 is one of SEQ ID NOs: 195-220 and/or said oligonucleotide of SEQ ID NO: 276 is one of SEQ ID NOs: 250-275.

26. The set of oligonucleotides of claim 15, wherein said oligonucleotide of SEQ ID NO: 221 is one of SEQ ID NOs: 195-220 and/or said oligonucleotide of SEQ ID NO: 276 is one of SEQ ID NOs: 250-275.

* * * * *